US009068015B2

(12) United States Patent
Jorgensen et al.

(10) Patent No.: US 9,068,015 B2
(45) Date of Patent: *Jun. 30, 2015

(54) THERAPEUTIC USE OF A GROWTH FACTOR, METRNL

(71) Applicant: NsGene A/S, Ballerup (DK)

(72) Inventors: Jesper Roland Jorgensen, Frederiksberg (DK); Lone Fjord-Larsen, Rødovre (DK); Lars Ulrik Wahlberg, Tiverton, RI (US); Nuno Miguel Gomes Andrade, Vienna (AT); Teit E. Johansen, Hørsholm (DK)

(73) Assignee: NsGene A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/715,440

(22) Filed: Dec. 14, 2012

(65) Prior Publication Data

US 2013/0267464 A1 Oct. 10, 2013

Related U.S. Application Data

(63) Continuation of application No. 12/936,501, filed as application No. PCT/DK2009/050165 on Jul. 7, 2009, now Pat. No. 8,334,264.

(60) Provisional application No. 61/083,316, filed on Jul. 24, 2008.

(30) Foreign Application Priority Data

Jul. 24, 2008 (DK) .............................. 2008 01036

(51) Int. Cl.
| | |
|---|---|
| *A01N 37/18* | (2006.01) |
| *A61K 38/00* | (2006.01) |
| *C07K 1/00* | (2006.01) |
| *C07K 14/00* | (2006.01) |
| *C07K 14/475* | (2006.01) |
| *C07K 14/48* | (2006.01) |

(52) U.S. Cl.
CPC ............... *C07K 14/475* (2013.01); *A61K 38/00* (2013.01); *C07K 14/48* (2013.01)

(58) Field of Classification Search
None
See application file for complete search history.

(56) References Cited

U.S. PATENT DOCUMENTS

| | | | |
|---|---|---|---|
| 5,981,277 | A | 11/1999 | Fransen et al. |
| 8,334,264 | B2 * | 12/2012 | Jorgensen et al. ........... 514/18.2 |
| 8,404,642 | B2 | 3/2013 | Jorgensen et al. |
| 2007/0275026 | A1 | 11/2007 | Gronborg et al. |
| 2012/0184492 | A1 | 7/2012 | Gronborg et al. |
| 2013/0303459 | A1 | 11/2013 | Jorgensen et al. |

FOREIGN PATENT DOCUMENTS

| | | |
|---|---|---|
| WO | 92/19195 | 11/1992 |
| WO | 93/22437 | 11/1993 |
| WO | 95/05452 | 2/1995 |
| WO | 97/44065 | 11/1997 |
| WO | 01/25427 | 4/2001 |
| WO | 01/39786 | 6/2001 |
| WO | 01/54474 | 8/2001 |
| WO | 01/55301 | 8/2001 |
| WO | 01/55440 | 8/2001 |
| WO | 01/57190 | 8/2001 |
| WO | 01/83510 | 11/2001 |
| WO | 03/066877 | 8/2003 |
| WO | 2004/035732 | 4/2004 |
| WO | 2004/079014 | 9/2004 |
| WO | 2005/095450 | 10/2005 |
| WO | 2006/110593 | 10/2006 |

OTHER PUBLICATIONS

Anderson et al., "Ciliary Neurotrophic Factor Protects Striatal Output Neurons in an Animal Model of Huntington Disease," *Proc. Natl. Acad. Sci. USA*, 1996, 93:7346-7351.
Colton, "Engineering Challenges in Cell-Encapsulation Technology," *Trends Biotechnol.* 1996, 14:158-162.
Fransen et al., "Molecular Cloning of a Novel Macrophaged Derived Cytokine (SMAF-1) and its Immunomodulating Capacities ," published at the Seventh Annual Conference of the International Cytokine Society, Hilton Head, SC USA, Dec. 5-9, 1999 , p. 975, Abstract 254, 1 page.
Fransson et al., "A Novel Neurotrophic Factor Supports Spiral Ganglion Neuron Survival and Their Electrical Responsiveness In Vivo," Karolinska Institutet, NsGene NS, Poster, 2010, ANS/AuPS 2010 Joint Meeting, Sydney, Australia, 1 page.
GenBank Accession No. AAH00662, Nov. 29, 2000, 2 pages.
GenBank Accession No. AAH37181, Sep. 23, 2002, 2 pages.
GenBank Accession No. AAH88383, Dec. 22, 2004, 2 pages.
GenBank Accession No. AAK61247, Jun. 8, 2001, 2 pages.
GenBank Accession No. AAM78739, Nov. 6, 2001, 1 page.
GenBank Accession No. AAM79723, Nov. 6, 2001, 1 page.
GenBank Accession No. ABA06589, Jan. 10, 2002, 3 pages.
GenBank Accession No. ABA06759, Jan. 10, 2002, 3 pages.
GenBank Accession No. ABB1 0367, Jan. 10, 2002, 3 pages.
GenBank Accession No. ABB1 0537, Jan. 10, 2002, 3 pages.
GenBank Accession No. ABB57447, Mar. 15, 2002, 1page.
GenBank Accession No. ADP29324, Aug. 12, 2004, 2 pages.
GenBank Accession No. BG806341, Dec. 21, 2001, 1 page.
GenBank Accession No. CAB56188, Sep. 17, 1999, 2 pages.
GenBank Accession No. NP 076947, Feb. 27, 2001, 2 pages.
Gong et al., "Metrnl: A New Secreted Protein Inhibit Differentiation of MG-63," *Journal of Bone and Mineral Research*, 2007, 22:S142, 1 page.

(Continued)

*Primary Examiner* — Olga N Chernyshev
(74) *Attorney, Agent, or Firm* — Fish & Richardson P.C.

(57) ABSTRACT

The present invention relates to the field of therapeutic use of proteins, genes and cells, in particular to the therapy based on the biological function of a secreted therapeutic protein, METRNL, in particular for the treatment of disorders of the nervous system. METRNL is a Nerve Survival and Growth factor with neuroprotective and/or neurogenesis effects.

4 Claims, 11 Drawing Sheets

(56) References Cited

OTHER PUBLICATIONS

Gronborg et al, "Identification of Secreted Neurotrophic Factors Using Bioinformatics Combined with Expression Analysis," Program No. 825.2, Abstract Viewer/Itinerary Planner, Washington, DC: Society for Neuroscience, 2005, Abstract Only, 1 page.
International Search Report in International Application No. PCT/DK2009/050165, mailed Jul. 12, 2009, 8 pages.
Jackowski. "Neural Injury Repair: Hope for the Future as Barriers to Effective CNS Regeneration Become Clearer," *British Journal of Neurosurgery*, 1995, 9:303-317.
Jorgensen et al., "Characterization of Meteorin—An Evolutionary Conserved Neurotrophic Factor," *J. Mol. Neurosci.*, 2009, 13 pages.
Jorgensen et al., "Lentiviral Delivery of Meteorin Protects Striatal Neurons Against Exitotoxicity and Reverses Motor Deficits in the Quinolinic Acid Rat Model," *Neurobiology of Disease*, doi:10:10.1016/j.nbd.2010.09.003, 2010, 9 pages.
Jorgensen et al., "Poster 323.8: Meteorin and Meteorin-Like Initial Characterization of a Novel Growth Factor Family," Presented at SfN Meeting, 2008, 1 page.
Jorgensen et al., Poster: "Meteorin Protects Striatal Neurons and Improves Behavior in a Rat Model of Huntington's Disease," Jan. 28, 2010, 1 page.
Mizuno et al., "Brain-Derived Neurotrophic Factor Promotes Differentiation of Striatal GABAergic Neurons," *Dev Biol.* 1994, 165:243-256.
Mu et al., "Gene Expression in the Developing Mouse Retina by EST Sequencing and Microarray Analysis," *Nucl. Acids Res.*, 2001, 24:4983-4993.
Navarro-Galvel et al., "HNSG33 Effects on Survival and Differentiation of Human Neural Stem Cell-Derived Neuronal and Glial Progeny," Program No. 248.14, Abstract Viewer/Itinerary Planner, Washington DC: Society for Neuroscience, 2005, 2 pages.
Nishino et al., "Meteorin: A Secreted Protein that Regulates Glial Cell Differentiation and Promotes Axonal Extension," *The EMBO Journal*, 2004, 23:1998-2008.
Ramialison et al., "Rapid Identification of PAX2/51 Direct Downstream Targets in the Otic Vesical by Combinatorial Use of Bioinformatics Tools," *Genome Biology*, 2008, 9:R145 (11 pages).
Rudinger, "In Peptide Hormones," University Park Press, Ed. Parsons, 1976, pp. 1-7.
Todoroki et al., "Ropivacaine Inhibits Neurite Outgrowth in PC-12 Cells," *Anesth. Analg.*, 2004, 99:828-832.
Ventimiglia et al., "The Neurotrophins BDNF, NT-3 and NT-4/5 Promote Survival and Morphological and Biochemical Differentiation of Striatal Neurons In Vitro," *Eur. J. Neurosci.*, 1995, 7:213-222, Abstract Only, 1 page.
Walker et al., "Application of a Rat Multiple Tissue Gene Data Set," *Genome Res.*, 2004, 14:742-749.
Written Opinion in International Application No. PCT/DK2009/050165, mailed Jul. 12, 2009, 5 pages.
Haughey et al., "Disruption of neurogenesis in the subventricular zone of adult mice, and in human cortical neuronal precursor cells in culture, by amyloid beta-peptide: implications for the pathogenesis of Alzheimer's disease," Neuromolecular Med., 2002, 1(2):125-35 (Abstract Only).
Jorgensen et al., "Cometin is a novel neurotrophic factor that promotes neurite outgrowth and neuroblast migration in vitro and supports survival of spiral ganglion neurons in vivio," Experimental Neurology, 2012, 233:172-181.
Lim et al., "The adult neural stem cell niche: lessons for future neural cell replacement strategies," Neurosurg Clin N Am., Jan. 2007, 18(1):81-92 (Abstract Only).
Matheson et al., "Glial Cell Line-Derived Neurotrophic Factor (GDNF) is a Neurotrophic Factor for Sensory Neurons: Comparison with the Effects of the Neurotrophins," J Neurobiol., 1997, 32(1):22-32.
Tattersfield et al., "Neurogenesis in the striatum of the quinolinic acid lesion modle of Huntington's disease," Neuroscience, 2004, 127(2):319-32 (Abstract Only).
Tanaka et al., "Increased Expression of the Neurotrophic Growth Factor Meteorin-Like Protein in Lesional Skin of Individuals with Familial Primary Localized Cutaneous Amyloidosis," Kings College London, 39th Annual Meeting of European Society Dermatological Res., Sep. 9-12, 2009, Budapest, Hungary, Poster, 1 page.

\* cited by examiner

```
hMETRNL    MRGAARAAWGRAGQPWPRPPAPGPPPPPLPLLLLLLAGLLGGAGAQYSSDRCSWKGSGLT
mMETRNL    MRGAVWAARRRACQQWPRSPCPGPGPPPPPPLLLLLLLLLGGASAQYSSDLCSWKGSCLT
rMETRNL    MRGVVWAARRRAGQQWPRSPGPGPGPPPPPPLLLLLLLLLGGASAQYSSDLCSWKGSGLT
           *      ** * * * * * ***    * ** ****** hMETRNL    HEAHRKEVEQVYLRCAAGAVEWMYPTGALIVNLRPNTFSPARHLTVCIRSFTDSSGANIY
mMETRNL    REARSKEVEQVYLRCSAGSVEWMYPTGALIVNLRPNTFSPAQNLTVCIKPFRDSSGANIY
rMETRNL    REAHSKEVEQVYLRCSAGSVEWMYPTGALIVNLRPNTFSPAQNLTVCIKPFRDSSGANIY
              ******  ******************   **  * ******* hMETRNL    LEKTGELRLLVPDGDGRPGRVQCFGLEQGGLFVEATPQQDIGRRTTGFQYELVRRHRASD
mMETRNL    LEKTGELRLLVRDIRGEPGQVQCFSLEQGGLFVEATPQQDISRRTTGFQYELMSGQRGLD
rMETRNL    LEKTGELRLLVRDVRGEPGQVQCFSLEQGGLFVEATPQQDISRRTTGFQYELMSGQRGLD
           ***********  *     **************** ******      *  * hMETRNL    LHELSAPCRPCSDTEVLLAVCTSDFAVRGSIQQVTHEPERQDSAIHLRVSRLYRQKSRVF
mMETRNL    LHVLSAPCRPCSDTEVLLAICTSDFVVRGFIEDVTHVPEQQVSVIYLRVNRLHRQKSRVF
rMETRNL    LHVLSAPCRPCSDTEVLLAICTSDFVVRGFIEDVTHVPEQQVSVIHLRVSRLHRQKSRVF
            ************ * * *  *   * ** * *  ******* hMETRNL    EPVPEGDGHWQGRVRTLLECGVRPGHGDFLFTGHMHFGEARLGCAPRFKDFQRMYRDAQE
mMETRNL    QPAPEDSGHWLGHVTTLLQCGVRPGHGEFLFTGHVHFGEAQLGCAPRFSDFQRMYRKAEE
rMETRNL    QPAPEDSGHWLGHVTTLLQCGVRPGHGEFLFTGHVHFGEAQLGCAPRFSDFQKMYRKAEE
            *   *  *  * **** ** ** *** * ***  * * hMETRNL    RGLNPCEVGTD
mMETRNL    MGINPCEINME
rMETRNL    RGINPCEINME
            * ****
```

Fig. 1

```
hMETRNL   MRGAARAAWGRAGQPWPRPPAPGPPPPPLPLLLLLLAGLLGG-AG-AQYSSDRCSWKGSG
mMETRNL   MRGAVWAARRRAGQQWPRSPGPGPGPPPPPPLLLLLLLLLGG-AS-AQYSSDLCSWKGSG
rMETRNL   MRGVVWAARRRAGQQWPRSPGPGPGPPPPPPLLLLLLLLLGG-AS-AQYSSDLCSWKGSG
hMETRN    -MGFPAAA--------------------AARAGYSEERCSWRGSG
mMETRN    MLVAT-----------------------LLCALCCGLLAASAH-AGYSEDRCSWRGSG
rMETRN    MLVAA-----------------------LLCALCCGLLAASAR-AGYSEDRCSWRGSG
                                             *   *    *    * *** hMETRNL   LTHEAHRKEVEQVYLRCAAGAVEWMYPTGALIVNLR---PNTFSPARHLTVCIRSFTDSS
mMETRNL   LTREARSKEVEQVYLRCSAGSVEWMYPTGALIVNLR---PNTFSPAQNLTVCIKPFRDSS
rMETRNL   LTREAHSKEVEQVYLRCSAGSVEWMYPTGALIVNLR---PNTFSPAQNLTVCIKPFRDSS
hMETRN    LTQEP--GSVGQLALACAEGAVEWLYPAGALRLTLGGPDPRA----RPGIACLRPVRPFA
mMETRN    LTQEP--GSVGQLTLDCIEGAIEWLYPAGALRLTLGGPDPGT----RPSIVCLRPERPFA
rMETRN    LTQEP--GSVGQLTLDCIEGAIEWLYPAGALRLTLGGSDPGT----RPSIVCLRPTRPFA
          ** *       *   * *    *   ***    *            * hMETRNL   GANIYLEK-TG-ELRLLVPDGDGRPGRVQC--FG-LEQGGLFVEATPQQDIGRRTTGFQY
mMETRNL   GANIYLEK-TG-ELRLLVRDIRGEPGQVQC--FS-LEQGGLFVEATPQQDISRRTTGFQY
rMETRNL   GANIYLEK TG ELRLLVRDVRGEPGQVQC  FS LEQGGLFVEATPQQDISRRTTGFQY
hMETRN    GAQVFAER-AGGALELLLAEGPGPAGG-RCVRWGPRERRALFLQATPHQDISRRVAAFRF
mMETRN    GAQVFAERMTG-NLELLLAEGPDLAGG-RCMRWGPRERRALFLQATPHRDISRRVAAFRF
rMETRN    GAQVFAERMAG-NLELLLAEGQGLAGG-RCMRWGPRERRALFLQATPIIRDISRRVAAFQF
          **       *     *   *   **   *         *    *     * hMETRNL   ELVRRRHRAS---DLHE-----LSAP--CRPCSDTEVLLAVCTSDFAVRGSIQQVFHEPER
mMETRNL   ELMSGQRGL---DLHV-----LSAP--CRPCSDTEVLLAICTSDFVVRGFIEDVTHVPEQ
rMETRNL   ELMSGQRGL---DLHV-----LSAP--CRPCSDTEVLLAICTSDFVVRGFIEDVTHVPEQ
hMETRN    ELREDGRPELPPQAHG-----LGVDGACRPCSDAELLLAACTSDFVIHGTIHGVTHDVEL
mMETRN    ELHEDQRAE---MSPQAQGLGVDGA--CRPCSDAELLLAACTSDFVIHGTIHGVAHDTEL
rMETRN    ELIIEDQRAE---MSPQAQGFGVDGA--CRPCSDAELLLTACTSDFVIIGTIIGVVIIDMEL
          **   *                     ****  *    **    *   *    * hMETRNL   QDSAIILRVSRLYRQKSRVFEPVPEG--DGIIWQG--R--VRTLLECGVRPGIIGDFLTGII
mMETRNL   QVSVIYLRVNRLHRQKSRVFQPAPED--SGHWLG--H--VTTLLQCGVRPGHGEFLTGH
rMETRNL   QVSVIHLRVSRLHRQKSRVFQPAPED--SGHWLG--H--VTTLLQCGVRPGHGEFLTGH
hMETRN    QESVITVVAARVLRQTPPLFQAGRSG--D---QGLTS--IRTPLRCGVHPGPGTFLFMGW
mMETRN    QESVITVVARVIRQTLPLFK---EG--SSEGQG--RASIRTLLRCGVRPGPGSFLFMGW
rMETRN    QESVITVVATRVIRQTLPLFQ---EGSSEGRGQA--S--VRTLLRCGVRPGPGSFLFMGW
          * *        *  **  *                    *  *     * *** * hMETRNL   MHFGEARLGCAPRFKDFQRMYRDAQERGLNPCEVGTD
mMETRNL   VHFGEAQLGCAPRFSDFQRMYRKAEEMGINPCEINME
rMETRNL   VHFGEAQLGCAPRFSDFQKMYRKAEERGINPCEINME
hMETRN    SRFGEARLGCAPRFQEFRRAYEAARAAHLHPCEVALH
mMETRN    SRFGEAWLGCAPRFQEFSRVYSAALTTHLNPCEMALD
rMETRN    SRFGEAWLGCAPRFQEFSRVYSAALAAHLNPCEVALD
          **** *** ***** *   *   *   ***
```

Fig. 2

| | | |
|---|---|---|
| Human | 1 | -MRGAARAAWGRAGQPWPRPPAPGPPPPPLPLLLLLLAGLLG-GAGAQYS |
| Cow | 1 | -MRGATRAAGGRAGQLWPRPPAPGPGPPP---LLLLLAVLLG-GAGAQYS |
| Mouse | 1 | -MRGAVWAARRRAGQQWPRSPGPGPGPPPPPPLLLLLLLLLLG-GASAQYS |
| Rat | 1 | -MRGVVWAARRRAGQQWPRSPGPGPGPPPPPPLLLLLLLLLLG-GASAQYS |
| Chicken | 1 | -MRSA--------------PAAGL----LPLLLGLRLLLGG-GAEAQYS |
| Xenopus | 1 | MLRRV---------------------LLSFFMVILMDRGTSQQYG |
| Zebrafish | 1 | -----------------------MLSPFLAYLLSVVLLCR-IARSQYS |

| | | |
|---|---|---|
| Human | 49 | SDRCSWKGSGLTHEAHRKEVEQVYLRCAAGAVEWMYPTGALIVNLRPNTF |
| Cow | 46 | SDLCWKGSGLTHEAHRKEVEQVYLRCSAGTVEWMYPTGALIVNLRPNTF |
| Mouse | 49 | SDLCWKGSGLTREARSKEVEQVYLRCSAGSVEWMYPTGALIVNLRPNTF |
| Rat | 49 | SDLCWKGSGLTREAHSKEVEQVYLRCSAGSVEWMYPTGALIVNLRPNTF |
| Chicken | 30 | SDLCNWKGSGLTHESHKKDVEQVYLRCSEGSIEWMYPTGALIVNLRPNT- |
| Xenopus | 25 | SDMCNWKGSGLTHEGHTKDVEQVYLRCSEGSVEWLYPTGAMIINLRPNTL |
| Zebrafish | 25 | SDQCSWRGSGLTHEGHTRGVEQVYLRCAQGFLEWLYPTGA-IVNLRPNTL |

| | | |
|---|---|---|
| Human | 99 | SPA--RHL-TVCIRSFTDSSGANIYLEKTGELRLLVPDGDRPGRVQCIG |
| Cow | 96 | SPS--RNL-TLCIKPLRGSSGANIYLEKTGELKLLVRDGDLGPGQAPCIG |
| Mouse | 99 | SPA--QNL-TVCIKPFRDSSGANIYLEKTGELRLLVRDIRGEPGQVQCIS |
| Rat | 99 | SPA--QNL-TVCIKPFRDSSGANIYLEKTGELRLLVRDVRGEPGQVQCIS |
| Chicken | 79 | SPASYKHL-TVCIKPFKDSAGANIYLEKTGELKLLVRDGERSPSKVYCIG |
| Xenopus | 75 | TSAY-KHL-TVCIKPFKDSKGANIYSEKTGELKLVVPDGENNPHKVYCIG |
| Zebrafish | 75 | SPA--ASLLSVCIKPSKESSGTHIYLDRLGKLRLLLSEGDQAEGKVHCIN |

| | | |
|---|---|---|
| Human | 146 | LEQGGLFVEATPQQDIGRRTTGFQYELVRRHRASDLHELSAPCRPCSDTE |
| Cow | 143 | FEQGGLFVEATPQQDISRRTTGFQYELTSRRTGPDLHALLAHCRPCSHTE |
| Mouse | 146 | LEQGGLFVEATPQQDISRRTTGFQYELMSGQRGLDLHVLSAPCRPCSDTE |
| Rat | 146 | LEQGGLFVEATPQQDISRRTTGFQYELMSGQRGLDLHVLSAPCRPCSDTE |
| Chicken | 128 | YDQGGLFVEATPQQDISRKITGFQYELMSRGIASDLHTVSAPCRPCSDTE |
| Xenopus | 123 | LDQRGLYIEATPQQDISRKITGFQYELISQRTLSDLHTVSDPCRPCSDTE |
| Zebrafish | 123 | IQDGALFIEAVPQRDISRKITAFQYELVNHRPGADPQSLSAPCQPCTDAE |

| | | |
|---|---|---|
| Human | 196 | VLLAVCTSDFAVRGSIQQVTHEPERQDSAIHLRVSRLYRQKSRVIEPVPE |
| Cow | 193 | VLLAVCTSDFVVRGSIQKVTHEPERQESAIHLNVSRLYRQKSRVIRPAPE |
| Mouse | 196 | VLLAICTSDFVVRGFIEDVTHVPEQQVSVIYLRVNRLHRQKSRVIQPAPE |
| Rat | 196 | VLLAICTSDFVVRGFIEDVTHVPEQQVSVIHLRVSRLHRQKSRVIQPAPE |
| Chicken | 178 | VLLAVCTSDFVIRGSIQDVTNEAEEQESVIHVGVNKLYRQKSKVIQLTGE |
| Xenopus | 173 | VLLAVCISDFVVKSTIGTVINDEELQESLIGVTVDKLYRQKSKII--LPK |
| Zebrafish | 173 | VLLAVCTSDFVARGRILGVSEEDEQ--TSVTVSLSHLYRQKTQVIVSGGG |

| | | |
|---|---|---|
| Human | 246 | GDGH-WCGRVRTLLECGVRPGHGDFLFTGHMHEEARLCIAPREKDFQRM |
| Cow | 243 | GEGGWPGRVSTLLECGVRPGHGEFLFTGHMHEEAWLCIAPREKDFQRM |
| Mouse | 246 | DSGH-WLGHVTTLLQCGVRPGHGEFLFTGHVHEEAQLCIAPRESDFQRM |
| Rat | 246 | DSGH-WLGHVTTLLQCGVRPGHGEFLFTGHVHEEAQLCIAPRESDFQKM |
| Chicken | 228 | S-GN-WRGQIKTLLECGVRPGDGDFLFTGRMHEEARLCIAPREKDFQRM |
| Xenopus | 221 | ENGG-WEGTIRTPRECGVKAGSGSFLFTGRMHEGPRLGCPRYSDFTRI |
| Zebrafish | 221 | RAKR-WTGFVKMSRQCGVKPGDGEFLFTGTVREGEAWLSCAPRYKDFLRV |

| | | |
|---|---|---|
| Human | 295 | YRDAQERGLNPCEVGTD |
| Cow | 293 | YRDAEERGLNPCEMGTE |
| Mouse | 295 | YRKAEEMGINPCEINME |
| Rat | 295 | YRKAEERGINPCEINME |
| Chicken | 276 | YKEAKDKCLNPCEIGPD |
| Xenopus | 270 | YLEAKKQGLNPCEISTD |
| Zebrafish | 270 | YQDARQQGTNPCEHLETD |

Fig. 3

A)
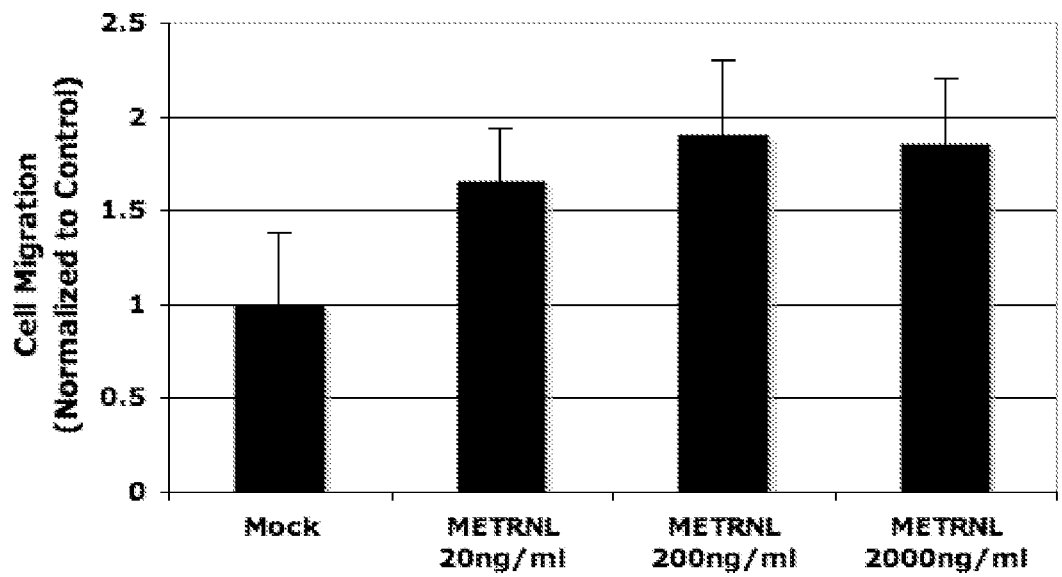
B)
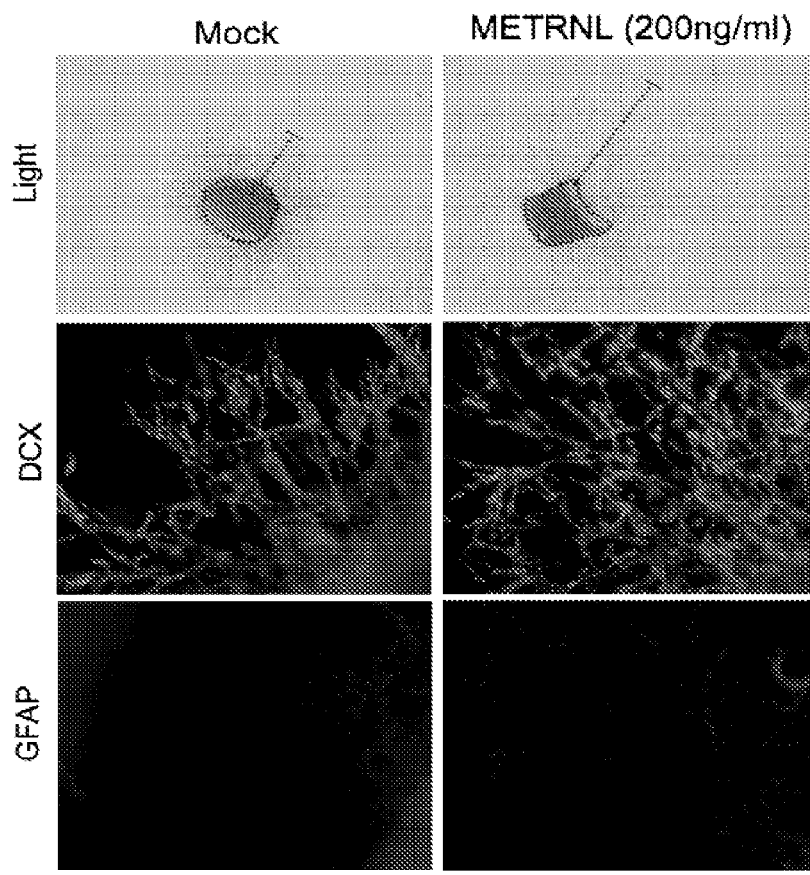
Fig. 8

A)
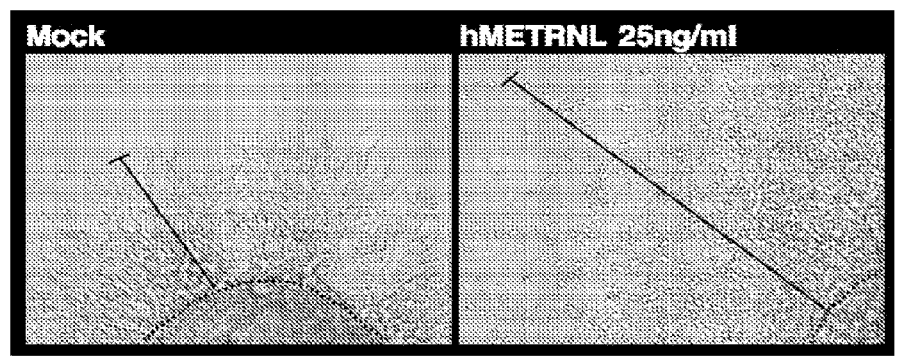
B)
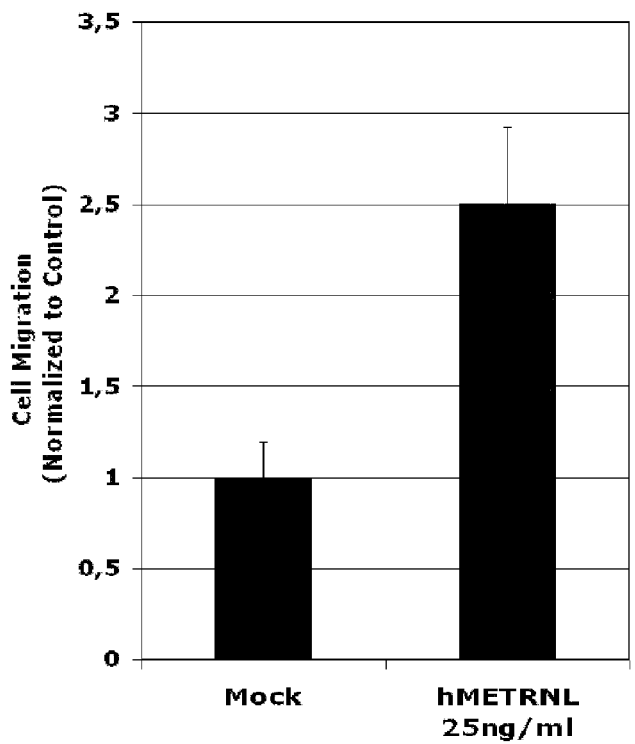
Fig. 10

A)
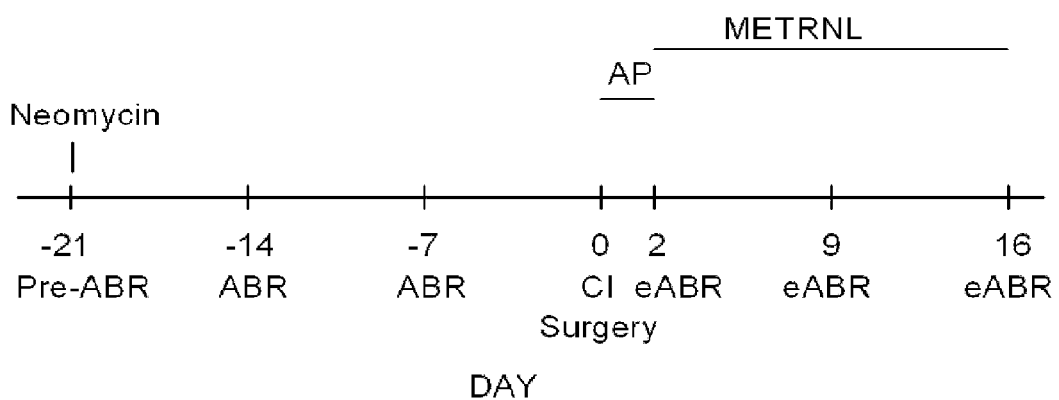
B)
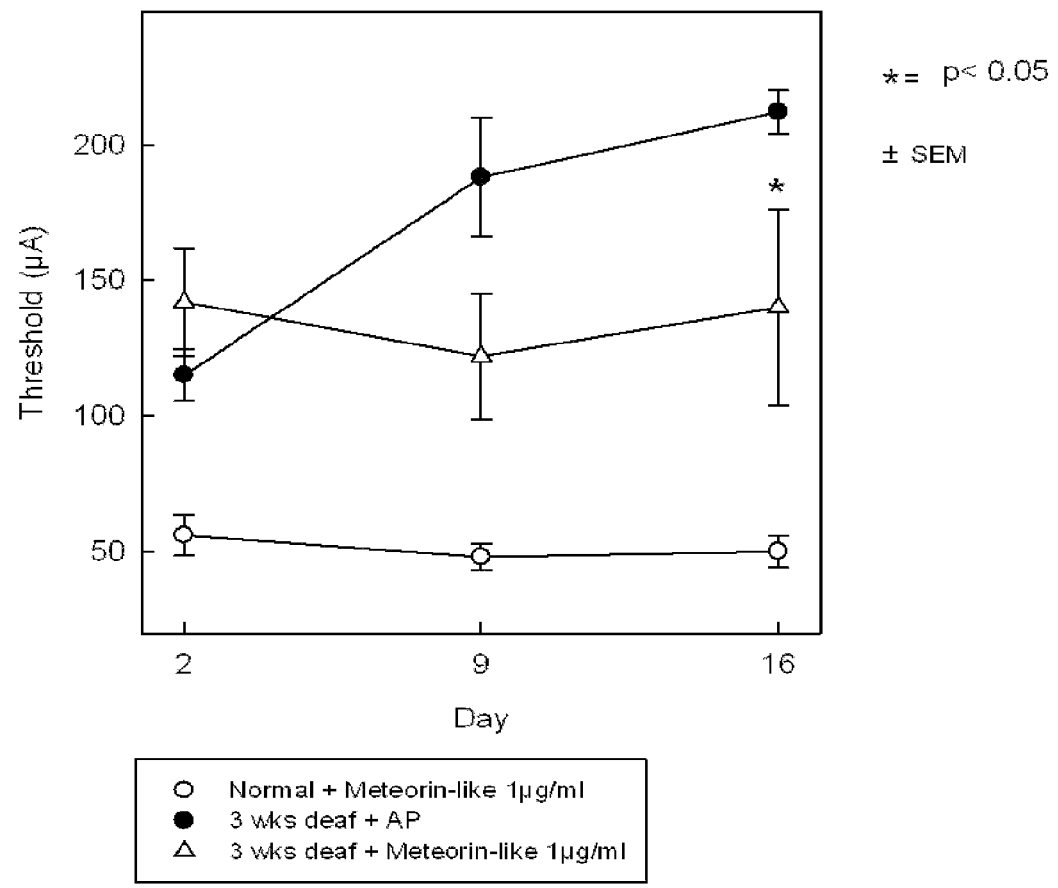
Fig. 11

SEQUENCE LISTING

```
<160> NUMBER OF SEQ ID NOS: 26

<210> SEQ ID NO 1
<211> LENGTH: 1348
<212> TYPE: DNA
<213> ORGANISM: Homo sapiens
<220> FEATURE:
<221> NAME/KEY: CDS
<222> LOCATION: (126)..(1061)

<400> SEQUENCE: 1 gcgggggggcg cgcgacgtga ccacccggac tcgaagcccg ccccgccccc gcccggctcg     60
ccggctccgg ggtctgctcc gggggtcgcg gacgcggggc cgggcggcgg agccggcgcc    120 agagc atg cgg ggc gcg gcg cgg gcg gcc tgg ggg cgc gcg ggg cag ccg    170
      Met Arg Gly Ala Ala Arg Ala Ala Trp Gly Arg Ala Gly Gln Pro
      1               5                   10                  15 tgg ccg cga ccc ccc gcc ccg ggc ccc ccg ccg ccg ctc ccg ctg           218
Trp Pro Arg Pro Pro Ala Pro Gly Pro Pro Pro Pro Leu Pro Leu
                20                  25                  30 ctg ctc ctg ctc ctg gcc ggg ctg ctg ggc ggc gcg ggc gcg cag tac      266
Leu Leu Leu Leu Leu Ala Gly Leu Leu Gly Gly Ala Gly Ala Gln Tyr
            35                  40                  45 tcc agc gac cgg tgc agc tgg aag ggg agc ggg ctg acg cac gag gca      314
Ser Ser Asp Arg Cys Ser Trp Lys Gly Ser Gly Leu Thr His Glu Ala
        50                  55                  60 cac agg aag gag gtg gag cag gtg tat ctg cgc tgt gcg gcg ggt gcc      362
His Arg Lys Glu Val Glu Gln Val Tyr Leu Arg Cys Ala Ala Gly Ala
    65                  70                  75 gtg gag tgg atg tac cca aca ggt gct ctc atc gtt aac ctg cgg ccc      410
Val Glu Trp Met Tyr Pro Thr Gly Ala Leu Ile Val Asn Leu Arg Pro
80                  85                  90                  95 aac acc ttc tcg cct gcc cgg cac ctg acc gtg tgc atc agg tcc ttc      458
Asn Thr Phe Ser Pro Ala Arg His Leu Thr Val Cys Ile Arg Ser Phe
                100                 105                 110 acg gac tcc tcg ggg gcc aat att tat ttg gaa aaa act gga gaa ctg      506
Thr Asp Ser Ser Gly Ala Asn Ile Tyr Leu Glu Lys Thr Gly Glu Leu
            115                 120                 125 aga ctg ctg gta ccg gac ggg gac ggc agg ccc ggc cgg gtg cag tgt      554
Arg Leu Leu Val Pro Asp Gly Asp Gly Arg Pro Gly Arg Val Gln Cys
        130                 135                 140 ttt ggc ctg gag cag ggc ggc ctg ttc gtg gag gcc acg ccg cag cag      602
Phe Gly Leu Glu Gln Gly Gly Leu Phe Val Glu Ala Thr Pro Gln Gln
    145                 150                 155
```

```
gat atc ggc cgg agg acc aca ggc ttc cag tac gag ctg gtt agg agg    650
Asp Ile Gly Arg Arg Thr Thr Gly Phe Gln Tyr Glu Leu Val Arg Arg
160                 165                 170                 175 cac agg gcg tcg gac ctg cac gag ctg tct gcg ccg tgc cgt ccc tgc    698
His Arg Ala Ser Asp Leu His Glu Leu Ser Ala Pro Cys Arg Pro Cys
                180                 185                 190 agt gac acc gag gtg ctc cta gcc gtc tgc acc agc gac ttc gcc gtt    746
Ser Asp Thr Glu Val Leu Leu Ala Val Cys Thr Ser Asp Phe Ala Val
            195                 200                 205 cga ggc tcc atc cag caa gtt acc cac gag cct gag cgg cag gac tca    794
Arg Gly Ser Ile Gln Gln Val Thr His Glu Pro Glu Arg Gln Asp Ser
        210                 215                 220 gcc atc cac ctg cgc gtg agc aga ctc tat cgg cag aaa agc agg gtc    842
Ala Ile His Leu Arg Val Ser Arg Leu Tyr Arg Gln Lys Ser Arg Val
    225                 230                 235 ttc gag ccg gtg ccc gag ggt gac ggc cac tgg cag ggg cgc gtc agg    890
Phe Glu Pro Val Pro Glu Gly Asp Gly His Trp Gln Gly Arg Val Arg
240                 245                 250                 255 acg ctg ctg gag tgt ggc gtg cgg ccg ggg cat ggc gac ttc ctc ttc    938
Thr Leu Leu Glu Cys Gly Val Arg Pro Gly His Gly Asp Phe Leu Phe
                260                 265                 270 act ggc cac atg cac ttc ggg gag gcg cgg ctc ggc tgt gcc cca cgc    986
Thr Gly His Met His Phe Gly Glu Ala Arg Leu Gly Cys Ala Pro Arg
            275                 280                 285 ttc aag gac ttc cag agg atg tac agg gat gcc cag gag agg ggg ctg   1034
Phe Lys Asp Phe Gln Arg Met Tyr Arg Asp Ala Gln Glu Arg Gly Leu
        290                 295                 300 aac cct tgt gag gtt ggc acg gac tga ctccgtgggc cgctgccctt         1081
Asn Pro Cys Glu Val Gly Thr Asp
    305                 310 cctctcctga tgagtcacag gctgcggtgg gcgctgcggt cctggtgggg ccgtgcggtg   1141
agggccgcgc gctgggagcc gcatgccctg ggcccaggcc tgaccctggt accgaagctg   1201
tggacgttct cgcccacactc aaccccatga gcttccagcc aaggatgccc tggccgattg   1261
gaaatgctgt aaaatgcaaa ctaagttatt atattttttt ttggtaaaaa agaaatgtcc   1321
ataggaaaca aaaaaaaaaa aaaaaaa                                      1348

<210> SEQ ID NO 2
<211> LENGTH: 311
<212> TYPE: PRT
<213> ORGANISM: Homo sapiens

<400> SEQUENCE: 2

Met Arg Gly Ala Ala Arg Ala Ala Trp Gly Arg Ala Gly Gln Pro Trp
1               5                   10                  15

Pro Arg Pro Pro Ala Pro Gly Pro Pro Pro Pro Leu Pro Leu Leu
            20                  25                  30

Leu Leu Leu Leu Ala Gly Leu Leu Gly Gly Ala Gly Ala Gln Tyr Ser
        35                  40                  45

Ser Asp Arg Cys Ser Trp Lys Gly Ser Gly Leu Thr His Glu Ala His
    50                  55                  60

Arg Lys Glu Val Glu Gln Val Tyr Leu Arg Cys Ala Ala Gly Ala Val
65                  70                  75                  80

Glu Trp Met Tyr Pro Thr Gly Ala Leu Ile Val Asn Leu Arg Pro Asn
                85                  90                  95

Thr Phe Ser Pro Ala Arg His Leu Thr Val Cys Ile Arg Ser Phe Thr
            100                 105                 110
```

```
Asp Ser Ser Gly Ala Asn Ile Tyr Leu Glu Lys Thr Gly Glu Leu Arg
            115                 120                 125

Leu Leu Val Pro Asp Gly Asp Gly Arg Pro Gly Arg Val Gln Cys Phe
        130                 135                 140

Gly Leu Glu Gln Gly Gly Leu Phe Val Glu Ala Thr Pro Gln Gln Asp
145                 150                 155                 160

Ile Gly Arg Arg Thr Thr Gly Phe Gln Tyr Glu Leu Val Arg Arg His
                165                 170                 175

Arg Ala Ser Asp Leu His Glu Leu Ser Ala Pro Cys Arg Pro Cys Ser
            180                 185                 190

Asp Thr Glu Val Leu Leu Ala Val Cys Thr Ser Asp Phe Ala Val Arg
        195                 200                 205

Gly Ser Ile Gln Gln Val Thr His Glu Pro Glu Arg Gln Asp Ser Ala
    210                 215                 220

Ile His Leu Arg Val Ser Arg Leu Tyr Arg Gln Lys Ser Arg Val Phe
225                 230                 235                 240

Glu Pro Val Pro Glu Gly Asp Gly His Trp Gln Gly Arg Val Arg Thr
                245                 250                 255

Leu Leu Glu Cys Gly Val Arg Pro Gly His Gly Asp Phe Leu Phe Thr
            260                 265                 270

Gly His Met His Phe Gly Glu Ala Arg Leu Gly Cys Ala Pro Arg Phe
        275                 280                 285

Lys Asp Phe Gln Arg Met Tyr Arg Asp Ala Gln Glu Arg Gly Leu Asn
    290                 295                 300

Pro Cys Glu Val Gly Thr Asp
305                 310

<210> SEQ ID NO 3
<211> LENGTH: 2468
<212> TYPE: DNA
<213> ORGANISM: Mus musculus
<220> FEATURE:
<221> NAME/KEY: misc_feature
<222> LOCATION: (1)..(2468)
<223> OTHER INFORMATION: mMTRNL cDNA
<220> FEATURE:
<221> NAME/KEY: CDS
<222> LOCATION: (200)..(1135)

<400> SEQUENCE: 3
agaggttcta ggggcagccg gcgcgcttct ctagttgcag cttgggcggc tcctgtggtg      60
ggcggctagg ggcgagccgg gatgggctat agacgcgcga cgtgatcagt tcgcacgcgg     120
acccacgcct cccatcgctc tgcctcaaga gcctattctg tgggtgcagg cacgcaccgg     180
acgcagaccc ggccggagc atg cgg ggt gcg gtg tgg gcg gcc cgg agg cgc      232
                     Met Arg Gly Ala Val Trp Ala Ala Arg Arg Arg
                       1               5                  10 gcg ggg cag cag tgg cct cgg tcc ccg ggc cct ggg ccg ggt ccg ccc       280
Ala Gly Gln Gln Trp Pro Arg Ser Pro Gly Pro Gly Pro Gly Pro Pro
             15                  20                  25 ccg ccg cca ccg ctg ctg ttg ctg cta cta ctg ctg ctg ggc ggc gcg       328
Pro Pro Pro Pro Leu Leu Leu Leu Leu Leu Leu Leu Leu Gly Gly Ala
         30                  35                  40 agc gct cag tac tcc agc gac ctg tgc agc tgg aag ggg agt ggg ctc       376
Ser Ala Gln Tyr Ser Ser Asp Leu Cys Ser Trp Lys Gly Ser Gly Leu
     45                  50                  55 acc cga gag gca cgc agc aag gag gtg gag cag gtg tac ctg cgc tgc       424
Thr Arg Glu Ala Arg Ser Lys Glu Val Glu Gln Val Tyr Leu Arg Cys
60                  65                  70                  75
```

| | | |
|---|---|---|
| tcc gca ggc tct gtg gag tgg atg tac cca act ggg gcg ctc att gtt<br>Ser Ala Gly Ser Val Glu Trp Met Tyr Pro Thr Gly Ala Leu Ile Val<br>                              80                            85                            90 | | 472 |
| aac cta cgg ccc aac acc ttc tca cct gcc cag aac ttg act gtg tgc<br>Asn Leu Arg Pro Asn Thr Phe Ser Pro Ala Gln Asn Leu Thr Val Cys<br>                   95                              100                         105 | | 520 |
| atc aag cct ttc agg gac tcc tct gga gcc aat att tat ttg gaa aaa<br>Ile Lys Pro Phe Arg Asp Ser Ser Gly Ala Asn Ile Tyr Leu Glu Lys<br>         110                         115                           120 | | 568 |
| act gga gaa cta aga ctg ttg gtg cgg gac atc aga ggt gag cct ggc<br>Thr Gly Glu Leu Arg Leu Leu Val Arg Asp Ile Arg Gly Glu Pro Gly<br>125                         130                         135 | | 616 |
| caa gtg cag tgc ttc agc ctg gag cag gga ggc tta ttt gtg gag gcg<br>Gln Val Gln Cys Phe Ser Leu Glu Gln Gly Gly Leu Phe Val Glu Ala<br>140                         145                         150                         155 | | 664 |
| aca ccc caa cag gac atc agc aga agg acc aca ggc ttc cag tat gag<br>Thr Pro Gln Gln Asp Ile Ser Arg Arg Thr Thr Gly Phe Gln Tyr Glu<br>                              160                            165                         170 | | 712 |
| ctg atg agt ggg cag agg gga ctg gac ctg cac gtg ctg tct gcc ccc<br>Leu Met Ser Gly Gln Arg Gly Leu Asp Leu His Val Leu Ser Ala Pro<br>         175                         180                           185 | | 760 |
| tgt cgg cct tgc agt gac act gag gtc ctc ctt gcc atc tgt acc agt<br>Cys Arg Pro Cys Ser Asp Thr Glu Val Leu Leu Ala Ile Cys Thr Ser<br>               190                            195                         200 | | 808 |
| gac ttt gtt gtc cga ggc ttc att gag gac gtc aca cat gta cca gaa<br>Asp Phe Val Val Arg Gly Phe Ile Glu Asp Val Thr His Val Pro Glu<br>         205                         210                           215 | | 856 |
| cag caa gtg tca gtc atc tac ctg cgg gtg aac agg ctt cac agg cag<br>Gln Gln Val Ser Val Ile Tyr Leu Arg Val Asn Arg Leu His Arg Gln<br>220                         225                         230                         235 | | 904 |
| aag agc agg gtc ttc cag cca gct cct gag gac agt ggc cac tgg ctg<br>Lys Ser Arg Val Phe Gln Pro Ala Pro Glu Asp Ser Gly His Trp Leu<br>                              240                            245                         250 | | 952 |
| ggc cat gtc aca aca ctg ctg cag tgt gga gta cga cca ggg cat ggg<br>Gly His Val Thr Thr Leu Leu Gln Cys Gly Val Arg Pro Gly His Gly<br>               255                            260                         265 | | 1000 |
| gaa ttc ctc ttc act gga cat gtg cac ttt ggg gag gca caa ctt gga<br>Glu Phe Leu Phe Thr Gly His Val His Phe Gly Glu Ala Gln Leu Gly<br>         270                         275                           280 | | 1048 |
| tgt gcc cca cgc ttt agt gac ttt caa agg atg tac agg aaa gca gaa<br>Cys Ala Pro Arg Phe Ser Asp Phe Gln Arg Met Tyr Arg Lys Ala Glu<br>               285                            290                         295 | | 1096 |
| gaa atg ggc ata aac ccc tgt gaa atc aat atg gag tga cttgcagggt<br>Glu Met Gly Ile Asn Pro Cys Glu Ile Asn Met Glu<br>300                         305                         310 | | 1145 |
| gacacagtac tgttgtcctt cagatgagcc atgttttgtg ggctcagtcg ctctatcata | | 1205 |
| tcctgataga gattgcagac tggtggcatg gcccagcct ggtgctagaa ctgggaaggt | | 1265 |
| acatgctgct ctgacccctt aggtcccagc caaggatgcc ctgacccatt ggaactgctg | | 1325 |
| taaaatgcaa actaagttat tatattttt ttgtaaaaga tgccttggtg tgccatttaa | | 1385 |
| tagtgttttt acaaagttat tttcaggcat tggatttggc ctggtatatt ggtgggagct | | 1445 |
| aggttatggt gtgcagtgat ggctatggct cagccttgtt attcctgtga tggaaatgta | | 1505 |
| tggagcaaat actttctaat ttccccttca ttttattttc tattttaaaa gaccatcttt | | 1565 |
| gccgttgaga acctttccag actgtatgga ggctgctccc attccaggga gtaaagacca | | 1625 |
| ggatctgaga ctagtattac atccatctta acccatcaga tgggtacctg cattgaacct | | 1685 |
| tctctgctca gctatggcct gctgtcccaa agaccttttg ctctctggac agttccagat | | 1745 |

```
ggtgctgcct ggcttaaggg acttgttcct cccttgctcc taccaggcca ctgttgcttt    1805
ctgcatctgt cccactgaac cagtcttgtc ctttgaccct gagtttcccc aaatgcacac    1865
atcaaatccc tgaataccaa gggactaacc tacttaatgg cccatttctt cagagggtgt    1925
gggttttccc tatagtaaga aaatctccac aagttgaagc ttaaacagta ggctttcgtt    1985
catacagtcc tggaagccag aatgggtgtg agcagaatca catttcctcc ggagactcca    2045
ggagggactt tatagcttct ggtgactcca ggaatccttg gcttgtaaca atttcactct    2105
ggcattgctt tccctgccat gtgacttctg ccttgtatgt gagggcctgt atcaaatctc    2165
tgtcttggga ggatacagat cattgactta gggcccactc cggtgacctc accttcacct    2225
gaaatttact cgatttccat ttaggtcaga ggcaaaggct acaaaaaata tcaaatccgg    2285
agaaagattc aatggttagg cacttgctac tcttacaaag gacctgtgtt cgattcccat    2345
gttgggaact catgttaggt ggcttaaaat tgcctataac tacaattcca ggggatctag    2405
caacctcttc tcgccacaca caagcacaca cacacacaca cacacacaca cacaattaaa    2465
aac                                                                  2468
```

<210> SEQ ID NO 4
<211> LENGTH: 311
<212> TYPE: PRT
<213> ORGANISM: Mus musculus

<400> SEQUENCE: 4

```
Met Arg Gly Ala Val Trp Ala Ala Arg Arg Ala Gly Gln Gln Trp
1               5                   10                  15

Pro Arg Ser Pro Gly Pro Gly Pro Pro Pro Pro Pro Pro Pro Leu
                20                  25                  30

Leu Leu Leu Leu Leu Leu Leu Leu Gly Gly Ala Ser Ala Gln Tyr Ser
            35                  40                  45

Ser Asp Leu Cys Ser Trp Lys Gly Ser Gly Leu Thr Arg Glu Ala Arg
    50                  55                  60

Ser Lys Glu Val Glu Gln Val Tyr Leu Arg Cys Ser Ala Gly Ser Val
65                  70                  75                  80

Glu Trp Met Tyr Pro Thr Gly Ala Leu Ile Val Asn Leu Arg Pro Asn
                85                  90                  95

Thr Phe Ser Pro Ala Gln Asn Leu Thr Val Cys Ile Lys Pro Phe Arg
            100                 105                 110

Asp Ser Ser Gly Ala Asn Ile Tyr Leu Glu Lys Thr Gly Glu Leu Arg
        115                 120                 125

Leu Leu Val Arg Asp Ile Arg Gly Glu Pro Gly Gln Val Gln Cys Phe
    130                 135                 140

Ser Leu Glu Gln Gly Gly Leu Phe Val Glu Ala Thr Pro Gln Gln Asp
145                 150                 155                 160

Ile Ser Arg Arg Thr Thr Gly Phe Gln Tyr Glu Leu Met Ser Gly Gln
                165                 170                 175

Arg Gly Leu Asp Leu His Val Leu Ser Ala Pro Cys Arg Pro Cys Ser
            180                 185                 190

Asp Thr Glu Val Leu Leu Ala Ile Cys Thr Ser Asp Phe Val Val Arg
        195                 200                 205

Gly Phe Ile Glu Asp Val Thr His Val Pro Glu Gln Gln Val Ser Val
    210                 215                 220

Ile Tyr Leu Arg Val Asn Arg Leu His Arg Gln Lys Ser Arg Val Phe
225                 230                 235                 240
```

```
Gln Pro Ala Pro Glu Asp Ser Gly His Trp Leu Gly His Val Thr Thr
                245                 250                 255

Leu Leu Gln Cys Gly Val Arg Pro Gly His Gly Glu Phe Leu Phe Thr
            260                 265                 270

Gly His Val His Phe Gly Glu Ala Gln Leu Gly Cys Ala Pro Arg Phe
        275                 280                 285

Ser Asp Phe Gln Arg Met Tyr Arg Lys Ala Glu Glu Met Gly Ile Asn
    290                 295                 300

Pro Cys Glu Ile Asn Met Glu
305                 310

<210> SEQ ID NO 5
<211> LENGTH: 1380
<212> TYPE: DNA
<213> ORGANISM: Rattus norvegicus
<220> FEATURE:
<221> NAME/KEY: misc_feature
<222> LOCATION: (1)..(1380)
<223> OTHER INFORMATION: rMTRNL cDNA
<220> FEATURE:
<221> NAME/KEY: CDS
<222> LOCATION: (197)..(1132)

<400> SEQUENCE: 5
ggcagccggc gcgcttctct ggttgcagct tgggcggctg ggcggctcc tatggtgggc      60 ggccaggggc tagacgggat ggcctgtaga cgcgcgacgt gatcagctcg cacgcggacc    120
cacgcctccc gcagcactgc ctcaacagtc tattctgtgg gtgcaggcac gcaccggtct    180
cagaccctgc cggagc atg cgg ggt gtg gtg tgg gcg gcc cgg agg cgc gcg    232
               Met Arg Gly Val Val Trp Ala Ala Arg Arg Arg Ala
                 1               5                  10 ggg cag cag tgg cct cgg tcc ccg ggc cct ggg ccg ggt ccg ccc ccg      280
Gly Gln Gln Trp Pro Arg Ser Pro Gly Pro Gly Pro Gly Pro Pro Pro
             15                  20                  25 ccg cca ccg ctg ctg ttg ctg cta ctg ctg ctg ggc ggc gcg agc           328
Pro Pro Pro Leu Leu Leu Leu Leu Leu Leu Leu Gly Gly Ala Ser
         30                  35                  40 gcg cag tac tcc agc gac ctg tgc agc tgg aag ggg agt ggg ctc acc      376
Ala Gln Tyr Ser Ser Asp Leu Cys Ser Trp Lys Gly Ser Gly Leu Thr
 45                  50                  55                  60 cgg gag gca cac agc aag gag gtg gag cag gtg tac ctg cgc tgc tca      424
Arg Glu Ala His Ser Lys Glu Val Glu Gln Val Tyr Leu Arg Cys Ser
                 65                  70                  75 gca ggc tct gtg gaa tgg atg tac cca acc ggg gcg ctc att gtt aac      472
Ala Gly Ser Val Glu Trp Met Tyr Pro Thr Gly Ala Leu Ile Val Asn
             80                  85                  90 cta cgg ccc aac acc ttc tca cct gcc cag aac ttg act gtg tgc atc      520
Leu Arg Pro Asn Thr Phe Ser Pro Ala Gln Asn Leu Thr Val Cys Ile
         95                 100                 105 aag cct ttc agg gac tcc tct ggg gcc aat att tat ttg gaa aaa act      568
Lys Pro Phe Arg Asp Ser Ser Gly Ala Asn Ile Tyr Leu Glu Lys Thr
    110                 115                 120 gga gaa cta aga ctg ttg gtg cgg gat gtc aga ggc gaa cct ggc caa      616
Gly Glu Leu Arg Leu Leu Val Arg Asp Val Arg Gly Glu Pro Gly Gln
125                 130                 135                 140 gtg cag tgc ttc agc cta gag cag gga ggc tta ttt gtg gag gcc aca      664
Val Gln Cys Phe Ser Leu Glu Gln Gly Gly Leu Phe Val Glu Ala Thr
                145                 150                 155 ccc cag cag gac atc agc aga agg acc aca ggc ttc cag tat gag ctg      712
Pro Gln Gln Asp Ile Ser Arg Arg Thr Thr Gly Phe Gln Tyr Glu Leu
            160                 165                 170
```

```
atg agt ggg cag agg gga ctg gac ctg cac gtg ctc tct gcc ccc tgt    760
Met Ser Gly Gln Arg Gly Leu Asp Leu His Val Leu Ser Ala Pro Cys
    175                 180                 185 cga cct tgc agc gac act gag gtc ctc ctt gcc atc tgc acc agt gac    808
Arg Pro Cys Ser Asp Thr Glu Val Leu Leu Ala Ile Cys Thr Ser Asp
190                 195                 200 ttt gtt gtc cga ggc ttc atc gag gat gtc acc cat gta cca gaa cag    856
Phe Val Val Arg Gly Phe Ile Glu Asp Val Thr His Val Pro Glu Gln
205                 210                 215                 220 caa gtg tca gtc att cac cta cgg gtg agc agg ctc cac agg cag aag    904
Gln Val Ser Val Ile His Leu Arg Val Ser Arg Leu His Arg Gln Lys
                225                 230                 235 agc agg gtc ttc cag cca gct cct gag gac agt ggc cac tgg ctg ggc    952
Ser Arg Val Phe Gln Pro Ala Pro Glu Asp Ser Gly His Trp Leu Gly
            240                 245                 250 cat gtc aca aca ctg ttg cag tgt gga gta cga cca ggg cat gga gaa   1000
His Val Thr Thr Leu Leu Gln Cys Gly Val Arg Pro Gly His Gly Glu
        255                 260                 265 ttc ctc ttc act gga cat gtg cac ttt ggg gag gca caa ctt gga tgt   1048
Phe Leu Phe Thr Gly His Val His Phe Gly Glu Ala Gln Leu Gly Cys
270                 275                 280 gcc cca cgc ttt agt gac ttt caa aag atg tac agg aaa gca gaa gaa   1096
Ala Pro Arg Phe Ser Asp Phe Gln Lys Met Tyr Arg Lys Ala Glu Glu
285                 290                 295                 300 agg ggc ata aac cct tgt gaa ata aat atg gag tga cttgcagggt         1142
Arg Gly Ile Asn Pro Cys Glu Ile Asn Met Glu
                305                 310 gacaccgtac tgctgtcctt cagatgagcc atggctcagt tgctctatca aatcccgata  1202
gagattgcag actggtggca tgagccccgc ctggtgcttg aactgggaag ggaggtacat  1262
gctgctctga cccctaggt cccattcaag gatgccctga cccattggaa atgttgtaaa   1322
atgcaaacta agttattata ttttttttgt aaaagaaaaa aaaaaaaaaa aaaaaaaa    1380

<210> SEQ ID NO 6
<211> LENGTH: 311
<212> TYPE: PRT
<213> ORGANISM: Rattus norvegicus

<400> SEQUENCE: 6

Met Arg Gly Val Val Trp Ala Ala Arg Arg Ala Gly Gln Gln Trp
1               5                   10                  15

Pro Arg Ser Pro Gly Pro Gly Pro Gly Pro Pro Pro Pro Pro Leu
                20                  25                  30

Leu Leu Leu Leu Leu Leu Leu Gly Gly Ala Ser Ala Gln Tyr Ser
            35                  40                  45

Ser Asp Leu Cys Ser Trp Lys Gly Ser Gly Leu Thr Arg Glu Ala His
50                  55                  60

Ser Lys Glu Val Glu Gln Val Tyr Leu Arg Cys Ser Ala Gly Ser Val
65                  70                  75                  80

Glu Trp Met Tyr Pro Thr Gly Ala Leu Ile Val Asn Leu Arg Pro Asn
                85                  90                  95

Thr Phe Ser Pro Ala Gln Asn Leu Thr Val Cys Ile Lys Pro Phe Arg
            100                 105                 110

Asp Ser Ser Gly Ala Asn Ile Tyr Leu Glu Lys Thr Gly Glu Leu Arg
        115                 120                 125

Leu Leu Val Arg Asp Val Arg Gly Glu Pro Gly Gln Val Gln Cys Phe
    130                 135                 140
```

```
Ser Leu Glu Gln Gly Gly Leu Phe Val Glu Ala Thr Pro Gln Gln Asp
145                 150                 155                 160

Ile Ser Arg Arg Thr Thr Gly Phe Gln Tyr Glu Leu Met Ser Gly Gln
                165                 170                 175

Arg Gly Leu Asp Leu His Val Leu Ser Ala Pro Cys Arg Pro Cys Ser
            180                 185                 190

Asp Thr Glu Val Leu Leu Ala Ile Cys Thr Ser Asp Phe Val Val Arg
        195                 200                 205

Gly Phe Ile Glu Asp Val Thr His Val Pro Glu Gln Gln Val Ser Val
    210                 215                 220

Ile His Leu Arg Val Ser Arg Leu His Arg Gln Lys Ser Arg Val Phe
225                 230                 235                 240

Gln Pro Ala Pro Glu Asp Ser Gly His Trp Leu Gly His Val Thr Thr
                245                 250                 255

Leu Leu Gln Cys Gly Val Arg Pro Gly His Gly Glu Phe Leu Phe Thr
            260                 265                 270

Gly His Val His Phe Gly Glu Ala Gln Leu Gly Cys Ala Pro Arg Phe
        275                 280                 285

Ser Asp Phe Gln Lys Met Tyr Arg Lys Ala Glu Glu Arg Gly Ile Asn
    290                 295                 300

Pro Cys Glu Ile Asn Met Glu
305                 310

<210> SEQ ID NO 7
<211> LENGTH: 266
<212> TYPE: PRT
<213> ORGANISM: Homo sapiens
<220> FEATURE:
<221> NAME/KEY: MISC_FEATURE
<222> LOCATION: (1)..(266)
<223> OTHER INFORMATION: hMTRNL mature protein

<400> SEQUENCE: 7

Gln Tyr Ser Ser Asp Arg Cys Ser Trp Lys Gly Ser Gly Leu Thr His
1               5                   10                  15

Glu Ala His Arg Lys Glu Val Glu Gln Val Tyr Leu Arg Cys Ala Ala
                20                  25                  30

Gly Ala Val Glu Trp Met Tyr Pro Thr Gly Ala Leu Ile Val Asn Leu
            35                  40                  45

Arg Pro Asn Thr Phe Ser Pro Ala Arg His Leu Thr Val Cys Ile Arg
        50                  55                  60

Ser Phe Thr Asp Ser Ser Gly Ala Asn Ile Tyr Leu Glu Lys Thr Gly
65                  70                  75                  80

Glu Leu Arg Leu Leu Val Pro Asp Gly Asp Gly Arg Pro Gly Arg Val
                85                  90                  95

Gln Cys Phe Gly Leu Glu Gln Gly Gly Leu Phe Val Glu Ala Thr Pro
            100                 105                 110

Gln Gln Asp Ile Gly Arg Arg Thr Thr Gly Phe Gln Tyr Glu Leu Val
        115                 120                 125

Arg Arg His Arg Ala Ser Asp Leu His Glu Leu Ser Ala Pro Cys Arg
    130                 135                 140

Pro Cys Ser Asp Thr Glu Val Leu Leu Ala Val Cys Thr Ser Asp Phe
145                 150                 155                 160

Ala Val Arg Gly Ser Ile Gln Gln Val Thr His Glu Pro Glu Arg Gln
                165                 170                 175
```

```
Asp Ser Ala Ile His Leu Arg Val Ser Arg Leu Tyr Arg Gln Lys Ser
            180                 185                 190

Arg Val Phe Glu Pro Val Pro Glu Gly Asp Gly His Trp Gln Gly Arg
        195                 200                 205

Val Arg Thr Leu Leu Glu Cys Gly Val Arg Pro Gly His Gly Asp Phe
    210                 215                 220

Leu Phe Thr Gly His Met His Phe Gly Glu Ala Arg Leu Gly Cys Ala
225                 230                 235                 240

Pro Arg Phe Lys Asp Phe Gln Arg Met Tyr Arg Asp Ala Gln Glu Arg
                245                 250                 255

Gly Leu Asn Pro Cys Glu Val Gly Thr Asp
            260                 265

<210> SEQ ID NO 8
<211> LENGTH: 266
<212> TYPE: PRT
<213> ORGANISM: Mus musculus
<220> FEATURE:
<221> NAME/KEY: MISC_FEATURE
<222> LOCATION: (1)..(266)
<223> OTHER INFORMATION: mMTRNL mature protein

<400> SEQUENCE: 8

Gln Tyr Ser Ser Asp Leu Cys Ser Trp Lys Gly Ser Gly Leu Thr Arg
1               5                   10                  15

Glu Ala Arg Ser Lys Glu Val Glu Gln Val Tyr Leu Arg Cys Ser Ala
            20                  25                  30

Gly Ser Val Glu Trp Met Tyr Pro Thr Gly Ala Leu Ile Val Asn Leu
        35                  40                  45

Arg Pro Asn Thr Phe Ser Pro Ala Gln Asn Leu Thr Val Cys Ile Lys
    50                  55                  60

Pro Phe Arg Asp Ser Ser Gly Ala Asn Ile Tyr Leu Glu Lys Thr Gly
65                  70                  75                  80

Glu Leu Arg Leu Leu Val Arg Asp Ile Arg Gly Glu Pro Gly Gln Val
                85                  90                  95

Gln Cys Phe Ser Leu Glu Gln Gly Gly Leu Phe Val Glu Ala Thr Pro
            100                 105                 110

Gln Gln Asp Ile Ser Arg Arg Thr Thr Gly Phe Gln Tyr Glu Leu Met
        115                 120                 125

Ser Gly Gln Arg Gly Leu Asp Leu His Val Leu Ser Ala Pro Cys Arg
    130                 135                 140

Pro Cys Ser Asp Thr Glu Val Leu Leu Ala Ile Cys Thr Ser Asp Phe
145                 150                 155                 160

Val Val Arg Gly Phe Ile Glu Asp Val Thr His Val Pro Glu Gln Gln
                165                 170                 175

Val Ser Val Ile Tyr Leu Arg Val Asn Arg Leu His Arg Gln Lys Ser
            180                 185                 190

Arg Val Phe Gln Pro Ala Pro Glu Asp Ser Gly His Trp Leu Gly His
        195                 200                 205

Val Thr Thr Leu Leu Gln Cys Gly Val Arg Pro Gly His Gly Glu Phe
    210                 215                 220

Leu Phe Thr Gly His Val His Phe Gly Glu Ala Gln Leu Gly Cys Ala
225                 230                 235                 240
```

```
Pro Arg Phe Ser Asp Phe Gln Arg Met Tyr Arg Lys Ala Glu Glu Met
            245                 250                 255

Gly Ile Asn Pro Cys Glu Ile Asn Met Glu
        260                 265

<210> SEQ ID NO 9
<211> LENGTH: 266
<212> TYPE: PRT
<213> ORGANISM: Rattus norvegicus
<220> FEATURE:
<221> NAME/KEY: MISC_FEATURE
<222> LOCATION: (1)..(266)
<223> OTHER INFORMATION: rMTRNL mature protein

<400> SEQUENCE: 9

Gln Tyr Ser Ser Asp Leu Cys Ser Trp Lys Gly Ser Gly Leu Thr Arg
1               5                   10                  15

Glu Ala His Ser Lys Glu Val Glu Gln Val Tyr Leu Arg Cys Ser Ala
            20                  25                  30

Gly Ser Val Glu Trp Met Tyr Pro Thr Gly Ala Leu Ile Val Asn Leu
        35                  40                  45

Arg Pro Asn Thr Phe Ser Pro Ala Gln Asn Leu Thr Val Cys Ile Lys
50                  55                  60

Pro Phe Arg Asp Ser Ser Gly Ala Asn Ile Tyr Leu Glu Lys Thr Gly
65                  70                  75                  80

Glu Leu Arg Leu Leu Val Arg Asp Val Arg Gly Glu Pro Gly Gln Val
                85                  90                  95

Gln Cys Phe Ser Leu Glu Gln Gly Gly Leu Phe Val Glu Ala Thr Pro
            100                 105                 110

Gln Gln Asp Ile Ser Arg Arg Thr Thr Gly Phe Gln Tyr Glu Leu Met
        115                 120                 125

Ser Gly Gln Arg Gly Leu Asp Leu His Val Leu Ser Ala Pro Cys Arg
130                 135                 140

Pro Cys Ser Asp Thr Glu Val Leu Leu Ala Ile Cys Thr Ser Asp Phe
145                 150                 155                 160

Val Val Arg Gly Phe Ile Glu Asp Val Thr His Val Pro Glu Gln Gln
                165                 170                 175

Val Ser Val Ile His Leu Arg Val Ser Arg Leu His Arg Gln Lys Ser
            180                 185                 190

Arg Val Phe Gln Pro Ala Pro Glu Asp Ser Gly His Trp Leu Gly His
        195                 200                 205

Val Thr Thr Leu Leu Gln Cys Gly Val Arg Pro Gly His Gly Glu Phe
210                 215                 220

Leu Phe Thr Gly His Val His Phe Gly Glu Ala Gln Leu Gly Cys Ala
225                 230                 235                 240

Pro Arg Phe Ser Asp Phe Gln Lys Met Tyr Arg Lys Ala Glu Glu Arg
                245                 250                 255

Gly Ile Asn Pro Cys Glu Ile Asn Met Glu
            260                 265

<210> SEQ ID NO 10
<211> LENGTH: 255
<212> TYPE: PRT
<213> ORGANISM: Homo sapiens
<220> FEATURE:
<221> NAME/KEY: MISC_FEATURE
<222> LOCATION: (1)..(255)
<223> OTHER INFORMATION: hMTRNL core fragment
```

```
<400> SEQUENCE: 10

Cys Ser Trp Lys Gly Ser Gly Leu Thr His Glu Ala His Arg Lys Glu
1               5                   10                  15

Val Glu Gln Val Tyr Leu Arg Cys Ala Ala Gly Ala Val Glu Trp Met
            20                  25                  30

Tyr Pro Thr Gly Ala Leu Ile Val Asn Leu Arg Pro Asn Thr Phe Ser
            35                  40                  45

Pro Ala Arg His Leu Thr Val Cys Ile Arg Ser Phe Thr Asp Ser Ser
    50                  55                  60

Gly Ala Asn Ile Tyr Leu Glu Lys Thr Gly Glu Leu Arg Leu Leu Val
65                  70                  75                  80

Pro Asp Gly Asp Gly Arg Pro Gly Arg Val Gln Cys Phe Gly Leu Glu
                85                  90                  95

Gln Gly Gly Leu Phe Val Glu Ala Thr Pro Gln Asp Ile Gly Arg
            100                 105                 110

Arg Thr Thr Gly Phe Gln Tyr Glu Leu Val Arg Arg His Arg Ala Ser
            115                 120                 125

Asp Leu His Glu Leu Ser Ala Pro Cys Arg Pro Cys Ser Asp Thr Glu
    130                 135                 140

Val Leu Leu Ala Val Cys Thr Ser Asp Phe Ala Val Arg Gly Ser Ile
145                 150                 155                 160

Gln Gln Val Thr His Glu Pro Glu Arg Gln Asp Ser Ala Ile His Leu
                165                 170                 175

Arg Val Ser Arg Leu Tyr Arg Gln Lys Ser Arg Val Phe Glu Pro Val
            180                 185                 190

Pro Glu Gly Asp Gly His Trp Gln Gly Arg Val Arg Thr Leu Leu Glu
            195                 200                 205

Cys Gly Val Arg Pro Gly His Gly Asp Phe Leu Phe Thr Gly His Met
    210                 215                 220

His Phe Gly Glu Ala Arg Leu Gly Cys Ala Pro Arg Phe Lys Asp Phe
225                 230                 235                 240

Gln Arg Met Tyr Arg Asp Ala Gln Glu Arg Gly Leu Asn Pro Cys
                245                 250                 255

<210> SEQ ID NO 11
<211> LENGTH: 255
<212> TYPE: PRT
<213> ORGANISM: Mus musculus
<220> FEATURE:
<221> NAME/KEY: MISC_FEATURE
<222> LOCATION: (1)..(255)
<223> OTHER INFORMATION: mMTRNL core fragment

<400> SEQUENCE: 11

Cys Ser Trp Lys Gly Ser Gly Leu Thr Arg Glu Ala Arg Ser Lys Glu
1               5                   10                  15

Val Glu Gln Val Tyr Leu Arg Cys Ser Ala Gly Ser Val Glu Trp Met
            20                  25                  30

Tyr Pro Thr Gly Ala Leu Ile Val Asn Leu Arg Pro Asn Thr Phe Ser
            35                  40                  45

Pro Ala Gln Asn Leu Thr Val Cys Ile Lys Pro Phe Arg Asp Ser Ser
    50                  55                  60

Gly Ala Asn Ile Tyr Leu Glu Lys Thr Gly Glu Leu Arg Leu Leu Val
65                  70                  75                  80

Arg Asp Ile Arg Gly Glu Pro Gly Gln Val Gln Cys Phe Ser Leu Glu
                85                  90                  95
```

```
Gln Gly Gly Leu Phe Val Glu Ala Thr Pro Gln Gln Asp Ile Ser Arg
            100                 105                 110
Arg Thr Thr Gly Phe Gln Tyr Glu Leu Met Ser Gly Gln Arg Gly Leu
        115                 120                 125
Asp Leu His Val Leu Ser Ala Pro Cys Arg Pro Cys Ser Asp Thr Glu
    130                 135                 140
Val Leu Leu Ala Ile Cys Thr Ser Asp Phe Val Val Arg Gly Phe Ile
145                 150                 155                 160
Glu Asp Val Thr His Val Pro Glu Gln Gln Val Ser Val Ile Tyr Leu
                165                 170                 175
Arg Val Asn Arg Leu His Arg Gln Lys Ser Arg Val Phe Gln Pro Ala
            180                 185                 190
Pro Glu Asp Ser Gly His Trp Leu Gly His Val Thr Thr Leu Leu Gln
        195                 200                 205
Cys Gly Val Arg Pro Gly His Gly Glu Phe Leu Phe Thr Gly His Val
    210                 215                 220
His Phe Gly Glu Ala Gln Leu Gly Cys Ala Pro Arg Phe Ser Asp Phe
225                 230                 235                 240
Gln Arg Met Tyr Arg Lys Ala Glu Glu Met Gly Ile Asn Pro Cys
                245                 250                 255

<210> SEQ ID NO 12
<211> LENGTH: 255
<212> TYPE: PRT
<213> ORGANISM: Rattus norvegicus
<220> FEATURE:
<221> NAME/KEY: MISC_FEATURE
<222> LOCATION: (1)..(255)
<223> OTHER INFORMATION: rMTRNL core fragment

<400> SEQUENCE: 12

Cys Ser Trp Lys Gly Ser Gly Leu Thr Arg Glu Ala His Ser Lys Glu
1               5                   10                  15
Val Glu Gln Val Tyr Leu Arg Cys Ser Ala Gly Ser Val Glu Trp Met
            20                  25                  30
Tyr Pro Thr Gly Ala Leu Ile Val Asn Leu Arg Pro Asn Thr Phe Ser
        35                  40                  45
Pro Ala Gln Asn Leu Thr Val Cys Ile Lys Pro Phe Arg Asp Ser Ser
    50                  55                  60
Gly Ala Asn Ile Tyr Leu Glu Lys Thr Gly Glu Leu Arg Leu Leu Val
65                  70                  75                  80
Arg Asp Val Arg Gly Glu Pro Gly Gln Val Gln Cys Phe Ser Leu Glu
                85                  90                  95
Gln Gly Gly Leu Phe Val Glu Ala Thr Pro Gln Gln Asp Ile Ser Arg
            100                 105                 110
Arg Thr Thr Gly Phe Gln Tyr Glu Leu Met Ser Gly Gln Arg Gly Leu
        115                 120                 125
Asp Leu His Val Leu Ser Ala Pro Cys Arg Pro Cys Ser Asp Thr Glu
    130                 135                 140
Val Leu Leu Ala Ile Cys Thr Ser Asp Phe Val Val Arg Gly Phe Ile
145                 150                 155                 160
Glu Asp Val Thr His Val Pro Glu Gln Gln Val Ser Val Ile His Leu
                165                 170                 175
Arg Val Ser Arg Leu His Arg Gln Lys Ser Arg Val Phe Gln Pro Ala
            180                 185                 190
```

```
Pro Glu Asp Ser Gly His Trp Leu Gly His Val Thr Thr Leu Leu Gln
            195                 200                 205

Cys Gly Val Arg Pro Gly His Gly Glu Phe Leu Phe Thr Gly His Val
210                 215                 220

His Phe Gly Glu Ala Gln Leu Gly Cys Ala Pro Arg Phe Ser Asp Phe
225                 230                 235                 240

Gln Lys Met Tyr Arg Lys Ala Glu Glu Arg Gly Ile Asn Pro Cys
            245                 250                 255

<210> SEQ ID NO 13
<211> LENGTH: 936
<212> TYPE: DNA
<213> ORGANISM: Homo sapiens
<220> FEATURE:
<221> NAME/KEY: misc_feature
<222> LOCATION: (1)..(936)
<223> OTHER INFORMATION: hMTRNL open reading frame

<400> SEQUENCE: 13
atgcggggcg cggcgcgggc ggcctggggg cgcgcggggc agccgtggcc gcgaccccccc      60 gccccgggcc cgccccgcc gccgctcccg ctgctgctcc tgctcctggc cgggctgctg     120
ggcggcgcgg gcgcgcagta ctccagcgac cggtgcagct ggaaggggag cgggctgacg     180
cacgaggcac acaggaagga ggtggagcag gtgtatctgc gctgtgcggc gggtgccgtg     240
gagtggatgt acccaacagg tgctctcatc gttaacctgc ggcccaacac cttctcgcct     300
gcccggcacc tgaccgtgtg catcaggtcc ttcacggact cctcgggggc caatatttat     360
ttggaaaaaa ctggagaact gagactgctg gtaccggacg gggacggcag gcccggccgg     420
gtgcagtgtt ttggcctgga gcagggcggc ctgttcgtgg aggccacgcc gcagcaggat     480
atcggccgga ggaccacagg cttccagtac gagctggtta ggaggcacag ggcgtcggac     540
ctgcacgagc tgtctgcgcc gtgccgtccc tgcagtgaca ccgaggtgct cctagccgtc     600
tgcaccagcg acttcgccgt tcgaggctcc atccagcaag ttacccacga gcctgagcgg     660
caggactcag ccatccacct gcgcgtgagc agactctatc ggcagaaaag cagggtcttc     720
gagccggtgc ccgagggtga cggccactgg caggggcgcg tcaggacgct gctggagtgt     780
ggcgtgcggc cggggcatgg cgacttcctc ttcactggcc acatgcactt cggggaggcg     840
cggctcggct gtgccccacg cttcaaggac ttccagagga tgtacaggga tgcccaggag     900 aggggggctga acccttgtga ggttggcacg gactga                              936

<210> SEQ ID NO 14
<211> LENGTH: 936
<212> TYPE: DNA
<213> ORGANISM: Mus musculus
<220> FEATURE:
<221> NAME/KEY: misc_feature
<222> LOCATION: (1)..(936)
<223> OTHER INFORMATION: mMTRNL open reading frame

<400> SEQUENCE: 14
atgcggggtg cggtgtgggc ggcccggagg cgcgcggggc agcagtggcc tcggtccccg      60
ggccctgggc cgggtccgcc cccgccgcca ccgctgctgt tgctgctact actgctgctg     120
ggcggcgcga gcgctcagta ctccagcgac ctgtgcagct ggaaggggag tgggctcacc     180
cgagaggcac gcagcaagga ggtggagcag gtgtacctgc gctgctccgc aggctctgtg     240
gagtggatgt acccaactgg ggcgctcatt gttaacctac ggcccaacac cttctcacct     300
```

```
gcccagaact tgactgtgtg catcaagcct ttcagggact cctctggagc caatatttat    360
ttggaaaaaa ctggagaact aagactgttg gtgcgggaca tcagaggtga gcctggccaa    420
gtgcagtgct tcagcctgga gcagggaggc ttatttgtgg aggcgacacc ccaacaggac    480
atcagcagaa ggaccacagg cttccagtat gagctgatga gtgggcagag gggactggac    540
ctgcacgtgc tgtctgcccc ctgtcggcct tgcagtgaca ctgaggtcct ccttgccatc    600
tgtaccagtg actttgttgt ccgaggcttc attgaggacg tcacacatgt accagaacag    660
caagtgtcag tcatctacct gcgggtgaac aggcttcaca ggcagaagag cagggtcttc    720
cagccagctc ctgaggacag tggccactgg ctgggccatg tcacaacact gctgcagtgt    780
ggagtacgac cagggcatgg ggaattcctc ttcactggac atgtgcactt ggggaggca    840 caacttggat gtgccccacg ctttagtgac tttcaaagga tgtacaggaa agcagaagaa    900
atgggcataa acccctgtga aatcaatatg gagtga                              936
```

```
<210> SEQ ID NO 15
<211> LENGTH: 936
<212> TYPE: DNA
<213> ORGANISM: Rattus norvegicus
<220> FEATURE:
<221> NAME/KEY: misc_feature
<222> LOCATION: (1)..(936)
<223> OTHER INFORMATION: rMTRNL open reading frame

<400> SEQUENCE: 15
```

```
atgcggggtg tggtgtgggc ggcccggagg cgcgcggggc agcagtggcc tcggtccccg    60
ggccctgggc cgggtccgcc ccgccgcca ccgctgctgt tgctgctact gctgctgctg    120
ggcggcgcga gcgcgcagta ctccagcgac ctgtgcagct ggaaggggag tgggctcacc    180
cgggaggcac acagcaagga ggtggagcag gtgtacctgc gctgctcagc aggctctgtg    240
gaatggatgt acccaaccgg ggcgctcatt gttaacctac ggcccaacac cttctcacct    300
gcccagaact tgactgtgtg catcaagcct ttcagggact cctctgggc caatatttat    360 ttggaaaaaa ctggagaact aagactgttg gtgcgggatg tcagaggcga acctggccaa    420
gtgcagtgct tcagcctaga gcagggaggc ttatttgtgg aggccacacc ccagcaggac    480
atcagcagaa ggaccacagg cttccagtat gagctgatga gtgggcagag gggactggac    540
ctgcacgtgc tctctgcccc ctgtcgacct tgcagcgaca ctgaggtcct ccttgccatc    600
tgcaccagtg actttgttgt ccgaggcttc atcgaggatg tcacccatgt accagaacag    660
caagtgtcag tcattcacct acgggtgagc aggctccaca ggcagaagag cagggtcttc    720
cagccagctc ctgaggacag tggccactgg ctgggccatg tcacaacact gttgcagtgt    780
ggagtacgac cagggcatgg agaattcctc ttcactggac atgtgcactt ggggaggca    840 caacttggat gtgccccacg ctttagtgac tttcaaaga tgtacaggaa agcagaagaa    900 agggcataa accttgtga aataaatatg gagtga                                936
```

```
<210> SEQ ID NO 16
<211> LENGTH: 801
<212> TYPE: DNA
<213> ORGANISM: Homo sapiens
<220> FEATURE:
<221> NAME/KEY: misc_feature
<222> LOCATION: (1)..(801)
<223> OTHER INFORMATION: hMTRNL mature CDS
```

<400> SEQUENCE: 16

```
cagtactcca gcgaccggtg cagctggaag gggagcgggc tgacgcacga ggcacacagg      60
aaggaggtgg agcaggtgta tctgcgctgt gcggcgggtg ccgtggagtg gatgtaccca     120
acaggtgctc tcatcgttaa cctgcggccc aacaccttct cgcctgcccg gcacctgacc     180
gtgtgcatca ggtccttcac ggactcctcg ggggccaata tttatttgga aaaaactgga     240
gaactgagac tgctggtacc ggacggggac ggcaggcccg gccgggtgca gtgttttggc     300
ctggagcagg gcggcctgtt cgtggaggcc acgccgcagc aggatatcgg ccggaggacc     360
acaggcttcc agtacgagct ggttaggagg cacagggcgt cggacctgca cgagctgtct     420
gcgccgtgcc gtccctgcag tgacaccgag gtgctcctag ccgtctgcac cagcgacttc     480
gccgttcgag gctccatcca gcaagttacc cacgagcctg agcggcagga ctcagccatc     540
cacctgcgcg tgagcagact ctatcggcag aaaagcaggg tcttcgagcc ggtgcccgag     600
ggtgacggcc actggcaggg gcgcgtcagg acgctgctgg agtgtggcgt gcggccgggg     660
catggcgact tcctcttcac tggccacatg cacttcgggg aggcgcggct cggctgtgcc     720
ccacgcttca aggacttcca gaggatgtac agggatgccc aggagagggg gctgaaccct     780
tgtgaggttg gcacggactg a                                               801
```

<210> SEQ ID NO 17
<211> LENGTH: 801
<212> TYPE: DNA
<213> ORGANISM: Mus musculus
<220> FEATURE:
<221> NAME/KEY: misc_feature
<222> LOCATION: (1)..(801)
<223> OTHER INFORMATION: mMTRNL mature CDS

<400> SEQUENCE: 17

```
cagtactcca gcgacctgtg cagctggaag gggagtgggc tcacccgaga ggcacgcagc      60
aaggaggtgg agcaggtgta cctgcgctgc tccgcaggct ctgtggagtg gatgtaccca     120
actggggcgc tcattgttaa cctacggccc aacaccttct cacctgccca gaacttgact     180
gtgtgcatca agccttttcag ggactcctct ggagccaata tttatttgga aaaaactgga     240
gaactaagac tgttggtgcg ggacatcaga ggtgagcctg gccaagtgca gtgcttcagc     300
ctggagcagg gaggcttatt tgtggaggcg acacccaac aggacatcag cagaaggacc      360
acaggcttcc agtatgagct gatgagtggg cagagggac tggacctgca cgtgctgtct     420
gcccccctgtc ggccttgcag tgacactgag gtcctccttg ccatctgtac cagtgacttt     480
gttgtccgag gcttcattga ggacgtcaca catgtaccag aacagcaagt gtcagtcatc     540
tacctgcggg tgaacaggct tcacaggcag aagagcaggg tcttccagcc agctcctgag     600
gacagtggcc actggctggg ccatgtcaca acactgctgc agtgtggagt acgaccaggg     660
catggggaat tcctcttcac tggacatgtg cactttgggg aggcacaact tggatgtgcc     720
ccacgcttta gtgactttca aggatgtac aggaaagcag aagaaatggg cataaacccc      780
tgtgaaatca atatggagtg a                                               801
```

<210> SEQ ID NO 18
<211> LENGTH: 801
<212> TYPE: DNA
<213> ORGANISM: Rattus norvegicus
<220> FEATURE:
<221> NAME/KEY: misc_feature
<222> LOCATION: (1)..(801)
<223> OTHER INFORMATION: rMTRNL mature CDS

<400> SEQUENCE: 18

```
cagtactcca gcgacctgtg cagctggaag gggagtgggc tcacccggga ggcacacagc     60
aaggaggtgg agcaggtgta cctgcgctgc tcagcaggct ctgtggaatg gatgtaccca    120
accggggcgc tcattgttaa cctacggccc aacaccttct cacctgccca gaacttgact    180
gtgtgcatca agcctttcag ggactcctct ggggccaata tttatttgga aaaaactgga    240
gaactaagac tgttggtgcg ggatgtcaga ggcgaacctg ccaagtgca gtgcttcagc     300
ctagagcagg gaggcttatt tgtggaggcc acaccccagc aggacatcag cagaaggacc    360
acaggcttcc agtatgagct gatgagtggg cagaggggac tggacctgca cgtgctctct    420
gcccctgtc gaccttgcag cgacactgag gtcctccttg ccatctgcac cagtgacttt     480
gttgtccgag gcttcatcga ggatgtcacc catgtaccag aacagcaagt gtcagtcatt    540
cacctacggg tgagcaggct ccacaggcag aagagcaggg tcttccagcc agctcctgag    600
gacagtggcc actggctggg ccatgtcaca acactgttgc agtgtggagt acgaccaggg    660
catggagaat tcctcttcac tggacatgtg cactttgggg aggcacaact tggatgtgcc    720
ccacgcttta gtgactttca aaagatgtac aggaaagcag aagaagggg cataaaccct     780
tgtgaaataa atatggagtg a                                               801
```

<210> SEQ ID NO 19
<211> LENGTH: 309
<212> TYPE: PRT
<213> ORGANISM: Bos taurus
<220> FEATURE:
<221> NAME/KEY: SIGNAL
<222> LOCATION: (1)..(42)
<220> FEATURE:
<221> NAME/KEY: mat_peptide
<222> LOCATION: (43)..(309)

<400> SEQUENCE: 19

```
Met Arg Gly Ala Thr Arg Ala Ala Gly Gly Arg Ala Gly Gln Leu Trp
    -40                 -35                 -30

Pro Arg Pro Pro Ala Pro Gly Pro Gly Pro Pro Pro Leu Leu Leu Leu
    -25                 -20                 -15

Leu Ala Val Leu Leu Gly Gly Ala Gly Ala Gln Tyr Ser Ser Asp Leu
-10                  -5              -1   1                   5

Cys Ser Trp Lys Gly Ser Gly Leu Thr His Glu Ala His Arg Lys Glu
                 10                  15                  20

Val Glu Gln Val Tyr Leu Arg Cys Ser Ala Gly Thr Val Glu Trp Met
             25                  30                  35

Tyr Pro Thr Gly Ala Leu Ile Val Asn Leu Arg Pro Asn Thr Phe Ser
         40                  45                  50

Pro Ser Arg Asn Leu Thr Leu Cys Ile Lys Pro Leu Arg Gly Ser Ser
55                  60                  65                  70

Gly Ala Asn Ile Tyr Leu Glu Lys Thr Gly Glu Leu Lys Leu Leu Val
                 75                  80                  85

Arg Asp Gly Asp Leu Gly Pro Gly Gln Ala Pro Cys Phe Gly Phe Glu
             90                  95                 100

Gln Gly Gly Leu Phe Val Glu Ala Thr Pro Gln Asp Ile Ser Arg
         105                 110                 115

Arg Thr Thr Gly Phe Gln Tyr Glu Leu Thr Ser Arg Arg Thr Gly Pro
     120                 125                 130

Asp Leu His Ala Leu Leu Ala Pro Cys Arg Pro Cys Ser His Thr Glu
135                 140                 145                 150
```

```
Val Leu Leu Ala Val Cys Thr Ser Asp Phe Val Arg Gly Ser Ile
            155                 160                 165

Gln Lys Val Thr His Glu Pro Glu Arg Gln Glu Ser Ala Ile His Leu
        170                 175                 180

Asn Val Ser Arg Leu Tyr Arg Gln Lys Ser Arg Val Phe Arg Pro Ala
            185                 190                 195

Pro Glu Gly Glu Gly Gly Trp Arg Gly Val Ser Thr Leu Leu
        200                 205                 210

Glu Cys Gly Val Arg Pro Gly His Gly Glu Phe Leu Phe Thr Gly His
215                 220                 225                 230

Met His Phe Gly Glu Ala Trp Leu Gly Cys Ala Pro Arg Phe Lys Asp
                235                 240                 245

Phe Gln Arg Met Tyr Arg Asp Ala Glu Glu Arg Gly Leu Asn Pro Cys
            250                 255                 260

Glu Met Gly Thr Glu
            265

<210> SEQ ID NO 20
<211> LENGTH: 292
<212> TYPE: PRT
<213> ORGANISM: Gallus gallus
<220> FEATURE:
<221> NAME/KEY: SIGNAL
<222> LOCATION: (1)..(26)
<220> FEATURE:
<221> NAME/KEY: mat_peptide
<222> LOCATION: (27)..(292)

<400> SEQUENCE: 20

Met Arg Ser Ala Pro Ala Ala Gly Leu Leu Pro Leu Leu Leu Gly Leu
    -25                 -20                 -15

Arg Leu Leu Leu Gly Gly Gly Ala Glu Ala Gln Tyr Ser Ser Asp Leu
-10                  -5                  -1   1               5

Cys Asn Trp Lys Gly Ser Gly Leu Thr His Glu Ser His Lys Lys Asp
                10                  15                  20

Val Glu Gln Val Tyr Leu Arg Cys Ser Glu Gly Ser Ile Glu Trp Met
            25                  30                  35

Tyr Pro Thr Gly Ala Leu Ile Val Asn Leu Arg Pro Asn Thr Ser Pro
        40                  45                  50

Ala Ser Tyr Lys His Leu Thr Val Cys Ile Lys Pro Phe Lys Asp Ser
55                  60                  65                  70

Ala Gly Ala Asn Ile Tyr Leu Glu Lys Thr Gly Glu Leu Lys Leu Leu
                75                  80                  85

Val Arg Asp Gly Glu Arg Ser Pro Ser Lys Val Tyr Cys Phe Gly Tyr
            90                  95                  100

Asp Gln Gly Gly Leu Phe Val Glu Ala Thr Pro Gln Gln Asp Ile Ser
        105                 110                 115

Arg Lys Ile Thr Gly Phe Gln Tyr Glu Leu Met Ser Arg Gly Ile Ala
    120                 125                 130

Ser Asp Leu His Thr Val Ser Ala Pro Cys Arg Pro Cys Ser Asp Thr
135                 140                 145                 150

Glu Val Leu Leu Ala Val Cys Thr Ser Asp Phe Val Ile Arg Gly Ser
                155                 160                 165

Ile Gln Asp Val Thr Asn Glu Ala Glu Glu Gln Glu Ser Val Ile His
            170                 175                 180

Val Gly Val Asn Lys Leu Tyr Arg Gln Lys Ser Lys Val Phe Gln Leu
        185                 190                 195
```

```
Thr Gly Glu Ser Gly Asn Trp Arg Gly Gln Ile Lys Thr Leu Leu Glu
    200                 205                 210

Cys Gly Val Arg Pro Gly Asp Gly Asp Phe Leu Phe Thr Gly Arg Met
215                 220                 225                 230

His Phe Gly Glu Ala Arg Leu Gly Cys Ala Pro Arg Phe Lys Asp Phe
                235                 240                 245

Gln Arg Met Tyr Lys Glu Ala Lys Asp Lys Gly Leu Asn Pro Cys Glu
            250                 255                 260

Ile Gly Pro Asp
        265

<210> SEQ ID NO 21
<211> LENGTH: 286
<212> TYPE: PRT
<213> ORGANISM: Xenopus laevis
<220> FEATURE:
<221> NAME/KEY: SIGNAL
<222> LOCATION: (1)..(21)
<220> FEATURE:
<221> NAME/KEY: mat_peptide
<222> LOCATION: (22)..(286)

<400> SEQUENCE: 21

Met Leu Arg Arg Val Leu Leu Ser Phe Phe Met Val Ile Leu Met Asp
    -20                 -15                 -10

Arg Gly Thr Ser Gln Gln Tyr Ser Asp Met Cys Asn Trp Lys Gly
-5                  -1  1               5                   10

Ser Gly Leu Thr His Glu Gly His Thr Lys Asp Val Glu Gln Val Tyr
            15                  20                  25

Leu Arg Cys Ser Glu Gly Ser Val Glu Trp Leu Tyr Pro Thr Gly Ala
            30                  35                  40

Met Ile Ile Asn Leu Arg Pro Asn Thr Leu Thr Ser Ala Tyr Lys His
        45                  50                  55

Leu Thr Val Cys Ile Lys Pro Phe Lys Asp Ser Lys Gly Ala Asn Ile
60                  65                  70                  75

Tyr Ser Glu Lys Thr Gly Glu Leu Lys Leu Val Val Pro Asp Gly Glu
                80                  85                  90

Asn Asn Pro His Lys Val Tyr Cys Phe Gly Leu Asp Gln Arg Gly Leu
            95                  100                 105

Tyr Ile Glu Ala Thr Pro Gln Gln Asp Ile Ser Arg Lys Ile Thr Gly
        110                 115                 120

Phe Gln Tyr Glu Leu Ile Ser Gln Arg Thr Leu Ser Asp Leu His Thr
    125                 130                 135

Val Ser Asp Pro Cys Arg Pro Cys Ser Asp Thr Glu Val Leu Leu Ala
140                 145                 150                 155

Val Cys Ile Ser Asp Phe Val Val Lys Gly Thr Ile Gly Thr Val Thr
                160                 165                 170

Asn Asp Glu Glu Leu Gln Glu Ser Leu Ile Gly Val Thr Val Asp Lys
            175                 180                 185

Leu Tyr Arg Gln Lys Ser Lys Ile Phe Leu Pro Lys Leu Asn Gly Gly
        190                 195                 200

Trp Glu Gly Thr Ile Arg Thr Pro Arg Glu Cys Gly Val Lys Ala Gly
    205                 210                 215

Ser Gly Ser Phe Leu Phe Thr Gly Arg Met His Phe Gly Glu Pro Arg
220                 225                 230                 235
```

```
Leu Gly Cys Thr Pro Arg Tyr Ser Asp Phe Thr Arg Ile Tyr Leu Glu
            240                 245                 250

Ala Lys Lys Gln Gly Leu Asn Pro Cys Glu Ile Ser Thr Asp
        255                 260                 265

<210> SEQ ID NO 22
<211> LENGTH: 286
<212> TYPE: PRT
<213> ORGANISM: Danio rerio
<220> FEATURE:
<221> NAME/KEY: SIGNAL
<222> LOCATION: (1)..(21)
<220> FEATURE:
<221> NAME/KEY: mat_peptide
<222> LOCATION: (22)..(286)

<400> SEQUENCE: 22

Met Leu Ser Pro Phe Leu Ala Tyr Leu Ser Val Val Leu Leu Cys
        -20                 -15                 -10

Arg Ile Ala Arg Ser Gln Tyr Ser Ser Asp Gln Cys Ser Trp Arg Gly
 -5             -1   1               5                  10

Ser Gly Leu Thr His Glu Gly His Thr Arg Gly Val Glu Gln Val Tyr
                15                  20                  25

Leu Arg Cys Ala Gln Gly Phe Leu Glu Trp Leu Tyr Pro Thr Gly Ala
            30                  35                  40

Ile Ile Val Asn Leu Arg Pro Asn Thr Leu Ser Pro Ala Ala Ser Leu
        45                  50                  55

Leu Ser Val Cys Ile Lys Pro Ser Lys Glu Ser Ser Gly Thr His Ile
60                  65                  70                  75

Tyr Leu Asp Arg Leu Gly Lys Leu Arg Leu Leu Ser Glu Gly Asp
                80                  85                  90

Gln Ala Glu Gly Lys Val His Cys Phe Asn Ile Gln Asp Gly Ala Leu
            95                  100                 105

Phe Ile Glu Ala Val Pro Gln Arg Asp Ile Ser Arg Lys Ile Thr Ala
        110                 115                 120

Phe Gln Tyr Glu Leu Val Asn His Arg Pro Gly Ala Asp Pro Gln Ser
    125                 130                 135

Leu Ser Ala Pro Cys Gln Pro Cys Thr Asp Ala Glu Val Leu Leu Ala
140                 145                 150                 155

Val Cys Thr Ser Asp Phe Val Ala Arg Gly Arg Ile Leu Gly Val Ser
                160                 165                 170

Glu Glu Asp Glu Gln Thr Ser Val Thr Val Ser Leu Ser His Leu Tyr
            175                 180                 185

Arg Gln Lys Thr Gln Val Phe Val Ser Gly Gly Arg Ala Lys Arg
        190                 195                 200

Trp Thr Gly Phe Val Lys Met Ser Arg Gln Cys Gly Val Lys Pro Gly
    205                 210                 215

Asp Gly Glu Phe Leu Phe Thr Gly Thr Val Arg Phe Gly Glu Ala Trp
220                 225                 230                 235

Leu Ser Cys Ala Pro Arg Tyr Lys Asp Phe Leu Arg Val Tyr Gln Asp
                240                 245                 250

Ala Arg Gln Gln Gly Thr Asn Pro Cys His Leu Glu Thr Asp
        255                 260                 265

<210> SEQ ID NO 23
<211> LENGTH: 293
<212> TYPE: PRT
<213> ORGANISM: Homo sapiens
```

-continued

```
<220> FEATURE:
<221> NAME/KEY: SIGNAL
<222> LOCATION: (1)..(23)
<220> FEATURE:
<221> NAME/KEY: mat_peptide
<222> LOCATION: (24)..(293)

<400> SEQUENCE: 23

Met Gly Phe Pro Ala Ala Ala Leu Leu Cys Ala Leu Cys Cys Gly Leu
            -20                 -15                 -10

Leu Ala Pro Ala Ala Arg Ala Gly Tyr Ser Glu Glu Arg Cys Ser Trp
         -5              -1   1               5

Arg Gly Ser Gly Leu Thr Gln Glu Pro Gly Ser Val Gly Gln Leu Ala
 10              15                  20                  25

Leu Ala Cys Ala Glu Gly Ala Val Glu Trp Leu Tyr Pro Ala Gly Ala
                 30                  35                  40

Leu Arg Leu Thr Leu Gly Gly Pro Asp Pro Arg Ala Arg Pro Gly Ile
                 45                  50                  55

Ala Cys Leu Arg Pro Val Arg Pro Phe Ala Gly Ala Gln Val Phe Ala
                 60                  65                  70

Glu Arg Ala Gly Gly Ala Leu Glu Leu Leu Ala Glu Gly Pro Gly
 75                  80                  85

Pro Ala Gly Gly Arg Cys Val Arg Trp Gly Pro Arg Glu Arg Arg Ala
 90                  95                 100                 105

Leu Phe Leu Gln Ala Thr Pro His Gln Asp Ile Ser Arg Arg Val Ala
                110                 115                 120

Ala Phe Arg Phe Glu Leu Arg Glu Asp Gly Arg Pro Glu Leu Pro Pro
                125                 130                 135

Gln Ala His Gly Leu Gly Val Asp Gly Ala Cys Arg Pro Cys Ser Asp
                140                 145                 150

Ala Glu Leu Leu Leu Ala Ala Cys Thr Ser Asp Phe Val Ile His Gly
                155                 160                 165

Ile Ile His Gly Val Thr His Asp Val Glu Leu Gln Glu Ser Val Ile
170                 175                 180                 185

Thr Val Val Ala Ala Arg Val Leu Arg Gln Thr Pro Pro Leu Phe Gln
                190                 195                 200

Ala Gly Arg Ser Gly Asp Gln Gly Leu Thr Ser Ile Arg Thr Pro Leu
                205                 210                 215

Arg Cys Gly Val His Pro Gly Pro Gly Thr Phe Leu Phe Met Gly Trp
                220                 225                 230

Ser Arg Phe Gly Glu Ala Arg Leu Gly Cys Ala Pro Arg Phe Gln Glu
                235                 240                 245

Phe Arg Arg Ala Tyr Glu Ala Arg Ala Ala His Leu His Pro Cys
250                 255                 260                 265

Glu Val Ala Leu His
                270

<210> SEQ ID NO 24
<211> LENGTH: 291
<212> TYPE: PRT
<213> ORGANISM: Mus musculus
<220> FEATURE:
<221> NAME/KEY: SIGNAL
<222> LOCATION: (1)..(21)
<220> FEATURE:
<221> NAME/KEY: mat_peptide
<222> LOCATION: (22)..(291)
```

-continued

```
<400> SEQUENCE: 24

Met Leu Val Ala Thr Leu Leu Cys Ala Leu Cys Cys Gly Leu Leu Ala
    -20                 -15                 -10

Ala Ser Ala His Ala Gly Tyr Ser Glu Asp Arg Cys Ser Trp Arg Gly
 -5          -1   1               5                      10

Ser Gly Leu Thr Gln Glu Pro Gly Ser Val Gly Leu Thr Leu Asp
             15                  20                  25

Cys Thr Glu Gly Ala Ile Glu Trp Leu Tyr Pro Ala Gly Ala Leu Arg
             30                  35                  40

Leu Thr Leu Gly Gly Pro Asp Pro Gly Thr Arg Pro Ser Ile Val Cys
         45                  50                  55

Leu Arg Pro Glu Arg Pro Phe Ala Gly Ala Gln Val Phe Ala Glu Arg
 60                  65                  70                  75

Met Thr Gly Asn Leu Glu Leu Leu Ala Glu Gly Pro Asp Leu Ala
                 80                  85                  90

Gly Gly Arg Cys Met Arg Trp Gly Pro Arg Glu Arg Arg Ala Leu Phe
             95                 100                 105

Leu Gln Ala Thr Pro His Arg Asp Ile Ser Arg Arg Val Ala Ala Phe
             110                 115                 120

Arg Phe Glu Leu His Glu Asp Gln Arg Ala Glu Met Ser Pro Gln Ala
             125                 130                 135

Gln Gly Leu Gly Val Asp Gly Ala Cys Arg Pro Cys Ser Asp Ala Glu
140                 145                 150                 155

Leu Leu Leu Ala Ala Cys Thr Ser Asp Phe Val Ile His Gly Thr Ile
                 160                 165                 170

His Gly Val Ala His Asp Thr Glu Leu Gln Glu Ser Val Ile Thr Val
                 175                 180                 185

Val Val Ala Arg Val Ile Arg Gln Thr Leu Pro Leu Phe Lys Glu Gly
             190                 195                 200

Ser Ser Glu Gly Gln Gly Arg Ala Ser Ile Arg Thr Leu Leu Arg Cys
205                 210                 215

Gly Val Arg Pro Gly Pro Gly Ser Phe Leu Phe Met Gly Trp Ser Arg
220                 225                 230                 235

Phe Gly Glu Ala Trp Leu Gly Cys Ala Pro Arg Phe Gln Glu Phe Ser
                 240                 245                 250

Arg Val Tyr Ser Ala Ala Leu Thr Thr His Leu Asn Pro Cys Glu Met
             255                 260                 265

Ala Leu Asp
         270

<210> SEQ ID NO 25
<211> LENGTH: 291
<212> TYPE: PRT
<213> ORGANISM: Rattus norvegicus
<220> FEATURE:
<221> NAME/KEY: SIGNAL
<222> LOCATION: (1)..(21)
<220> FEATURE:
<221> NAME/KEY: mat_peptide
<222> LOCATION: (22)..(291)

<400> SEQUENCE: 25

Met Leu Val Ala Ala Leu Leu Cys Ala Leu Cys Cys Gly Leu Leu Ala
                -20                 -15                 -10

Ala Ser Ala Arg Ala Gly Tyr Ser Glu Asp Arg Cys Ser Trp Arg Gly
 -5          -1   1               5                      10
```

```
Ser Gly Leu Thr Gln Glu Pro Gly Ser Val Gly Gln Leu Thr Leu Asp
            15                  20                  25

Cys Thr Glu Gly Ala Ile Glu Trp Leu Tyr Pro Ala Gly Ala Leu Arg
        30                  35                  40

Leu Thr Leu Gly Gly Ser Asp Pro Gly Thr Arg Pro Ser Ile Val Cys
        45                  50                  55

Leu Arg Pro Thr Arg Pro Phe Ala Gly Ala Gln Val Phe Ala Glu Arg
60                  65                  70                  75

Met Ala Gly Asn Leu Glu Leu Leu Leu Ala Glu Gly Gln Gly Leu Ala
                80                  85                  90

Gly Gly Arg Cys Met Arg Trp Gly Pro Arg Glu Arg Arg Ala Leu Phe
            95                  100                 105

Leu Gln Ala Thr Pro His Arg Asp Ile Ser Arg Arg Val Ala Ala Phe
            110                 115                 120

Gln Phe Glu Leu His Glu Asp Gln Arg Ala Glu Met Ser Pro Gln Ala
            125                 130                 135

Gln Gly Phe Gly Val Asp Gly Ala Cys Arg Pro Cys Ser Asp Ala Glu
140                 145                 150                 155

Leu Leu Leu Thr Ala Cys Thr Ser Asp Phe Val Ile His Gly Thr Ile
            160                 165                 170

His Gly Val Val His Asp Met Glu Leu Gln Glu Ser Val Ile Thr Val
            175                 180                 185

Val Ala Thr Arg Val Ile Arg Gln Thr Leu Pro Leu Phe Gln Glu Gly
            190                 195                 200

Ser Ser Glu Gly Arg Gly Gln Ala Ser Val Arg Thr Leu Leu Arg Cys
            205                 210                 215

Gly Val Arg Pro Gly Pro Gly Ser Phe Leu Phe Met Gly Trp Ser Arg
220                 225                 230                 235

Phe Gly Glu Ala Trp Leu Gly Cys Ala Pro Arg Phe Gln Glu Phe Ser
                240                 245                 250

Arg Val Tyr Ser Ala Ala Leu Ala Ala His Leu Asn Pro Cys Glu Val
            255                 260                 265

Ala Leu Asp
        270

<210> SEQ ID NO 26
<211> LENGTH: 12
<212> TYPE: PRT
<213> ORGANISM: Artificial Sequence
<220> FEATURE:
<223> OTHER INFORMATION: C-terminal His-tag of METRNL

<400> SEQUENCE: 26

Gly Ser Gly Ser Gly Ser His His His His His His
1               5                   10
```

THERAPEUTIC USE OF A GROWTH FACTOR, METRNL

The present application is a continuation of U.S. patent application Ser. No. 12/936,501, filed Oct. 5, 2010, issued as U.S. Pat. No. 8,334,264, which is a national phase application of International Application No. PCT/DK2009/050165, filed Jul. 7, 2009, which claims the benefit of U.S. 61/083,316, filed Jul. 24, 2008, which is incorporated by reference in its entirety. It claims priority from Danish patent application no. PA 2008 01036, filed Jul. 24, 2008. All references cited in those applications and in the present application are hereby incorporated by reference in their entirety.

TECHNICAL FIELD

The present invention relates to the field of therapeutic use of proteins, genes and cells, in particular to the therapy based on the biological function of a secreted therapeutic protein, METRNL, in particular for the treatment of disorders of the nervous system. METRNL is a Nerve Survival and Growth factor with neuroprotective and/or neurogenesis effects.

BACKGROUND ART

Extracellular proteins play important roles in, among other things, the formation, differentiation and maintenance of multicellular organisms. The fate of many individual cells, e.g., growth including survival, proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Disorders such as Parkinson's disease, Alzheimer's disease, Huntington's disease, multiple sclerosis, amyotrophic lateral sclerosis, stroke, schizophrenia, epilepsy and peripheral neuropathy and associated pain affect millions of people. It is the loss of normal neuronal function, which produces the behavioral and physical deficits which are characteristic of each of the different neurological disorders. In addition to chronic and acute neurodegenerative disorders, the aging process, physical trauma to the nervous system, and metabolic disorders may result in the loss, dysfunction, or degeneration of neural cells accompanied by the associated behavioral and physical deficits. Many of these diseases are today incurable, highly debilitating, and traditional drug therapies often fail. There is thus a great medical need for new therapeutic proteins that are disease modifying or for symptomatic use or both.

Several secreted factors with expression in the nervous system or associated target areas have important therapeutic uses in various neurological indications associated with reduction or loss of neuronal functions. E.g. NGF is a candidate for treatment of Alzheimer's disease, Neublastin (Artemin) a candidate for treatment of peripheral neuropathy, and GDNF is a candidate for treatment of Parkinson's Disease.

WO 93/22437 (Innogenetics) discloses a polypeptide which is identical to METRNL. It is suggested that the protein or its antagonist can be used as antitumor compounds, or anti-inflammatory compounds or as growth activators of T-cells and B-cells, as bone repair compounds as inducer of immunosuppressive cells, as inhibitors of anti-colony stimulating factor; or as trypanocidal agents.

WO 01/039786 (Innogenetics) discloses specific uses of polypeptides denominated as suppressive macrophage activation factors (SMAF's) wherein SMAF-1 is 100% identical to METRNL. Specifically, it is disclosed that SMAF-1 and/or SMAF-2 modulate the production of Th1, Th2 and/or Th3 cytokines and indicates how the latter molecules, nucleic acids encoding them and antibodies against them can be used to treat diseases mediated by type 1, type 2 and/or type 3 responses such as inflammation, infections, allergies, autoimmune diseases, transplant rejections, graft-versus-host disease, malignancies and diseases involving mucosal immunity.

METRNL is not described individually in the scientific literature. However, in a very large gene expression data set examining several tissues in different rat strains (Walker et al (2004). Applications of a rat multiple tissue gene expression data set. Genome Res. 14, 742-749), Meteorin-like is absent from the CNS and only detected in cornea, spleen, endothelial cells and intestines (GEO, GDS589/rc_AI639012_at). In the GNF SymAtlas v1.2.4, Meteorin-like is not reliably detected in any of the 60 mouse tissues examined (GFN1M, gnf1m08104_at).

It has been demonstrated that METRNL is one of several genes regulated by Pax2 and thereby expressed in the inner ear during development in Japanese killifish, medaka (*Oryzias latipes*) (Ramialison et al., Genome Biol. 2008 Oct. 1; 9(10):R145). The authors conclude that the Pax2 regulated genes are "novel otic vesicle specific genes, which are amenable to further functional analysis".

WO 2005/095450 (NsGene) discloses NsG33 also known as Meteorin (METRN) and its use for treatment of neurological disorders or diseases. METRN is related to METRNL but the full length polypeptides share only 44% sequence identity. The expression of METRN is primarily restricted to the central nervous system and it has been shown to be active in several in vitro assays with primary and secondary neuronal cell types. Nishino et al (EMBO Journal (2004) 23, 1998-2008) also discloses METRN and its effects on regulation of glial cell differentiation and axonal extension.

While the prior art clearly indicates that METRN is a neurotrophic factor, METRNL has not been suggested for such uses. Based on the functional data available in WO 01/039786 and WO 93/22437 it would not be expected that METRNL would have any effect on the nervous system. The expression data available in the art also do not hint in this direction.

SUMMARY OF THE INVENTION

The present inventors have found that METRNL is a secreted protein with growth factor characteristics, and with effects on the nervous system. First and foremost, the inventors have found that METRNL is functional in an in vivo model of hearing loss (Example 2A). The observed effect may include a neuro-regenerative effect and/or a neuroprotective and/or a survival effect. These effects are predictive of a general neuroprotective effect and more specifically of an effect on the central nervous system. In particular in connection with treatment of a disease, disorder, or damage involves the sensory epithelium and associated ganglia of the inner ear, including but not limited to noise induced hearing loss, deafness, tinnitus, otitis, labyrintitis, hereditary and cochleovestibular atrophies, Meniere's Disease, and associated symptoms.

In addition, the present inventors have found that METRNL is capable of promoting axonal extension in dissociated rat p5 dorsal root ganglion cell cultures (Example 2). The observed effect may include a differentiating effect, a neuro-regenerative effect, and/or a neuroprotective and/or a survival effect. These effects are predictive of a general neuroprotective effect and more specifically predictive of an effect on the peripheral nervous system, in particular in connection with treatment of peripheral neuropathy and/or associated pain or in connection with treatment of disorders of the spinal cord such as spinal cord injury, root avulsion, root injury, and peripheral nerve injury such as brachial plexus injury.

METRNL has also shown a stimulatory effect on migration of neuroblasts (neuronal precursors) in the subventricular zone (Example 2). This effect is regarded as a neuromigratory effect and may also include neurogenesis effects and survival effects. The observed effect is generally predictive of a use in the neural system where survival, neurogenesis or recruitment of neuronal and/or glial precursors is desirable, e.g. in connection with trauma, injury, stroke and neurodegenerative disorders.

Other therapeutically relevant secreted growth factors have shown similar effects in one or more of these functional assays including but not limited to BDNF, Neublastin (Artemin), GDNF, NGF, Neurturin, NT4/5, NT3, and SDF1a. Cell death such as apoptotic cell death contributes to neuronal cell loss in the adult nervous system causing various neurological disorders like ischemic stroke, neurodegenerative diseases or brain traumata (Becker and Bonni, Prog Neurobiol. 2004 January; 72(1):1-25).

Therefore, the present inventors have contemplated the use of METRNL in the treatment of disorders of the central nervous system, in particular in the treatment of hearing loss, deafness, tinnitus, otitis, labyrintitis, hereditary and cochleo-vestibular atrophies, Meniere's Disease, treatment of stroke, injury or trauma of the CNS, treatment of Parkinson's Disease, and Huntington's disease, peripheral neuropathies and associated pain and treatment of disorders of the spinal cord, such as spinal cord injury, pain, trauma, root injury, root avulsion, peripheral nerve injury such as brachial plexus injury, and ALS.

Thus in a particular embodiment of the invention, METRNL may be used in the treatment of disease, disorder or damage of the neural system, wherein neural cells are lost or damaged.

The therapeutic effect of METRNL may be mediated through an effect on migration, differentiation, growth, survival, regeneration, and/or regain or improvement of function of targeted cells. The present inventors have demonstrated that METRNL is functional in an in vivo model of hearing loss (Example 2A). The present inventors have shown that METRNL is capable of stimulating neurogenesis, survival and/or differentiation in Dorsal Root Ganglion (DRG) cultures (Example 2). The present inventors have also shown that explants of the murine Subventricular Zone (SVZ) show enhanced migration of neuronal precursors, enhanced neurogenesis and/or enhanced survival when exposed to METRNL (Example 2). The latter effect may be caused by improved migration of neurons, enhanced survival of neurons, and/or by neurogenesis.

Based on these biological assays, the present invention relates to a method of differentiating a neuronal cell, said method comprising exposing said neuronal cell to a polypeptide or a coding polynucleotide of the invention. By a neuronal cell is understood oligodendrycytes, astrocytes, glial cells, Schwann cells, neurons, and their precursors. The invention also relates to a method of stimulating migration of neuronal cells, said method comprising exposing said neuronal cell to a polypeptide or a coding polynucleotide of the present invention. The invention also relates to a method of preventing apoptosis in a mammalian neuronal cell, said method comprising exposing said neuronal cell to a polypeptide or a coding polynucleotide of the present invention. The invention also relates to a method of enhancing survival of a mammalian neuronal cell, said method comprising exposing said neuronal cell to a polypeptide or a coding polynucleotide of the present invention. The invention additionally relates to a method of generating a neuron, said method comprising exposing a neuronal precursor cell or a neuronal stem cell including stem cells and neural stem cells to a polypeptide or a coding polynucleotide of the present invention. Preferably, said mammalian neuronal cell and/or mammalian neuronal precursor or stem cell or neural stem cell is a human cell.

In a still further aspect the invention relates to an isolated host cell comprising an expression vector according to the invention for use in a method of treatment of a disease, disorder or damage of the nervous system. In particular, the invention relates to host cells useful for cell based therapy, either naked cell based therapy or encapsulated cell therapy for use in such methods.

In a further aspect the invention relates to a packaging cell line capable of producing an infective virus particle for use in a method of treatment of a disease, disorder or damage of the nervous system, said virus particle comprising a Retroviridae derived genome comprising a 5' retroviral LTR, a tRNA binding site, a packaging signal, a promoter operably linked to a polynucleotide sequence encoding a polypeptide of the invention, an origin of second strand DNA synthesis, and a 3' retroviral LTR.

In a further aspect the invention relates to an implantable biocompatible cell device, the device comprising:
i) a semipermeable membrane permitting the diffusion of a protein of the invention; and
ii) a composition of cells according to the invention, or a composition of packaging cells according to the invention.

In a further aspect the invention relates to the use of
i) a polypeptide of the invention; or
ii) an isolated nucleic acid sequence of the invention; or
iii) an expression vector of the invention; or
iv) a composition of host cells according to the invention; or
v) a packaging cell line according to the invention; or
vi) an implantable biocompatible capsule according to the invention.
for use in a method of treatment of a disease, disorder or damage of the nervous system.

In a further aspect the invention relates to a method of treatment of a disease, disorder or damage of the nervous system in a subject, comprising administering to a subject in need thereof a therapeutically effective amount of:
i) a polypeptide of the invention; or
ii) an isolated nucleic acid sequence of the invention; or
iii) an expression vector of the invention; or
iv) a composition of host cells according to the invention; or
v) a packaging cell line according to the invention; or
vi) an implantable biocompatible capsule according to the invention.

In a further aspect the invention relates to the use of
i) a polypeptide of the invention; or
ii) an isolated nucleic acid sequence of the invention; or
iii) an expression vector of the invention; or
iv) a composition of host cells according to the invention; or
v) a packaging cell line according to the invention;
as a growth factor in a neuronal mammalian cell culture.

In one aspect the invention relates to use of an antibody capable of binding to a polypeptide of the invention for use in a method of treatment of a disease, disorder or damage of the nervous system.

In a further aspect the invention relates to an immunoconjugate comprising the antibody of the invention and a conjugate selected from the group consisting of: a cytotoxic agent such as a chemotherapeutic agent, a toxin, or a radioactive isotope; a member of a specific binding pair, such as avidin or streptavidin or an antigen; an enzyme capable of producing a detectable product for use in a method of treatment of a disease, disorder or damage of the nervous system In a further aspect the invention relates to specific truncated forms of METRNL. These truncated forms of METRNL comprise a bioactive core sequence from the first to the last conserved cysteine. Preferably these truncated forms of METRNL include at least one further amino acid N-terminal to the first conserved cysteine and at least one further amino acid C-terminal to the 10th conserved cysteine. Preferably these terminal amino acids are not cysteine.

In a further aspect the invention relates to an isolated polypeptide comprising an N-terminal amino acid selected from the group consisting of naturally occurring amino acids except Gln or Cys, said N-terminal amino acid being C-terminally linked to a polypeptide selected from the group consisting of polypeptides having an amino acid sequence as set forth in $AA_2$ to $AA_{311}$ of SEQ ID No 2, SEQ ID NO 4 or SEQ ID No 6 and variants of said polypeptides, wherein any amino acid is changed to a different amino acid, provided that no more than 20 of the amino acid residues in the sequence are so changed. Said polypeptides avoid the presence of an N-terminal pyrrolidone carboxylic acid and thus facilitate N-terminal sequencing of the obtained product.

In another aspect the invention relates to an isolated polypeptide selected from the group consisting of polypeptide having an amino acid sequence as set forth in SEQ ID No 2, SEQ ID NO 4 or SEQ ID No 6, having an N-terminal pyrrolidone carboxylic acid instead of the N-terminal glutamine residue; and variants of said polypeptides, wherein any amino acid except the N-terminal pyrrolidone carboxylic acid specified in the chosen sequence is changed to a different amino acid, provided that no more than 20 of the amino acid residues in the sequence are so changed.

The present inventors have discovered that the N-terminal Gln residue is quantitatively converted into pyrrolidone carboxylic acid upon recombinant expression. Furthermore, the inventors have analysed the conservation of said residue across species. All species analysed have a fully conserved N-terminal following the cleavage of the signal peptide. As METRNL with an N-terminal pyrrolidone carboxylic acid is bioactive, it is believed that the presence of the N-terminal pyrrolidone carboxylic acid is important for maintaining biological activity.

In a related aspect the invention relates to a method for manufacturing a recombinant METRNL polypeptide comprising expressing in a cell a nucleic acid coding for a METRNL polypeptide of the invention; purifying said polypeptide; and verifying the presence of an N-terminal pyrrolidone carboxylic acid in the purified polypeptide.

In a further aspect the invention relates to an implant wherein at least part of the surface is coated with a METRNL protein formulation, the METRNL protein being a polypeptide of the invention. Preferably the implant is selected from the group consisting of cochlear implants, middle ear implants, Bone-anchored hearing aids, and auditory brainstem implants, preferably cochlear implants and middle ear implants.

BRIEF DESCRIPTION OF THE DRAWINGS

FIG. 1: Alignment of human, mouse and rat Meteorin-like protein (SEQ ID NO 2, 4, and 6). Predicted signal peptide in bold. Alignments were made using CLUSTAL W (1.7) (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680.). BLOSUM 62 was used as scoring matrix.

| Sequence | Start | End | Match | NonMatch | % Match |
| --- | --- | --- | --- | --- | --- |
| hMETRNL | 1 | 311 | | | |
| mMETRNL | 1 | 311 | 241 | 70 | 77 |
| rMETRNL | 1 | 311 | 243 | 68 | 78 |

FIG. 2: Alignment of human, mouse, and rat Meteorin-like (SEQ ID NO 2, 4, and 6) and human, mouse and rat Meteorin (SEQ ID NO 23, 24, and 25). Signal peptide in bold. Conserved Cys residues boxed. Clustal W (1.7) was used for alignment.

| Sequence | Start | End | Match | NonMatch | % Match |
| --- | --- | --- | --- | --- | --- |
| hMETRNL | 1 | 311 | | | |
| mMETRNL | 1 | 311 | 241 | 70 | 77 |
| rMETRNL | 1 | 311 | 243 | 68 | 78 |
| hMETRN | 1 | 293 | 138 | 185 | 42 |
| mMETRN | 1 | 291 | 139 | 187 | 43 |
| rMETRN | 1 | 291 | 140 | 186 | 43 |

FIG. 3: Alignment of human (NP_001004431.1; SEQ ID NO 2), mouse (NP_659046.1; SEQ ID NO 4), rat (NP_001014126; SEQ ID NO 6), cow (XP_614019.3; SEQ ID NO 19), chicken (CR352488; SEQ ID NO 20), *xenopus tropicalis* (BX757299.1; SEQ ID NO 21) and zebrafish (NP_998150.1; SEQ ID NO 22) METRNL protein sequences. Conserved residues identical to the human sequence are shaded, predicted signal peptides are in bold, ten conserved cysteine residues are boxed and the conserved N-terminal Glutamine (Q) of the mature protein sequence marked by an arrow.

Figure 4:
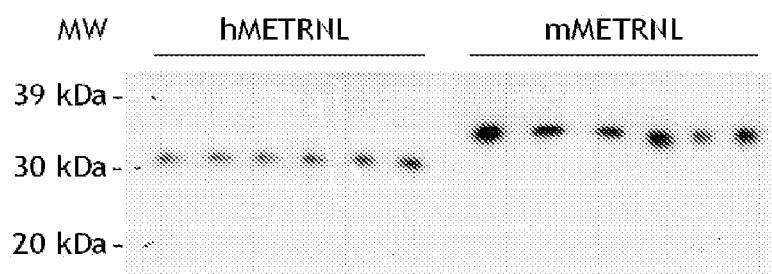

FIG. 4. Human and mouse METRNL are secreted molecules. HEK293 cells were transfected with Histidine-tagged human or mouse METRNL in hexaplicates. After 48 hours, conditioned media was analyzed by Anti-HIS western blotting. Both mature molecules have a predicted size of 31.2 kDa. hMETRNL travels as expected but mMETRNL travels at a higher molecular weight due to glycosylation.

Figure 5:
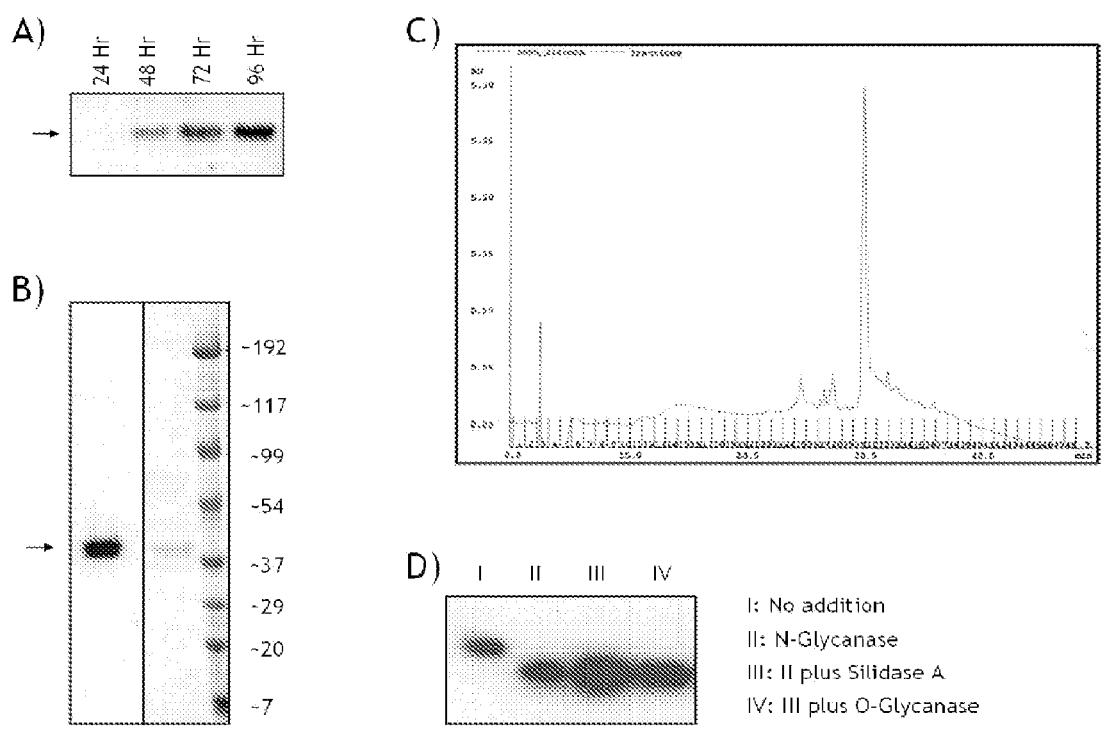

FIG. 5. Production of recombinant mMETRNL. A) 293F suspension cells were transfected with pNS1n-mMETRNL-HIS and conditioned media collected the following days. Anti-HIS western blotting demonstrates continuous accumulation up to 96 hours. B) After purification, recombinant mMETRNL was analyzed by SDS-PAGE followed by anti-HIS western blotting (left) and Gelcode Blue staining (right). C) Purified recombinant mMETRNL was further analyzed by reverse phase chromatography, indicating high purity. The shoulder in fractions ≥31 is typical for heterogeneously glycosylated proteins. D) Purified recombinant mMETRNL was treated with different deglycolating enzymes as indicated and analyzed by anti-HIS western blotting. It is evident from the shift in molecular weight that mMETRNL is N-glycosylated.

Figure 6:
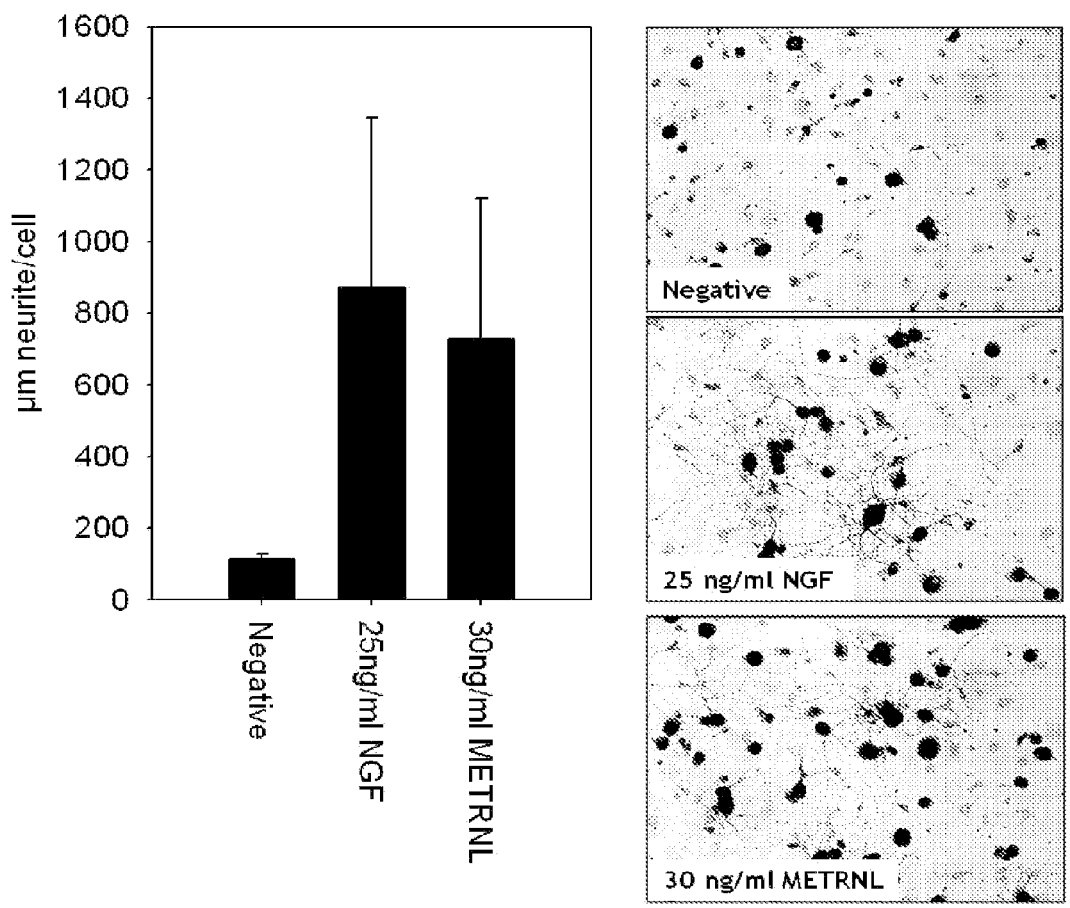

FIG. 6. METRNL induces neurite outgrowth from dissociated dorsal root ganglions (DRGs). Left, quantification of neurite length. Right, β-III-Tubulin stained dorsal root ganglion cells grown without neurotrophic support (negative) or with NGF or METRNL.

Figure 7:
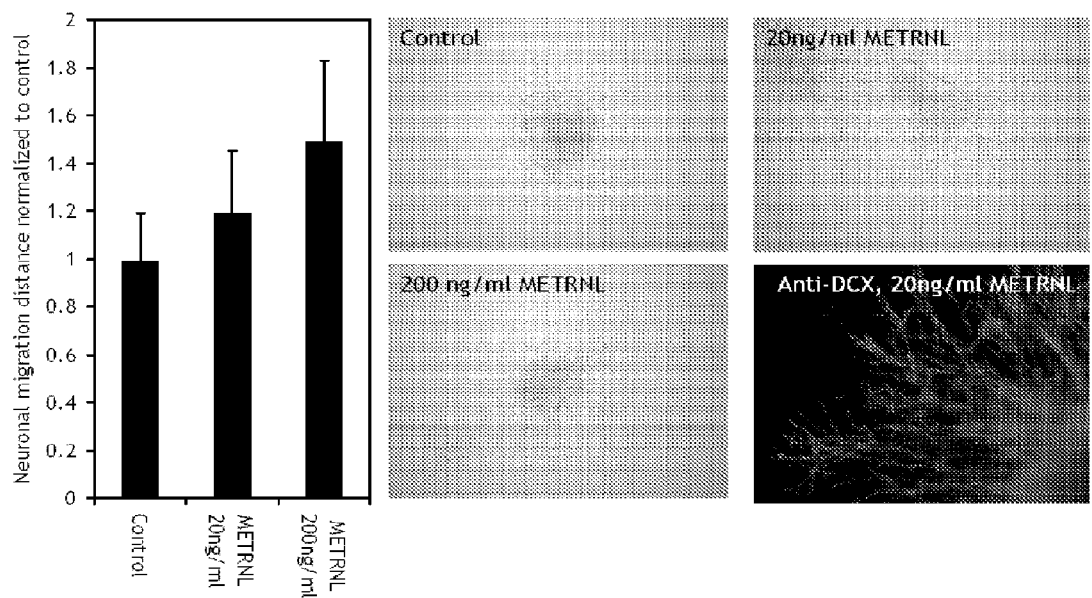

FIG. 7. METRNL increases neuronal migration of neuroblasts derived from the SVZ in dose-dependent mode. The cells that respond to METRNL in this process are identified as neuroblasts because they are immunoreactive to the marker DCX.

FIG. 8. METRNL stimulates SVZ derived neuroblast migration in vitro. A) SVZ explants from P2-P5 rat pubs were embedded in Matrigel with different concentrations of recombinant METRNL (0, 20, 200, 2000 ng/ml). The presence of METRNL caused a significant increase of cell migration in a dose-dependent mode. B) The migrating cells are neuroblasts as they are Doublecortin (DCX) positive and Glial Fibrillary Acidic Protein (GFAP) negative.

Figure 9:
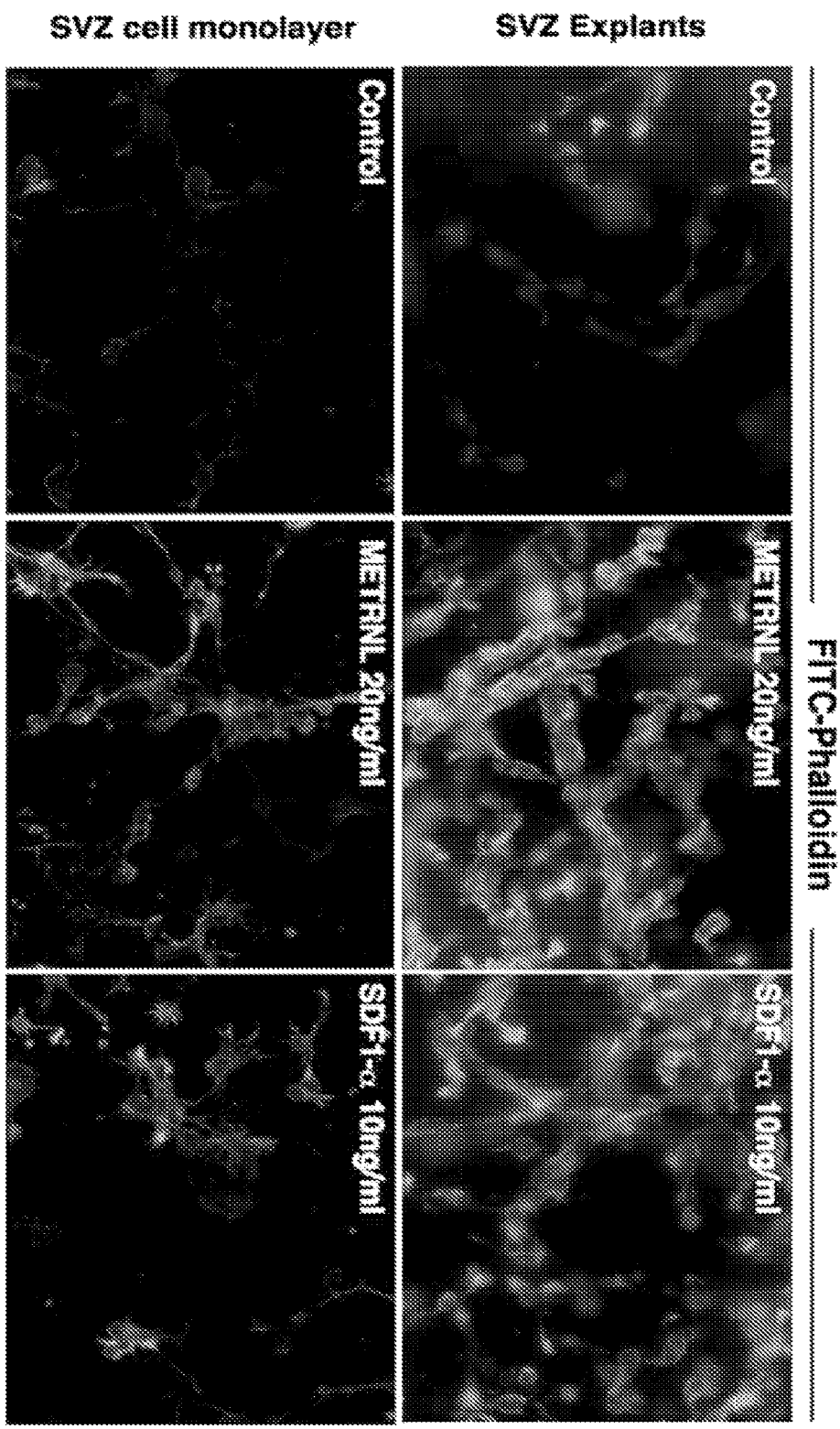

FIG. 9. METRNL promotes cell migration through actin polymerization. SVZ explants and monolayer cultures were treated with recombinant mouse METRNL or SDF1a (positive control) followed by incubation with actin binding FITC-phalloidin. The increase in actin polymerization is further evidence for a role of METRNL in promoting neuroblast migration.

FIG. 10. Human recombinant METRNL stimulates SVZ derived neuroblast migration. SVZ explants from P2-P5 rat pubs were embedded in Matrigel with 25 ng/ml human recombinant METRNL which more than doubles migration compared to the control. A) Photographic example of human METRNL induced neuroblast migration compared to control. Note the typical neuroblast chain migration. B) Quantification of neuroblast migration.

FIG. 11. METRNL protects hearing in deafened guinea pigs. A) Experimental setup. See Methods for detailed description. B) Mean electrically auditory brainstem response (eABR) thresholds measured in: Normal hearing guinea pigs treated with METRNL (○), deafened guinea pigs treated with artificial perilymph (●) and deafened guinea pigs treated with recombinant mouse METRNL (Δ). Vertical bars indicate standard error of the mean (SEM). Note that treatment with METRNL significantly reduces the eABR threshold (*$p<0.05$) compared to untreated control group.

DEFINITIONS

METRNL, as used herein, refers to polypeptides having the amino acid sequences of substantially purified METRNL obtained from any species, particularly mammalian, including chimpanzee, bovine, ovine, porcine, murine, equine, and preferably human, from any source whether natural, synthetic, semi-synthetic, or recombinant. The term also refers to biologically active fragments of METRNL obtained from any of these species, as well as to biologically active sequence variants of these and to proteins subject to posttranslational modifications. Biologically active fragments of METRNL may differ at one or more positions from the wildtype METRNL sequences, preferably at up to 20 of the positions, more preferably up to 10 positions, more preferably at up to 5 positions, such as at one, two, three or four positions.

Growth factor characteristics as used herein define sequence-related features similar to those of classical growth factors, which are secreted proteins acting on a target cell through a receptor to cause one or more of the following responses in the target cell: growth including proliferation, differentiation, survival, regeneration, migration, regain of function, improvement of function.

An "allele" or "allelic sequence", as used herein, is an alternative form of the gene encoding METRNL. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

A "deletion", as used herein, refers to a change in the amino acid or nucleotide sequence and results in the absence of one or more amino acid residues or nucleotides.

An "insertion" or "addition", as used herein, refers to a change in an amino acid or nucleotide sequence resulting in the addition of one or more amino acid residues or nucleotides, respectively, as compared to the naturally occurring molecule.

The terms "specific binding" or "specifically binding", as used herein, refers to the high affinity interaction between a protein or peptide and a binding molecule such as an antibody and a receptor or fragments thereof. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Treatment" can be performed in several different ways, including curative, ameliorating and as prophylaxis. Curative treatment generally aims at curing a clinical condition, such as a disease or disorder, which is already present in the treated individual. Ameliorating treatment generally means treating in order to improve in an individual an existing clinical condition without necessarily curing the disease or disorder. Prophylactic treatment generally aims at preventing a clinical condition from arising or from worsening, i.e. from developing to a more serious stage.

"Sequence Identity":

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLASTN and BLASTP programs of Altschul, et al. (1990) J. Mol. Biol. 215:403-410.

In order to characterize the identity, subject sequences are aligned so that the highest order homology (match) is obtained. Based on these general principles, the "percent identity" of two nucleic acid sequences may be determined using the BLASTN algorithm [Tatiana A. Tatusova, Thomas L. Madden: Blast 2 sequences—a new tool for comparing protein and nucleotide sequences; FEMS Microbiol. Lett. 1999 174 247-250], which is available from the National Center for Biotechnology Information (NCBI) web site (http://www.ncbi.nlm.nih.gov), and using the default settings suggested here (i.e. Reward for a match=1; Penalty for a mismatch=−2; Strand option=both strands; Open gap=5; Extension gap=2; Penalties gap x_dropoff=50; Expect=10; Word size=11; Filter on). The BLASTN algorithm determines the % sequence identity in a range of overlap between two aligned nucleotide sequences.

Another preferred, non-limiting example of a mathematical algorithm utilized for the comparison of sequences is the CLUSTAL W (1.7) alignment algorithm (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680.). CLUSTAL W can be used for multiple sequence alignment preferably using BLOSUM 62 as scoring matrix. When calculating sequence identities, CLUSTAL W includes any gaps made by the alignment in the length of the reference sequence. Thus, in FIG. 2, the total length of the aligned sequences with gaps is 322, although the reference sequence (hMETRNL) is only 311 amino acids long. Sequence identities are calculated by dividing the number of matches by the length of the aligned sequences with gaps.

DETAILED DESCRIPTION

The present invention relates to the medical use of polypeptides and polynucleotides being identified as METRNL. The METRNL protein has been identified in human beings (SEQ ID No. 2), mouse (SEQ ID No. 4), and rat (SEQ ID No. 6), as well as cow (SEQ ID NO 19), chicken (SEQ ID NO 20), *Xenopus tropicalis* (SEQ ID NO 21), and Zebrafish (SEQ ID NO 22) (FIG. 3).

Human METRNL exists as a 311 amino acid precursor, which can be processed to give rise to at least one biologically active peptide. METRNL appears not to be expressed at high levels in any tissues. The mouse (SEQ ID No 4) and rat (SEQ ID No 6) METRNL polypeptides likewise consist of 311 amino acids, respectively and the % identities with the human protein are 77 and 78, respectively—calculated for the full length sequences.

Mouse METRNL contains an N-terminal signal peptide sequence of 45 amino acids, which is cleaved at the sequence motif ASA-QY. This signal peptide cleavage site is predicted by the SignalP method and has been verified experimentally by Mass Spectometry. An identical cleavage site is predicted in the human and rat proteins. Cleavage of the signal peptide results in polypeptides having SEQ ID No. 7, 8, and 9 for human, mouse, and rat respectively. As it is known in the art, signal peptide processing is not always exactly as predicted and actual cleavage may vary from case to case. Thus, it is expected that the N-terminal of mature METRNL may vary by one to two or three amino acids from the predicted cleavage site.

METRNL is structurally related to METRN (NsG33, Meteorin) protein described in WO 2005/095450 (NsGene). The full length human, mouse and rat proteins are shown in FIG. 2. METRN shares $^{42}/_{43}$% identity (Clustal W (1.7) with standard settings) to the human METRNL protein.

A full length alignment of human METRNL to METRN protein is shown in FIG. 2. Ten conserved cysteines are boxed. The two proteins together form a protein family based on the conserved cysteine residues and the stretches of high conservation which are evident from FIG. 2. None of the two proteins show any significant sequence homology to any other known human proteins. Although the two proteins are members of the same small protein family, the two proteins are structurally distinct.

Due to the high conservation of the cysteines, it is expected that these residues play an important role in the secondary and tertiary structure of the bioactive protein. One or more of the cysteines may participate in the formation of intra- and/or intermolecular cystine-bridges.

METRNL belongs to the category of proteins acting as growth factors. This notion is supported by the fact that the protein is secreted, by its structural features (relatively small protein with a conserved cysteine pattern), and by the fact that it exerts growth factor effects on target cells. Furthermore METRNL is structurally related to the growth factor METRN.

Unlike structural proteins, growth factors are involved in cell signalling and in various functions such as growth, proliferation, differentiation, survival, regeneration, migration, regain of function, and/or improvement of function. Therefore, growth factors can be administered and be used to exert a therapeutic effect.

Factors capable of inducing differentiation, regeneration, and survival in of spiral ganglion cells include CNTF, GDNF, NT-3 and BDNF. These factors also display a similar activity in both the peripheral and central nervous system indicating that receptors and response systems expressed in spiral root ganglions are shared with many other neuronal cells.

Factors capable of inducing differentiation, regeneration, and survival in dorsal root ganglion explants cells include one of the neurotrophins (NGF), a member of the secretin/glucagon/VIP family (PACAP), Neublastin (Artemin), Meteorin, GDNF, NT-3 and BDNF. These factors also display a similar activity in both the peripheral and central nervous system indicating that receptors and response systems expressed in dorsal root ganglions are shared with many other neuronal cells.

NGF is an important differentiation and survival factor for responsive sympathetic and sensory neurons in addition to cholinergic neurons in the basal forebrain. PACAP promotes the differentiation of nascent dorsal root ganglion (DRG) neurons in that it increases both the number of neural-marker-positive cells and axonogenesis without affecting the proliferation of neural progenitor cells (Nielsen et al., Mol Cell Neurosci. 2004 April; 25(4):629-41). PACAP also show similar activities in neuronal populations in the CNS (Vaudry et al., Proc Natl Acad Sci USA. 2002 Apr. 30; 99(9):6398-403; Dicicco-Bloom et al., Ann NY Acad Sci. 1998 Dec. 11; 865: 274-89).

Cell death such as apoptotic cell death contributes to the neuronal cell loss in the adult nervous system causing various neurological disorders like ischemic stroke, neurodegenerative diseases or brain traumata (Becker and Bonni, Prog Neurobiol. 2004 January; 72(1):1-25). A secreted growth factor capable of protecting neuronal cells against apoptotic cell death is therefore a candidate for treating disorders of the nervous system in general and neurodegenerative disorders in particular. Thus, the ability of a secreted factor to induce neurite outgrowth and/or to promote survival under conditions leading to cell death is an indication that this factor has a similar effect in other neuronal cell types of the central and/or peripheral nervous system and that this factor is a candidate for treating nervous system disorders, in particular neurodegenerative disorders.

Based on the fact that METRNL is a secreted growth factor, and that METRNL stimulates neural migration, neural regeneration and differentiation and potentially also possess survival enhancing, neuroprotective and/or neurogenesis activity, METRNL is contemplated for use in treating disorders of the nervous system in general, in particular for treating a disease, disorder or damage involving injury to the brain, brain stem or spinal cord and/or peripheral nerves including but not limited to conditions such as stroke, traumatic brain injury, spinal cord injury, diffuse axonal injury, neuropathy, root injury, root avulsion and peripheral nerve injury such as brachial plexus injury (based on the effect in the DRG assay) peripheral neuropathy and associated pain (based on the effect in the DRG assay), Parkinson's disease (based on the effect in the SVZ assay), Huntingtons disease (based on the effect in the SVZ assay), ALS (based on the biological effects seen in the DRG assay, and on the ability to recruit neural precursors in the SVZ along the central canal), and neurophathic pain and peripheral neuropathies (based on the biological effects in DRG assay), and for the treatment of a disease, disorder, or damage involving the sensory epithelium and associated ganglia of the inner ear, including but not limited to noise induced hearing loss, deafness, tinnitus, otitis, labyrintitis, hereditary and cochleovestibular atrophies, Meniere's Disease, and associated symptoms (based on the effects in the in vivo model of hearing loss, Example 2A). The function for the various indications can be verified in in vitro and in vivo assays as described in the examples.

The therapeutic effect of METRNL may be mediated through an effect on growth including proliferation, regeneration, regain of function, improvement of function, survival, migration, and/or differentiation of targeted cells.

A verified biological function of METRNL is a neuroprotective/regeneration/survival effect on neural cells of the inner ear resulting in a protection against and potentially a curative effect on hearing loss.

One verified biological function of METRNL is a differentiation/regeneration/survival inducing effect on cultures of DRGs.

Another biological function of METRNL is a stimulating effect on the migration/generation/survival of neural precursors derived from the subventricular zone.

Adult neurogenesis is a concept that only recently became generally accepted by the scientific community. Before it was thought that the production of neurons in the CNS was restricted only to the embryonic stages. During the last decades it has been demonstrated that adult neurogenesis is also occurring and seems to be conserved across evolution. In mammals adult neurogenesis is mostly confined to specific and discreet regions of the CNS like the SVZ of the lateral ventricle and in the subgranular zone (SGZ) of the dentate gyrus in the hippocampus (Ming and Song, 2005, Annu Rev Neurosci, 28, 223,250). The SVZ of the lateral wall of the lateral ventricle of the murine brain has been extensively studied and neurons produced in this region normally migrate towards the olfactory bulbs, along the rostral migratory stream (RMS), where they will differentiate into granule and periglomerular interneurons (Doetsch and Alvarez-Buylla, 1996, Proc Natl Acad Sci USA, 93, 14895-900; Lois and Alvarez-Buylla, 1994, Science, 264, 1145-1148). From the SVZ to their final destination, postnatal-generated neurons go through several developmental stages and express specific protein markers that permit their identification.

Adult neurogenesis in the SVZ triggered particular attention when it was reported that after a CNS injury in a rat stroke model, this region responded by producing numerous new neurons that migrate towards the damaged tissue (Arvidsson et al., 2002, Nat Med, 8, 963-970), promising new therapeutic perspectives to tackle neurodegenerative diseases like stroke, Parkinson's disease or Alzheimer's disease, among others.

Other known trophic factors with therapeutic potential have been shown to increase the migration of neural cells from the subventricular zone. These include SDF1a, BDNF, NT3 and NT4/5 and platelet-derived growth factor (PDGF) (Caldwell et al, Nature Biotechnology, 2001 May, 19(5):475-9. Growth factors regulate the survival and fate of cells derived from human neurospheres). Consequently, these results also indicate that METRNL is a candidate factor for treating disorders of the nervous system and in particular disorders, damage and diseases where neurons are lost or damaged and recruitment of new neural precursor cells is desirable, e.g. trauma and neurodegenerative disorders.

I. METRNL Polypeptides

In addition to full-length METRNL, substantially full-length METRNL, and to truncated METRNL, the present invention provides for biologically active fragments and sequence variants of these polypeptides. A METRNL polypeptide, a sequence variant, or fragment is biologically active if it exhibits a biological activity of naturally occurring METRNL. Biologically active fragments of METRNL may differ at one or more positions from the wildtype METRNL sequences at up to 20 of the positions, more preferably up to 10 positions, more preferably at up to 5 positions, such as at one, two, three or four positions. It is to be understood that the invention relates to substantially purified METRNL as herein defined.

One biological activity is the ability to compete with naturally occurring METRNL in a receptor-binding assay.

Another biological activity is the ability to bind to an antibody, which is directed at an epitope, which is present on naturally occurring METRNL.

Biologically active variants may also be defined with reference to one or more of the biological assays described in the examples.

A preferred biological activity is the ability to elicit substantially the same response as in the DRG assay described in the Example 2 and FIG. 6. In this assay, cultures of dissociated rat P5 DRGs are exposed to murine METRNL protein (SEQ ID NO 8) with a C-terminal his-tag (SEQ ID NO 26). By substantially the same response in the DRG assay is intended that the neurite length per cell is at least 10% of the number obtained for C-terminally his-tagged mouse MERTNL in Example 2, more preferably at least 20%, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%.

The results in FIG. 6 may also be calculated as the percentage or number of neurite bearing cells. In that case, substantially the same response in the DRG assay is intended that the number of neurite bearing cells is at least 10% of the number obtained in Example 2, more preferably at least 20%, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%. The biological activity of a fragment or variant of METRNL may also be higher than that of the naturally occurring METRNL.

Another preferred biological activity includes the migratory effect shown in Example 2. In this assay explants from the subventricular zone (SVZ) are exposed to murine METRNL protein (SEQ ID NO 8) or to human METRNL protein (SEQ ID NO 7) with a C-terminal his-tag (SEQ ID NO 26) and neural cells are induced to migrate from the explant. By substantially the same response in the SVZ assay is intended that the average migration distance is at least 10% of the number obtained in Example 2, more preferably at least 20%, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%. The biological activity of a fragment or variant of METRNL may also be higher than that of the naturally occurring METRNL.

A further preferred biological activity includes the protection against hearing loss shown in Example 2A. In this assay deafened Guinea Pigs are exposed to murine METRNL protein (SEQ ID NO 8) with a C-terminal his-tag (SEQ ID NO 26) and are protected against further hearing loss. By substantially the same response in the hearing loss assay is intended that the threshold is up to +/−50 μA of the threshold achieved for METRNL treated animals, such as up to +/−40 μA, for example up to +/−30 μA, such as up to +/−20 μA, for example up to +/−10 μA of the threshold achieved for METRNL.

Specific preferred truncated forms of METRNL in one aspect, are selected from the group consisting of:
i) A polypeptide having an amino acid sequence as set forth in SEQ ID No 10, and polypeptides having from one to five extra amino acids;
ii) A polypeptide having an amino acid sequence as set forth in SEQ ID No 11, and polypeptides having from one to five extra amino acids;
iii) A polypeptide having an amino acid sequence as set forth in SEQ ID No 12, and polypeptides having from one to five extra amino acids; and
iv) variants of said polypeptides, wherein any amino acid specified in the chosen sequence is changed to a different amino acid, provided that no more than 20 of the amino acid residues in the sequence are so changed.

These truncated forms of METRNL comprise a core sequence from the first to the last conserved cysteine. In a preferred embodiment, less than 15 amino acids have been changed, more preferably less than 10 amino acids, more preferably less than 5 amino acids, such as 1 or 2 amino acids, more preferably no amino acids have been changed.

Variants can differ from naturally occurring METRNL in amino acid sequence or in ways that do not involve sequence, or in both ways. Variants in amino acid sequence ("sequence variants") are produced when one or more amino acids in naturally occurring METRNL is substituted with a different natural amino acid, an amino acid derivative or non-native amino acid. Particularly preferred variants include naturally occurring METRNL, or biologically active fragments of naturally occurring METRNL, whose sequences differ from the wild type sequence by one or more conservative and/or semi-conservative amino acid substitutions, which typically have minimal influence on the secondary and tertiary structure and hydrophobic nature of the protein or peptide. Variants may also have sequences, which differ by one or more non-conservative amino acid substitutions, deletions or insertions, which do not abolish the METRNL biological activity. The Clustal W alignment in FIG. 1 and/or FIG. 2 can be used to predict which amino acid residues can be substituted without substantially affecting the biological activity of the protein.

Substations within the following groups (Clustal W, 'strong' conservation group) are to be regarded as conservative substitutions within the meaning of the present invention STA, NEQK, NHQK, NDEQ, QHRK, MILV, MILF, HY, FYW.

Substations within the following groups (Clustal W, 'weak' conservation group) are to be regarded as semi-conservative substitutions within the meaning of the present invention
CSA, ATV, SAG, STNK, STPA, SGND, SNDEQK, NDEQHK, NEQHRK, VLIM, HFY.

Other variants within the invention are those with modifications which increase peptide stability. Such variants may contain, for example, one or more nonpeptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D-instead of L-amino acids into the polypeptide may increase its resistance to proteases. See, e.g., U.S. Pat. No. 5,219,990. Splice variants are specifically included in the invention.

One particularly preferred mutation is the substitution of the N-terminal Gln residue found in all mature METRNL sequences (see e.g. FIG. 3) for another amino acid selected from the group consisting of naturally occurring amino acids except Gln and Cys. Preferably the residue is mutated into a non-hydrophobic residue. More preferably the residue is mutated into Asn, or Ala. These N-terminally mutated METRNL polypeptide avoid cyclisation of the N-terminal Gln residue into pyroglutamic acid. This cyclisation has the result that the polypeptide cannot be subjected to routine N-terminal sequencing.

When the result of a given substitution cannot be predicted with certainty, the derivatives may be readily assayed according to the methods disclosed herein to determine the presence or absence of biological activity. Preferably in the DRG and/or the SVZ assays.

In one embodiment, the polypeptide is a naturally occurring allelic variant of the sequence selected from the group consisting of SEQ ID No. 2, 4, and 6. This polypeptide may comprise an amino acid sequence that is the translation of a nucleic acid sequence differing by a single nucleotide from a nucleic acid sequence selected from the group consisting of SEQ ID No. 1, 3, and 5.

A variant polypeptide as described herein, in one embodiment comprises a polypeptide wherein any amino acid specified in the chosen sequence is changed to provide a conservative substitution.

The signal peptide may be replaced by a heterologous signal peptide.

Variants within the scope of the invention in one embodiment include proteins and peptides with amino acid sequences having at least 60 percent identity with human, murine or rat METRNL (SEQ ID NO: 2, 4, and 6). More preferably the sequence identity is at least 65%, more preferably at least 70%, more preferably at least 75%, more preferably at least 80%, more preferably at least 85%, more preferably at least 90%, more preferably at least 95%, more preferably at least 98%.

Preferred variants within the scope of the invention in one embodiment include proteins and peptides with amino acid sequences having at least 60 percent identity with a polypeptide having the sequence of SEQ ID NO: 7, 8, and 9. More preferably the sequence identity is at least 65%, more preferably at least 70%, more preferably at least 75%, more preferably at least 80%, more preferably at least 85%, more preferably at least 90%, more preferably at least 95%, more preferably at least 98%. SEQ ID No 7, 8, and 9 correspond to the mature proteins after cleavage of the signal peptide. Preferably the N-terminal glutamine residue has been converted into a pyrrolidone carboxylic acid.

Variants within the scope of the invention in one embodiment include proteins and peptides with amino acid sequences having at least 60 percent identity with a polypeptide having the sequence of SEQ ID NO: 10, 11, and 12. More preferably the sequence identity is at least 65%, more preferably at least 70%, more preferably at least 75%, more preferably at least 80%, more preferably at least 85%, more preferably at least 90%, more preferably at least 95%, more preferably at least 98%.

In a preferred embodiment the sequence identity of the variant METRNL is determined with reference to a human METRNL polypeptide (SEQ ID No 2, 7, or 10).

For the purposes of determining homology the minimum length of comparison sequences will generally be at least 8 amino acid residues, usually at least 12 amino acid residues. For the purposes of the present invention, the percent sequence identity is preferably calculated in a range of overlap of at least 25 amino acids, more preferably at least 30 amino acids, more preferably at least 35, more preferably at least 40, more preferably at least 45, more preferably at least 50, more preferably at least 55, more preferably at least 60, such as at least 70, for example at least 80, such as at least 90, for example at least 100, such as at least 110, for example at least 120, such as at least 130, for example at least 150, the range being determined by BLASTP under default settings.

In one embodiment the percent sequence identity is calculated using global alignment (GAP or Align), so that the variant and SEQ ID sequences are aligned, the total number of identical amino acid residues calculated and divided by the length of the SEQ ID NO.

In one embodiment, a variant METRNL comprises a naturally occurring allelic variant of the sequence selected from the group consisting of SEQ ID No 2, 4, and 6. Said allelic variant sequence may be an amino acid sequence that is the translation of a nucleic acid sequence differing by a single nucleotide from a nucleic acid sequence selected from the group consisting of SEQ ID No 1, 3, and 5.

In one embodiment, the variants include proteins comprising an amino acid sequence having at least 60% sequence identity to SEQ ID NO 7, more preferably at least 65%, more preferably at least 70%, more preferably at least 75%, more preferably at least 80%, more preferably at least 85%, more preferably at least 90%, more preferably at least 95%, more preferably at least 98%.

In one embodiment, preferred variants include proteins comprising an amino acid sequence having at least 60% sequence identity to SEQ ID NO 8, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 9, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 2, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the variants include proteins comprising an amino acid sequence having at least 60% sequence identity to SEQ ID NO 7, more preferably at least 65%, more preferably at least 70%, more preferably at least 75%, more preferably at least 80%, more preferably at least 85%, more preferably at least 90%, more preferably at least 95%, more preferably at least 98%.

In one embodiment, the preferred variants include proteins comprising an amino acid sequence having at least 60% sequence identity to SEQ ID NO 10, more preferably at least 65%, more preferably at least 70%, more preferably at least 75%, more preferably at least 80%, more preferably at least 85%, more preferably at least 90%, more preferably at least 95%, more preferably at least 98%.

In one embodiment, a variant METRNL at corresponding positions comprises the residues marked in FIG. 1 or 2 as fully conserved (*), more preferably a variant METRNL also comprises at corresponding positions the residues that are strongly conserved (strongly conserved groups include: STA, NEQK, NHQK, NEDQ, QHRK, MILV, MILF, HY FYW), more preferably a variant METRNL also comprises at corresponding positions the residues being less conserved (less conserved groups include: CSA, ATV, SAG, STNK, STPA, SGND, SNDEQK, NDEQHK, NEQHK, NEQHRK, VLIM, HFY). In particular, it is contemplated that the conserved cysteines (FIG. 2) must be located at corresponding positions maintaining the spacing found in wildtype METRNL in a variant METRNL.

Non-sequence modifications may include, for example, in vivo or in vitro chemical derivatisation of portions of naturally occurring METRNL, as well as acetylation, methylation, phosphorylation, carboxylation, sulfation, amino acid conjugation, GSH conjugation, oxidation, reduction, hydrolysis, PEG-ylation, or glycosylation. Just as it is possible to replace substituents of the protein, it is also possible to substitute functional groups, which are bound to the protein with groups characterized by similar features. Such modifications do not alter primary sequence. These will initially be conservative, i.e., the replacement group will have approximately the same size, shape, hydrophobicity and charge as the original group.

Many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, Proteins-Structure and Molecular Properties, 2nd Ed., W. H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Seifter et al., Meth. Enzymol. 182: 626-646, 1990 and Rattan et al., Protein Synthesis: Posttranslational Modifications and Aging, Ann. N.Y. Acad. Sci. 663: 48-62, 1992.

In addition, the protein may comprise a protein tag to allow subsequent purification and optionally removal of the tag using an endopeptidase. The tag may also comprise a protease cleavage site to facilitate subsequent removal of the tag. Non-limiting examples of affinity tags include a polyhis tag, a GST tag, a HA tag, a Flag tag, a C-myc tag, a HSV tag, a V5 tag, a maltose binding protein tag, a cellulose binding domain tag. Preferably for production and purification, the tag is a polyhistag. Preferably, the tag is in the C-terminal portion of the protein, such as at the very C-terminal.

The native signal sequence of METRNL may also be replaced in order to increase secretion of the protein in recombinant production in other mammalian cell types.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well and are all within the scope of the present invention.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

Also included within the invention are agents, which specifically bind to a protein of the invention, or a fragment of such a protein. These agents include Ig fusion proteins and antibodies (including single chain, double chain, Fab fragments, and others, whether native, humanized, primatized, or chimeric). Additional descriptions of these categories of agents are in WO 95/16709, the disclosure of which is herein incorporated by reference.

Antibodies refer to intact molecules as well as fragments thereof, such as Fab, F(ab'), and Fv, which are capable of binding the epitopic determinant. Antibodies that bind METRNL polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

Humanised antibodies, as used herein, refer to antibody molecules in which amino acids have been replaced in the non-antigen binding regions in order to more closely resemble a human antibody, while still retaining the original binding ability. Humanised antibodies may be used therapeutically to treat conditions, where it is desirable to limit or block the action of METRNL.

Also included within the scope of the present invention are immunoconjugates of antibodies and conjugates selected from the group consisting of: a cytotoxic agent such as a chemotherapeutic agent, a toxin, or a radioactive isotope; a member of a specific binding pair, such as avidin, or streptavidin, or an antigen; an enzyme capable of producing a detectable product. These immunoconjugates can be used to target the conjugates to cells expressing a METRNL receptor.

Specific antibodies to any METRNL are also useful in immunoassays to quantify the substance for which a given antibody has specificity. Specific antibodies to an METRNL may also be bound to solid supports, such as beads or dishes, and used to remove the ligand from a solution, either for use in purifying the protein or in clearing it from the solution. Each of these techniques is routine to those of skill in the immunological arts.

Also with the scope of the present invention are METRNL fusion proteins. An METRNL fusion protein can be used to allow imaging of tissues which express a receptor for METRNL, or in the immunohistological or preparative methods described above for antibodies to an METRNL. Fusion proteins encompassing an METRNL can be used to specifically target medical therapies against cells, which express an METRNL receptor.

II. METRNL Nucleotide Sequences

The invention provides medical use of cDNA coding for METRNL, including for example the nucleotide sequence of human, mouse and rat METRNL cDNA (SEQ ID NO 1, 3, and 5,), the sequences coding for METRNL (SEQ ID NO 13, 14, and 15), and the sequences coding for METRNL without signal peptide (SEQ ID NO 16 or nucleotides 136-936 of SEQ ID No 1, SEQ ID NO 17 or nucleotides 136-936 of SEQ ID No. 3, and SEQ ID NO 18 or nucleotides 136-936 of SEQ ID No. 5).

Variants of these sequences are also included within the scope of the present invention.

The invention relates to an isolated nucleic acid molecule for medical use comprising a nucleic acid sequence encoding a polypeptide or its complementary sequence, said polypeptide comprising an amino acid sequence selected from the group consisting of:
a) the amino acid sequence selected from the group consisting of SEQ ID No. 2, 4, 6, 7, 8, 9, 10, 11, and 12;
b) a sequence variant of the amino acid sequence selected from the group consisting of SEQ ID No. 2, 4, 6, 7, 8, 9, 10, 11, and 12, wherein the variant has at least 70% sequence identity to said SEQ ID No.; and
c) a biologically active fragment of at least 50 contiguous amino acids of any of a) through b).
d) a biologically active sequence variant of the fragment of c), wherein the sequence variant has at least 70% sequence identity to the fragment.

The nucleic acid molecule may comprise the nucleotide sequence of a naturally occurring allelic nucleic acid variant.

The nucleic acid molecule of the invention may encode a variant polypeptide, wherein the variant polypeptide has the polypeptide sequence of a naturally occurring polypeptide variant.

In one embodiment the nucleic acid molecule differs by a single nucleotide from a nucleic acid sequence selected from the group consisting of SEQ ID No. 1, 3, 5, 13, 14, 15, 16, 17, and 18.

Preferably the encoded polypeptide has at least 60% sequence identity to a sequence selected from the group consisting of SEQ ID No. 2, 7, and 10 preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID No.s. Said sequences constitute human METRNL.

In a preferred embodiment the encoded polypeptide has at least 60% sequence identity to a sequence selected from the group consisting of SEQ ID No. 4, 8, and 11, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID No.s. Said sequences constitute mouse METRNL.

In a preferred embodiment the encoded polypeptide has at least 60% sequence identity to a sequence selected from the group consisting of SEQ ID No. 6, 9, and 12, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID No.s. Said sequences constitute rat METRNL.

In a preferred embodiment the encoded polypeptide has at least 60% sequence identity to a sequence selected from the group consisting of SEQ ID No. 7, 8, and 9, preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID No.s. Said sequences constitute mature METRNL.

In a preferred embodiment the encoded polypeptide has at least 70% sequence identity to SEQ ID No. 7, more preferably at least 75%, more preferably at least 80%, more preferably at least 95%, more preferably at least 98%, more preferably wherein said polypeptide has the sequence of SEQ ID No. 7.

In a preferred embodiment the encoded polypeptide has at least 70% sequence identity to SEQ ID No. 2, more preferably at least 75%, more preferably at least 80%, more preferably at least 95%, more preferably at least 98%, more preferably wherein said polypeptide has the sequence of SEQ ID No. 2.

In a preferred embodiment the encoded polypeptide has at least 70% sequence identity to SEQ ID No. 10, more preferably at least 75%, more preferably at least 80%, more preferably at least 95%, more preferably at least 98%, more preferably wherein said polypeptide has the sequence of SEQ ID No. 10.

In one aspect the nucleic acid molecule comprises a nucleotide sequence selected from the group consisting of
a) the nucleotide sequence selected from the group consisting of SEQ ID No. 1, 3, 5, 13, 14, 15, 16, 17, and 18;
b) a nucleotide sequence having at least 70% sequence identity to a nucleotide sequence selected from the group consisting of SEQ ID No. 1, 3, 5, 13, 14, 15, 16, 17, and 18;
c) a nucleic acid sequence of at least 150 contiguous nucleotides of a sequence selected from the group consisting of SEQ ID No. 1, 3, 5, 13, 14, 15, 16, 17, and 18;
c) the complement of a nucleic acid capable of hybridising with nucleic acid having the sequence selected from the group consisting of SEQ ID No. 1, 3, 5, 13, 14, 15, 16, 17, and 18 under conditions of high stringency; and
d) the nucleic acid sequence of the complement of any of the above.

SEQ ID No 7, 8 and 9 represent the sequences coding for mature METRNL polypeptides from human, mouse and rat. For recombinant expression in a eukaryotic expression system, these are preferably ligated to appropriate signal sequence coding sequences to ensure that the METRNL polypeptide is secreted from the cells. The same applies for recombinant expression of polypeptides defined by SEQ ID NO 10, 11, and 12.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of SEQ ID NO: 1, 3, and 5.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of SEQ ID NO: 13, 14, and 15.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence selected from the group consisting of SEQ ID NO: 16, 17, and 18.

In one embodiment, the isolated polynucleotide of the invention has at least 60, more preferably at least 65%, more preferably at least 70%, more preferably at least 75%, more preferably at least 80%, preferably at least 85%, more preferred at least 90%, more preferred at least 95%, more preferred at least 98% sequence identity to the polynucleotide sequence presented as SEQ ID NO: 1.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 13.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 16.

A preferred group of isolated polynucleotides include SEQ ID No 1, 13, and 16, which are human METRNL polynucleotides. Another preferred group of isolated polynucleotides include SEQ ID No. 1, 3, and 5, which represent the cDNA sequences.

In addition, the nucleotide sequences of the invention include sequences, which are derivatives of these sequences. The invention also includes vectors, liposomes and other carrier vehicles, which encompass one of these sequences or a derivative of one of these sequences. The invention also includes proteins transcribed and translated from METRNL cDNA, preferably human METRNL cDNA, including but not limited to human METRNL and fragments and variants.

In another embodiment, the invention relates to the use of the nucleic acids and proteins of the present invention to design probes to isolate other genes, which encode proteins with structural or functional properties of the METRNL proteins of the invention. The probes can be a variety of base pairs in length. For example, a nucleic acid probe can be between about 10 base pairs in length to about 150 base pairs in length.

Alternatively, the nucleic acid probe can be greater than about 150 base pairs in length. Experimental methods are provided in Ausubel et al., "Current Protocols in Molecular Biology", J. Wiley (ed.) (1999), the entire teachings of which are herein incorporated by reference in their entirety.

The design of the oligonucleotide (also referred to herein as nucleic acid) probe should preferably follow these parameters:
i) it should be designed to an area of the sequence which has the fewest ambiguous bases, if any and
ii) it should be designed to have a calculated Tm of about 80° C. (assuming 2° C. for each A or T and 4° C. for each G or C).

The oligonucleotide should preferably be labeled to facilitate detection of hybridisation. Labelling may be with $\gamma$-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4×106 dpm/pmole. The bacterial culture containing the pool of full-length clones should preferably be thawed and 100 μL of the stock used to inoculate a sterile culture flask containing 25 ml of sterile L-broth containing ampicillin at 100 pg/ml.

The culture should preferably be grown to saturation at about 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 pg/ml and agar at 1.5% in a 150 mm petri dish when grown overnight at about 37° C. Other known methods of obtaining distinct, well-separated colonies can also be employed.

Standard colony hybridization procedures should then be used to transfer the colonies to nitrocellulose filters and lyse, denature and bake them. Highly stringent (also referred to herein as "high stringency") conditions are those that are at least as stringent as, for example, 1×SSC at about 65° C., or 1×SSC and 50% formamide at about 42° C. "Moderate stringency" conditions are those that are at least as stringent as 4×SSC at about 65° C., or 4×SSC and 50% formamide at about 42° C. "Reduced stringency" conditions are those that are at least as stringent as 4×SSC at about 50° C., or 6×SSC and 50% formamide at 40° C.

The filter is then preferably incubated at about 65° C. for 1 hour with gentle agitation in 6×SSC (20× stock is 175.3 g NaCl/liter, 88.2 g Na citrate/liter, adjusted to pH 7.0 with NaOH) containing 0.5% SDS, 100 g/ml of yeast RNA, and 10 mM EDTA (approximately 10 mL per 150 mm filter). Preferably, the probe is then added to the hybridization mix at a concentration greater than or equal to 1×106 dpm/mL. The filter is then preferably incubated at about 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at about 65° C. for 30 minutes to 1 hour is optional. The filter is then preferably dried and subjected to autoradiography for sufficient time to visualize the positives on the X-ray film. Other known hybridization methods can also be employed. The positive colonies are then picked, grown in culture, and plasmid DNA isolated using standard procedures. The clones can then be verified by restriction analysis, hybridisation analysis, or DNA sequencing.

Alternatively, suitable experimental conditions for determining hybridization between a nucleotide probe and a homologous DNA or RNA sequence, involves pre-soaking of the filter containing the DNA fragments or RNA to hybridize in 5×SSC [Sodium chloride/Sodium citrate; cf. Sambrook et al.; Molecular Cloning: A Laboratory Manual, Cold Spring Harbor Lab., Cold Spring Harbor, N.Y. 1989] for 10 minutes, and pre-hybridization of the filter in a solution of 5×SSC, 5×Denhardt's solution [cf. Sambrook et al.; Op cit.], 0.5% SDS and 100 μg/ml of denatured sonicated salmon sperm DNA [cf. Sambrook et al.; Op cit.], followed by hybridization in the same solution containing a concentration of 10 ng/ml of a random-primed [Feinberg A P & Vogelstein B; Anal. Biochem. 1983 132 6-13], 32P-dCTP-labeled (specific activity >1×109 cpm/μg) probe for 12 hours at approximately 45° C. The filter is then washed twice for 30 minutes in 0.1×SSC, 0.5% SDS at a temperature of at least at least 60° C. (medium stringency conditions), preferably of at least 65° C. (medium/high stringency conditions), more preferred of at least 70° C. (high stringency conditions), and even more preferred of at least 75° C. (very high stringency conditions). Molecules to which the oligonucleotide probe hybridizes under these conditions may be detected using a x-ray film.

In yet another embodiment, the invention relates to nucleic acid sequences (e.g., DNA, RNA) that hybridise to nucleic acids of METRNL. In particular, nucleic acids which hybridise to SEQ ID NO: 1, SEQ ID NO: 3, SEQ ID NO: 5, SEQ ID NO: 13, SEQ ID No. 14, SEQ ID No. 15, SEQ ID No 16, SEQ ID No 17, or SEQ ID No 18 under high, moderate or reduced stringency conditions as described above.

In still another embodiment, the invention relates to a complement of nucleic acid of METRNL. In particular, it relates to complements of SEQ ID NO: 1, SEQ ID NO: 3, SEQ ID NO: 5, SEQ ID NO: 13, SEQ ID No. 14, SEQ ID No. 15, SEQ ID No 16, SEQ ID No 17, or SEQ ID No 18.

In another embodiment, the invention relates to an RNA counterpart of the DNA nucleic acid of METRNL. In particular, it relates to RNA counterparts of SEQ ID NO: 1, SEQ ID NO: 3, SEQ ID NO: 5, SEQ ID NO: 13, SEQ ID No. 14, SEQ ID No. 15, SEQ ID No 16, SEQ ID No 17, or SEQ ID No 18. Similarly the use of LNA or PNA counterparts of said SEQ ID No is contemplated.

Codon optimised nucleic acid molecules for enhanced expression in selected host cells, including but not limited to *E. coli*, yeast species, Chinese Hamster, Baby Hamster, insect, and fungus are also contemplated.

Variant nucleic acids can be made by state of the art mutagenesis methods. Methods for shuffling coding sequences from human with those of mouse, rat or chimpanzee are also contemplated. Specifically a shuffled variant may be between SEQ ID No 1 on one hand and 3 and/or 5 on the other hand. Also included are shuffled variants between SEQ ID No 3 and 5.

III. Use of METRNL Polypeptides, Polynucleotides, and METRNL Secreting Cells for Treatment of Disorders of the Nervous System In one embodiment, native, variant METRNL, and fragments thereof and/or fusion proteins comprising METRNL are provided for the treatment of disorders of the mammalian nervous system. METRNL may be used to stimulate neural cell growth including proliferation, neural function, neural regeneration, neural differentiation, neural migration, and/or neural survival in disease situations where these cells are lost or damaged.

In one embodiment, polynucleotides and/or polypeptides of the invention may be used to treat conditions or diseases where neural growth including proliferation, differentiation, function, migration, survival, and/or regeneration is desirable. The polypeptides of the present invention may be used directly via, e.g., injected, implanted or ingested pharmaceutical compositions to treat a pathological process responsive to the METRNL polypeptides.

This is supported by the fact that the secreted growth factor METRNL is capable of protecting Guinea Pigs against neurotoxin-induced hearing loss (Example 2A), the fact that the secreted growth factor METRNL is capable of inducing neurite outgrowth (axonal extension) and stimulate survival in rat P5 dorsal root ganglions (Example 2), and the fact that METRNL stimulates migration of neuroblasts from subventricular zone explants (Example 2). The survival, regeneration, neurogenesis, differentiation and in particular the neuromigratory effects of METRNL make it a candidate protein/gene for treatment of nervous system disorders involving loss or damage to neural cells. Such disorders include stroke, trauma and neurodegenerative disorders as well as to a disease, disorder, or damage involving the sensory epithelium and associated ganglia of the inner ear, noise induced hearing loss, deafness, tinnitus, otitis, labyrintitis, hereditary and cochleovestibular atrophies, and Meniere's Disease. The neuroprotective and/or neurogenesis and/or neuromigratory effect of METRNL supports the use for treating disorders caused by loss, dysfunction, or degeneration of neurons or their processes.

METRNL may act on a range of different cell types, which are present in the nervous system. In the context of the present invention, the nervous system is intended to encompass the central nervous system, the peripheral nervous system, the eye, and the inner ear.

In one embodiment, METRNL polypeptides may act on neurons, including but not limited to motor neurons and sensory neurons.

In another embodiment, the therapeutic effect of METRNL polypeptides may be through action on Schwann cells and glial cells, such as oligodendrocytes and/or astrocytes. Through their action on Schwann cells and glial cells, METRNL polypeptides may be involved in myelination, and in the maintenance of neuron function and survival.

In another embodiment, METRNL polypeptides may act on sensory cells, including but not limited to retinal ganglion cells, photoreceptor cells, supportive tissue such as retinal epithelial cells, and spiral ganglion cells, and hair cells of the ear.

In a further embodiment, METRNL polypeptides may act on stem cells, and their neural progeny including but not limited to neural and neuronal precursors and glial precursors.

METRNL polypeptides may act on stem cells and/or neuronal or glial precursors to cause growth including proliferation, to cause differentiation, and/or migration. Stem cell therapy (including therapy of neural progeny) may be done through in vivo or ex vivo gene therapy, or the protein may be administered to a location with endogenous or transplanted stem cells or ex vivo to stem cells isolated from a patient.

The disorder or disease or damage may be damages of the nervous system caused by trauma, surgery, ischaemia, infection, metabolic diseases, nutritional deficiency, malignancy or toxic agents, and genetic or idiopathic processes.

In one embodiment of the method of the invention, the disease or disorder or damage involves injury to the brain, brain stem, the spinal cord, and/or peripheral nerves, resulting in conditions such as stroke, traumatic brain injury (TBI), spinal cord injury (SCI), diffuse axonal injury (DAI), epilepsy, neuropathy, peripheral neuropathy, and associated pain and other symptoms that these syndromes may cause.

In another embodiment, the disease, disorder, or damage involves the degeneration of neurons and their processes in the brain, brain stem, the spinal cord, and/or peripheral nerves, such as neurodegenerative disorders including but not limited to Parkinson's Disease, Alzheimer's Disease, senile dementia, Huntington's Disease, amyotrophic lateral sclerosis (ALS), neuronal/axonal injury associated with Multiple Sclerosis (MS), and associated symptoms.

In another embodiment, the disease, disorder, or damage involves dysfunction, and/or loss of neurons in the brain, brain stem, the spinal cord, and/or peripheral nerves, such as dysfunction and/or loss caused by metabolic diseases, nutritional deficiency, toxic injury, malignancy, and/or genetic or idiopathic conditions, including but not limited to diabetes, renal dysfunction, alcoholism, chemotherapy, chemical agents, drug abuse, vitamin deficiencies, infection, and associated symptoms.

In another embodiment, the disease, disorder, or damage involves the degeneration or sclerosis of glia such as oligodendrocytes, astrocytes, and Schwann cells in the brain, brain stem, the spinal cord, and peripheral nervous system, including but not limited to Multiple Sclerosis (MS), optic neuritis, cerebral sclerosis, post-infectious encephalomyelitis, and epilepsy, and associated symptoms.

In another embodiment, the disease, disorder, or damage involves the retina, photoreceptors, and associated nerves including but not limited to retinitis pigmentosa, macular degeneration, glaucoma, and associated symptoms.

In another embodiment, the disease, disorder, or damage involves the sensory epithelium and associated ganglia of the inner ear, including but not limited to noise induced hearing loss, deafness, tinnitus, otitis, labyrintitis, hereditary and cochleovestibular atrophies, Meniere's Disease, and associated symptoms. An in vivo effect on deafened Guinea Pigs has been demonstrated by the present inventors in Example 2A. The damage to the sensory epithelium and associated ganglia of the inner ear may be the result of surgery carried out on the inner ear, such as the implantation of an implant, stapedectomy, Mastoidectomy, and tympanoplasty. The implant may be a cochlear implant, a middle ear implant, a Bone-anchored hearing aid, and an auditory brainstem implant. Thus the inventors contemplate administration of METRNL in connection with surgery on the inner ear. The inventors further contemplate coating of ear implants, such as cochlear implants, middle ear implants, Bone-anchored hearing aids, and auditory brainstem implants with a METRNL protein formulation to protect against neuronal damage and stimulate recovery following surgery. A further relevant model for verifying the effect of METRNL on spiral ganglion cells is Warnecke et al., "The biological effects of cell-delivered brain-derived neurotrophic factor on cultured spiral ganglion cells". Neuroreport. 2007 Oct. 29; 18(16):1683-6.

In a preferred embodiment, the polypeptides, nucleic acids, expression vectors, capsules and pharmaceutical compositions of the invention are used in the treatment of Parkinson's Disease. This function is based on the fact that METRNL causes neurogenesis and/or migration of neural cells in SVZ explants. The function can be verified using the Bioassay for dopaminergic neurotrophic activities (example 6) and in vivo through the instrastriatal 6-OHDA lesion model (Example 7).

Huntington's disease (HD) is an autosomal dominant disorder that results in the progressive degeneration of various neuronal populations within the brain, particularly the GABA-ergic medium spiny neurons located in the caudate nucleus. Associated with this degeneration, the cortical glutaminergic input neurons also degenerate and the combined degeneration account for most of the characteristic symptoms of progressive dyskinetic motor movements as well as dementia.

In a preferred embodiment, the polypeptides, nucleic acids, expression vectors, capsules and pharmaceutical compositions of the invention are used in the treatment of Huntington's disease. This function is based on the fact that METRNL causes neurogenesis and/or migration of neural cells in SVZ explants. Huntington's disease is an excitotoxic disease. An excitotoxic in vitro bioassay is the assay described in Example 3 of the present invention. Another exemplary bioassay for verification of this neuroprotective effect of METRNL include e.g. the bioassay on protection of primary hippocampal slice cultures against the excitotoxic effects of NMDA (WO 03/004527, example 5). Preferred animal models for verification of the function are described in Anderson et al, 1996. Proc Natl Acad Sci USA.; 93(14): 7346-7351 or in Pereira de Almeidab et al, 2001 Neurobiology of Disease. Volume 8, Issue 3, 433-446.

In another preferred embodiment, the polypeptides, nucleic acids, expression vectors, capsules and pharmaceutical compositions of the invention are used in the treatment of peripheral neuropathies. This is based on the finding of neurotrophic/differentiation/regeneration effect on rat P5 DRGs (Example 2). Among the peripheral neuropathies contemplated for treatment with the molecules of this invention are trauma-induced neuropathies, e.g., those caused by physical injury or disease state, physical damage to the peripheral nerves such as hermited discs, and the brain, physical damage to the spinal cord, stroke associated with brain damage, and neurological disorders related to neurodegeneration. We also contemplate treatment of chemotherapy-induced neuropathies (such as those caused by delivery of chemotherapeutic agents, e.g., taxol or cisplatin); toxin-induced neuropathies, drug-induced neuropathies, vitamin-deficiency-induced neuropathies; idiopathic neuropathies; infectious neuropathies such as post-herpatic neuralgia, and diabetic neuropathies. The effect can be verified in an animal model described in Gardell et al, 2003 Nat Med.; 9(11):1383-9.

In another preferred embodiment the polypeptides, nucleic acids, expression vectors, capsules, and compositions of the invention are used in the treatment of disorders, diseases, or damages associated with diseases, damage or trauma associated with nerve roots and peripheral nerves, such as root avulsion, root injury, and brachial plexus injury. This is based on the finding of neurotrophic/differentiation/regeneration effect on rat P5 DRG cultures (Example 2). The effect on root avulsuion or root injury can be verified using an animal model described in Wang et al, 2008 Nat Neurosci. 11(4):488-96. Another animal model has been described by Hanna-Mitchell et al, 2008. The impact of neurotrophin-3 on the dorsal root transitional zone following injury. Spinal Cord. 2008 Jun. 10. Epub ahead of print.

In another embodiment, the polypeptides, nucleic acids, expression vectors, capsules, and compositions of the invention are used in the treatment of disorders, diseases, or damages associated with the Cerebellum, including but not limited to sensory ataxia, multiple sclerosis, neurodegenerative spinocerebellar disorders, hereditary ataxia, cerebellar atrophies (such as Olivopontocerebellar Atrophy (OPCA), Shy-Drager Syndrome (multiple systems atrophy)), and alcoholism. This function is supported by the general neurotrophic effects of METRNL (Examples 2). Verification of this function may be done with the assays described in Examples 3 and 4 (Protection of cerebellar granule cells from glutamate toxicity and potassium deprivation).

In another preferred embodiment, the polypeptides, nucleic acids, expression vectors, capsules and pharmaceutical compositions of the invention are used in the treatment of amyotrophic lateral sclerosis, spinal muscular atrophy, and spinal cord injury (e.g. ischemic or traumatic). This is based on neuromigratory/neurotrophic/neuroprotective/neurogenesis activity of METRNL (DRG and SVZ assay of Example 2). Verification of this specific therapeutic function may be done with the motorneuron assay described in example 5.

In a preferred embodiment, the polypeptides, nucleic acids, vectors, capsules, and compositions of the invention are used in the treatment of diseases, disorders, or damages involving the retina, including but not limited to retinitis pigmentosa, macular degeneration and glaucoma.

Other growth factors have important therapeutic uses in both the central and peripheral nervous system and in various eye indications associated with loss of cells in retina and/or cornea. E.g NGF, is a candidate for both Alzheimer's disease, corneal ulcer (U.S. Pat. No. 6,063,757 and EP 0 973 872), and retinopathies. Neublastin (Artemin) is a candidate for both peripheral neuropathy (WO 02/078730) and corneal wound healing (EP 1 223 966). GDNF is a candidate for Parkinson's Disease, ALS, spinal cord injury, and for wound healing, in particular in cornea (EP 1 223 966).

Confirmation of such use can be obtained by using various state of the art in vitro assays (retinal explant assays, corneal cultures). Verification of function may also be performed in state of the art animal models for corneal wounds (corneal lesion in rabbits) and retina (retinitis pigmentosa mutant models available for mouse and rat).

In another embodiment the neurodegenerative disease is an excitotoxic disease selected from the group consisting of ischaemia, epilepsy (in particular focal epilepsy in hippocampus), and trauma due to injury, cardiac arrest or stroke. This function is also supported by the neurotrophic/neuromigratory/neuroprotective/neurogenesis activity of METRNL (Examples 2). The above-mentioned hippocampal slice culture assay and the assay of Example 3 of the present invention are non-limiting examples of an assay, which can be used to demonstrate a biological effect, indicative of therapeutic use for the treatment of excitotoxic diseases.

The term "subject" used herein is taken to mean any mammal to which METRNL polypeptide or polynucleotide, therapeutic cells or biocompatible capsules may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

IV. Polypeptide Administration and Formulations

A target tissue for METRNL therapy is a region of the brain selected for its retained responsiveness to METRNL. In humans, neurons, which retain responsiveness to growth factors into adulthood include the cholinergic basal forebrain neurons, the entorhinal cortical neurons, the thalamic neurons, the locus coeruleus neurons, the spinal sensory neurons, the spinal motor neurons, neurons of substantia nigra, sympathetic neurons, dorsal root ganglia, retina neurons, otic neurons, cerebellar neurons, and ciliary ganglia. Stem cells, such as stem cells of the subventricular zone, and neural and glial progenitor cells also retain responsiveness to growth factors into adulthood. Also myelinating oligodendrocytes retain responsiveness to growth factors into adulthood.

METRNL polypeptides may be administered in any manner, which is medically acceptable. This may include injections, by parenteral routes such as intravenous, intravascular, intraarterial, subcutaneous, intramuscular, intratumor, intraperitoneal, intraventricular, intraepidural, intertracheal, intrathecal, intracerebroventricular, intercerebral, interpulmonary, or others as well as nasal, ophthalmic, rectal, or topical. Sustained release administration is also specifically included in the invention, by such means as depot injections or erodible implants. Peroral administration is also conceivable provided the protein is protected against degradation in the stomach.

Administration of an METRNL according to this invention may be achieved using any suitable delivery means, including:

pump (see, e.g., Annals of Pharmacotherapy, 27:912 (1993); Cancer, 41:1270 (1993); Cancer Research, 44:1698 (1984), incorporated herein by reference), microencapsulation (see, e.g., U.S. Pat. Nos. 4,352,883; 4,353,888; and 5,084,350, herein incorporated by reference), continuous release polymer implants (see, e.g., Sabel, U.S. Pat. No. 4,883,666, incorporated herein by reference), encapsulated cells expressing METRNL (see, Section IX), naked or unencapsulated cell grafts expressing METRNL to the CNS (see, e.g., U.S. Pat. Nos. 5,082,670 and 5,618,531, each incorporated herein by reference);

injection, either subcutaneously, intravenously, intra-arterially, intramuscularly, or to other suitable site;

suppository;

inhalation; and oral administration, in capsule, liquid, tablet, pill, or prolonged release formulation.

Administration may be by periodic injections of a bolus of the preparation, or may be made more continuous by intravenous or intraperitoneal administration from a reservoir which is external (e.g., an IV bag) or internal (e.g., a bioerodable implant, a bioartificial organ, a biocompatible capsule of METRNL production cells, or a colony of implanted METRNL production cells). See, e.g., U.S. Pat. Nos. 4,407, 957, 5,798,113, and 5,800,828, each incorporated herein by reference. Intrapulmonary delivery methods and apparatus are described, for example, in U.S. Pat. Nos. 5,654,007, 5,780,014, and 5,814,607, each incorporated herein by reference.

Apart from systemic delivery, delivery directly to the CNS or the eye behind the blood-brain or blood-retina barriers is also contemplated.

Localised delivery may be by such means as delivery via a catheter to one or more arteries, such as the ophthalmic artery to the eye, and the cerebral artery to the CNS. Localised delivery to the eye may be in the form of topical application to the cornea or direct intravitreal injection of protein or virus vector. Methods for local pump-based delivery of protein formulations to the CNS are described in U.S. Pat. No. 6,042, 579 (Medtronic). The in vivo experiments of the present application (example 2A) is one example of localised protein delivery, in this case to the inner ear. Another type of localised delivery comprises delivery using encapsulated cells (see Section IX). A further type of localised delivery comprises local delivery of gene therapy vectors, which are normally injected.

For the treatment of eye disorders, delivery may be systemic, or local such as delivery via the ophthalmic artery. In another embodiment, delivery is via Encapsulated Cell Therapy, where the encapsulated cells are implanted intravitreally. Delivery of protein formulations or gene therapy vector may be done using subretinal injections, intravitreal injection, or transcleral injection.

For the treatment of Parkinson's Disease, various delivery routes can be taken. Protein formulations can be administered with pumps intracerbroventricularly or intraparenchymally, preferably to the striatum and/or substantia nigra, more preferably to the intraputamen. However, a more preferred delivery method comprises encapsulated cell therapy, where the capsulses are implanted intracerebroventricularly, or intraparenchymally, preferably into the striatum, and/or substantia nigra, and more preferably into the putamen. In one embodiment relating to treatment of Parkinson's Disease, gene therapy vector is administered to the striatum of the brain. Injection into the striatum can label target sites located in various distant regions of the brain, for example, the globus pallidus, amygdala, subthalamic nucleus or the substantia nigra. Transduction of cells in the pallidus commonly causes retrograde labelling of cells in the thalamus. In a preferred embodiment the (or one of the) target site(s) is the substantia nigra.

In an embodiment to treat HD, METRNL is applied to the striatum, preferably the caudate nucleus in order to protect the neurons from degeneration, resulting in both protection of the caudate neurons and the cortical input neurons. In a preferred embodiment, the application should occur before the onset of major degenerative changes. The treatment would involve the genetic diagnosis of the disease through family history and DNA analysis of the blood followed by the local application of METRNL. This would be accomplished by delivering the METRNL to the striatum via pumping of the protein with the use of medically applicable infusion pumps and catheters, e.g. Medtronic Synchrotron pump. In a second strategy, direct gene therapy using viral or non-viral vectors could be utilized to modify the host cells in the striatum or other affected neurons to secrete METRNL. In a third strategy, naked or encapsulated cells genetically modified to make and secrete METRNL can be applied locally to deliver METRNL behind the blood-brain-barrier and within the diseased region, preferably the striatum, even more preferred, the caudate nucleus.

For the treatment of root avulsion, root injury or peripheral nerve injury including brachial plexus injury, METRNL can be administered systemically, intrathecally directly into the dorsal root entry zone or localised in affected dermatomes.

In ALS, both upper and lower motor neurons degenerate, causing progressive paralyses, eventually leading to death, most commonly through respiratory complications. Administration using a viral vector such as AAV coding for METRNL into cells of the motorcortex that project into the cortical spinal tract, the spinocerebellar tract, or the rubral cerebellar tract is also contemplated. To treat ALS, METRNL would be delivered to the CNS including the spinal cord through the infusion of METRNL into the lumbar intrathecal space thereby mixing with the cerebrospinal fluid (CSF), which bathes the spinal cord and brain. The delivery could be accomplished through the implantation of pump and catheters, e.g. Medtronic Synchrotron pump or through the use of encapsulated cell devices implanted into the lumbar inthrathecal space. Direct gene therapy could also be used by injecting DNA carrying vectors into the CSF, thereby transferring the gene to cells lining the CSF space. In addition, gene transfer vectors can be injected into the cervical or lumbar spinal cord or intracerebral, thereby secreting METRNL in the anatomical regions containing the majority of the motor neurons involved in motor paralyses and respiratory function. These injections would occur under surgical navigation and could be performed relatively safely.

In subjects with neurodegenerative diseases such as AD, neurons in the Ch4 region (nucleus basalis of Meynert) which have nerve growth factor (NGF) receptors undergo marked atrophy as compared to normal controls (see, e.g., Kobayashi, et al., Mol. Chem. Neuropathol., 15: 193-206 (1991)).

In normal subjects, neurotrophins prevent sympathetic and sensory neuronal death during development and prevents cholinergic neuronal degeneration in adult rats and primates (Tuszynski, et al., Gene Therapy, 3 : 305314 (1996)). The resulting loss of functioning neurons in this region of the basal forebrain is believed to be causatively linked to the cognitive decline experienced by subjects suffering from neurodegenerative conditions such as AD (Tuszynski, et al., supra; Lehericy, et al., J. Comp. Neurol., 330: 15-31 (1993)).

In general it is contemplated, that AD can be treated with METRNL protein formulations delivered intracerebroventricularly, or intraparenchymally. Within the intraparenchymal area, delivery is preferably to the basal forebrain, and to the hippocampus.

Gene therapy vector, encapsulated or naked cells secreting METRNL can also be administered to the basal forebrain or the hippocampus.

For the treatment of a disorder, disease, or damage involving the sensory epithelium and associated ganglia of the vestibuloacoustic complex including but not limited to noise-induced hearing loss, deafness, tinnitus, otitis, labyrintitis, hereditary and cochleovestibular atrophies, Menieres Disease, protein, gene therapy vector or encapsulated or naked cells secreting METRNL to the inner ear is contemplated. One example of this is described in the examples (Example 2A).

For the treatment of spinal cord injury, protein, gene therapy vector or encapsulated or naked cells secreting METRNL can be delivered intrathecally at the position of the injury as described above for the treatment of ALS.

For the treatment of peripheral neuropathy, delivery is either systemic (using protein formulations), intrathecally using protein formulations, gene therapy vectors, or encapsulated or naked cells secreting METRNL, or intramuscularly depending on retrograde transport to the spinal cord.

For the treatment of epilepsy METRNL protein could be delivered intraparenchymally in the epilepsy focus. This may be done with encapsulated or naked cells, with protein formulation administered with catheter or pump or with gene therapy vector delivered to this site.

For the treatment of stroke or trauma, delivery is intrathecal, intracerbroventricular, or preferably intralessionar.

The term "pharmaceutically acceptable carrier" means one or more organic or inorganic ingredients, natural or synthetic, with which METRNL polypeptide is combined to facilitate its application. A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

A liposome system may be any variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637, 4,762,915, 5,000,958 or 5,185,154. In addition, it may be desirable to express the novel polypeptides of this invention, as well as other selected polypeptides, as lipoproteins, in order to enhance their binding to liposomes. A recombinant METRNL protein is purified, for example, from CHO cells by immunoaffinity chromatography or any other convenient method, then mixed with liposomes and incorporated into them at high efficiency. The liposome-encapsulated protein may be tested in vitro for any effect on stimulating cell growth.

Any of the METRNL polypeptides of this invention may be used in the form of a pharmaceutically acceptable salt. Suitable acids and bases which are capable of forming salts with an METRNL polypeptide are well known to those of skill in the art, and include inorganic and organic acids and bases.

In addition to the active ingredients, the pharmaceutical compositions may comprise suitable ingredients. Further details on techniques for formulation and administration may be found in the latest edition of Remington's Pharmaceutical Sciences (Maack Publishing Co., Easton, Pa.).

Various dosing regimes for systemic administration are contemplated. In one embodiment, methods of administering to a subject a formulation comprising an METRNL polypeptide include administering METRNL at a dosage of between 1 µg/kg to 30,000 µg/kg body weight of the subject, per dose.

In another embodiment, the dosage is between 10 µg/kg to 30,000 µg/kg body weight of the subject, per dose. In a further embodiment, the dosage is between 10 µg/kg to 10,000 µg/kg body weight of the subject, per dose. In a different embodiment, the dosage is between 25 µg/kg to 10,000 µg/kg body weight of the subject, per dose. In yet another embodiment, the dosage is between 25 µg/kg to 3,000 µg/kg body weight of the subject, per dose. In a most preferable embodiment, the dosage is between 50 µg/kg to 3,000 µg/kg body weight of the subject, per dose.

Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of an METRNL polypeptide is desired in a formulation with release characteristics suitable for the treatment of any disease or disorder requiring administration of an METRNL polypeptide, microencapsulation of an METRNL polypeptide is contemplated. Microencapsulation of recombinant proteins for sustained release has been successfully performed with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Flora et al., Bio/Technology, 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

The dose administered must be carefully adjusted to the age, weight and condition of the individual being treated, as well as the route of administration, dosage form and regimen, and the result desired, and the exact dosage should be determined by the practitioner.

V. Pharmaceutical Preparations for Gene Therapy

To form an METRNL composition for gene therapy use in the invention, METRNL encoding expression viral vectors may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. Further, a composition of METRNL transgenes may be lyophilized using means well known in the art, for subsequent reconstitution and use according to the invention.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6: 77, 1981). In addition to mammalian cells, liposomes have been used for delivery of operatively encoding transgenes in plant, yeast and bacterial cells. In order for a liposome to be an efficient gene transfer vehicle, the following characteristics should be present: (1) encapsulation of the genes encoding the METRNL at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6: 682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries.

Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further example of a delivery system includes transplantation into the therapeutic area of a composition of packaging cells capable of producing vector particles as described in the present invention. Methods for encapsulation and transplantation of such cells are known in the art, in particular from WO 97/44065 (Cytotherapeutics). By selecting a packaging cell line capable of producing lentiviral particles, transduction of non-dividing cells in the therapeutic area is obtained. By using retroviral particles capable of transducing only dividing cells, transduction is restricted to de-novo differentiated cells in the therapeutic area.

VI. Dosing Requirements and Delivery Protocol for Gene Therapy

An important parameter is the dosage of METRNL gene therapy vector to be delivered into the target tissue. For viral vectors, the concentration may be defined by the number of transducing units/ml. Optimally, for delivery using a viral expression vector, each unit dosage will comprise 2.5 to 25 µL of a composition, wherein the composition includes a viral expression vector in a pharmaceutically acceptable fluid and provides from $10^8$ up to $10^{10}$ METRNL transducing units per ml.

Importantly, specific in vivo gene delivery sites are selected so as to cluster in an area of loss, damage, or dysfunction of neural cells, glial cells, retinal cells, sensory cells, or stem cells. Such areas may be identified clinically using a number of known techniques, including magnetic resonance imaging (MRI) and biopsy. In humans, non-invasive, in vivo imaging methods such as MRI will be preferred. Once areas of neuronal loss are identified, delivery sites are selected for stereotaxic distribution so each unit dosage of METRNL is delivered into the brain at, or within 500 µm from, a targeted cell, and no more than about 10 mm from another delivery site.

Within a given target site, the vector system may transduce a target cell. The target cell may be a cell found in nervous tissue, such as a neuron, astrocyte, oligodendrocyte, microglia, stem cells, neural precursor cells, or ependymal cell.

The vector system is preferably administered by direct injection. Methods for injection into the brain are well known in the art (Bilang-Bleuel et al (1997) Proc. Acad. Natl. Sci. USA 94:8818-8823; Choi-Lundberg et al (1998) Exp. Neurol. 154:261-275; Choi-Lundberg et al (1997) Science 275: 838-841; and Mandel et al (1997)) Proc. Acad. Natl. Sci. USA 94:14083-14088). Stereotaxic injections may be given.

As mentioned above, for transduction in tissues such as the brain, it is necessary to use very small volumes, so the viral preparation is concentrated by ultracentrifugation. The resulting preparation should have at least $10^8$ TU/ml, preferably from $10^8$ to $10^{10}$ TU/ml, more preferably at least $10^9$ TU./ml. (The titer is expressed in transducing units per ml (TU./ml)). It has been found that improved dispersion of transgene expression can be obtained by increasing the number of injection sites and decreasing the rate of injection (Horellou and Mallet (1997) as above). Usually between 1 and 10 injection sites are used, more commonly between 2 and 6. For a dose comprising $1-5 \times 10^9$ TU./ml, the rate of injection is commonly between 0.1 and 10 µl/min, usually about 1 µl/min.

The virus composition is delivered to each delivery cell site in the target tissue by microinjection, infusion, scrape loading, electroporation or other means suitable to directly deliver the composition directly into the delivery site tissue through a surgical incision. The delivery is accomplished slowly, such as over a period of about 5-10 minutes (depending on the total volume of virus composition to be delivered).

VII. Viral Vectors

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells (including but not limited to stem cells, neural and glial precursor cells, and foetal stem cells), which are then infused, grafted or otherwise transplanted into the patient. See, e.g., U.S. Pat. Nos. 4,868,116, 5,399,346 and 5,460,959. In vivo gene therapy seeks to directly target host patient tissue.

Viruses useful as gene transfer vectors include papovavirus, adenovirus, vaccinia virus, adeno-associated virus, herpesvirus, and retroviruses. Suitable retroviruses include the group consisting of HIV, SIV, FIV, EIAV, MoMLV. A further group of suitable retroviruses includes the group consisting of HIV, SIV, FIV, EAIV, CIV. Another group of preferred virus vectors includes the group consisting of alphavirus, adenovirus, adeno associated virus, baculovirus, HSV, coronavirus, Bovine papilloma virus, Mo-MLV, preferably adeno associated virus.

Preferred viruses for treatment of disorders of the nervous system are lentiviruses and adeno-associated viruses. Both types of viruses can integrate into the genome without cell divisions, and both types have been tested in pre-clinical animal studies for indications of the nervous system, in particular the central nervous system.

Methods for preparation of AAV are described in the art, e.g. U.S. Pat. Nos. 5,677,158. 6,309,634 and U.S. Pat. No. 6,683,058 describe examples of delivery of AAV to the central nervous system.

Preferably, a lentivirus vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR. Methods for preparation and in vivo administration of lentivirus to neural cells are described in US 20020037281 (Methods for transducing neural cells using lentiviral vectors).

Retroviral vectors are the vectors most commonly used in human clinical trials, since they carry 7-8 kb and since they have the ability to infect cells and have their genetic material stably integrated into the host cell with high efficiency. See, e.g., WO 95/30761; WO 95/24929. Oncovirinae require at least one round of target cell proliferation for transfer and integration of exogenous nucleic acid sequences into the patient. Retroviral vectors integrate randomly into the patient's genome. Retroviruses can be used to target stem cells of the nervous system as very few cell divisions take place in other cells of the nervous system (in particular the CNS).

Three classes of retroviral particles have been described; ecotropic, which can infect murine cells efficiently, and amphotropic, which can infect cells of many species. The third class includes xenotrophic retrovirus which can infect cells of another species than the species which produced the virus. Their ability to integrate only into the genome of dividing cells has made retroviruses attractive for marking cell lineages in developmental studies and for delivering therapeutic or suicide genes to cancers or tumors.

For use in human patients, the retroviral vectors must be replication defective. This prevents further generation of infectious retroviral particles in the target tissue. Instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7-8 kb.

Replication defective retroviral vectors require provision of the viral proteins necessary for replication and assembly in trans, from, e.g., engineered packaging cell lines. It is important that the packaging cells do not release replication competent virus and/or helper virus. This has been achieved by expressing viral proteins from RNAs lacking the ψ signal, and expressing the gag/pol genes and the env gene from separate transcriptional units. In addition, in some 2. and 3. generation retroviruses, the 5' LTR's have been replaced with non-viral promoters controlling the expression of these genes, and the 3' promoter has been minimised to contain only the proximal promoter. These designs minimize the possibility of recombination leading to production of replication competent vectors, or helper viruses.

VIII. Expression Vectors

Construction of vectors for recombinant expression of METRNL polypeptides for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982). Expression vectors may be used for generating producer cells for recombinant production of METRNL polypeptides for medical use, and for generating therapeutic cells secreting METRNL polypeptides for naked or encapsulated therapy.

Briefly, construction of recombinant expression vectors employs standard ligation techniques. For analysis to confirm correct sequences in vectors constructed, the genes are sequenced using, for example, the method of Messing, et al., (Nucleic Acids Res., 9: 309-, 1981), the method of Maxam, et al., (Methods in Enzymology, 65: 499, 1980), or other suitable methods which will be known to those skilled in the art.

Size separation of cleaved fragments is performed using conventional gel electrophoresis as described, for example, by Maniatis, et al., (Molecular Cloning, pp. 133-134, 1982).

For generation of efficient expression vectors, these should contain regulatory sequences necessary for expression of the encoded gene in the correct reading frame. Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al. 1981, Cell 27: 299; Corden et al. 1980, Science 209: 1406; and Breathnach and Chambon 1981, Ann. Rev. Biochem. 50: 349). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al. 1983, Nucleic Acids Res. 11: 1855; Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al. 1985, Nature 314: 285; Rossi and deCrombrugghe 1987, Proc. Natl. Acad. Sci. USA 84: 5590-5594). Methods for maintaining and increasing expression of transgenes in quiescent cells include the use of promoters including collagen type I (1 and 2) (Prockop and Kivirikko, 1984 N. Eng. J. Med. 311: 376; Smith and Niles 1980, Biochem. 19: 1820; de Wet et al. 1983, J. Biol. Chem., 258: 14385), SV40 and LTR promoters.

According to one embodiment of the invention, the promoter is a constitutive promoter selected from the group consisting of: ubiquitin promoter, CMV promoter, JeT promoter (U.S. Pat. No. 6,555,674), SV40 promoter, Chicken beta-action promoter, Elongation Factor 1 alpha promoter (EF1-alpha), RSV, Mo-MLV-LTR. Examples of inducible/repressible promoters include: Tet-On, Tet-Off, Rapamycin-inducible promoter, Mx1.

A group of preferred promoters include Chicken beta-actin promoter, CMV, human UbiC, JeT, RSV, Tet-regulatable promoter, Mo-MLV-LTR, Mx1, and EF-1 alpha.

In addition to using viral and non-viral promoters to drive transgene expression, an enhancer sequence may be used to increase the level of transgene expression. Enhancers can increase the transcriptional activity not only of their native gene but also of some foreign genes (Armelor 1973, Proc. Natl. Acad. Sci. USA 70: 2702). For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al. 1981, Proc. Natl. Acad. Sci. USA 78: 943; Benoist and Chambon 1981, Nature 290: 304, and Fromm and Berg 1982, J. Mol. Appl. Genetics, 1: 457, all of which are incorporated by reference herein. This repeat sequence can increase the transcription of many different viral and cellular genes when it is present in series with various promoters (Moreau et al. 1981, Nucleic Acids Res. 9: 6047).

Further expression enhancing sequences include but are not limited to Woodchuck hepatitis virus post-transcriptional regulation element, WPRE, SP163, CMV enhancer, and Chicken [beta]-globin insulator or other insulators.

Transgene expression may also be increased for long term stable expression using cytokines to modulate promoter activity. Several cytokines have been reported to modulate the expression of transgene from collagen 2 (I) and LTR promoters (Chua et al., connective Tissue Res., 25: 161-170 (1990); Elias et al., Annals N.Y. Acad. Sci., 580: 233-244 (1990)); Seliger et al., J. Immunol. 141: 2138-2144 (1988) and Seliger et al., J. Virology 62: 619-621 (1988)). For example, transforming growth factor (TGF), interleukin (IL)-I, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll (E)) may also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll (E) promoter-enhancer, and reduces transgene expression.

The vector may comprise further sequences such as a sequence coding for the Cre-recombinase protein, and LoxP sequences. A further way of ensuring temporary expression of the METRNL is through the use of the Cre-LoxP system which results in the excision of part of the inserted DNA sequence either upon administration of Cre-recombinase to the cells (Daewoong et al, Nature Biotechnology 19:929-933) or by incorporating a gene coding for the recombinase into the virus construct (Pluck, Int J Exp Path, 77:269-278). Incorporating a gene for the recombinase in the virus construct together with the LoxP sites and a structural gene (an METRNL in the present case) often results in expression of the structural gene for a period of approximately five days.

IX. Biocompatible Capsules

Encapsulated cell therapy is based on the concept of isolating cells from the recipient host's immune system by surrounding the cells with a semipermeable biocompatible material before implantation within the host. The invention includes a device in which cells capable of expressing and secreting METRNL are encapsulated in an immunoisolatory capsule. An "immunoisolatory capsule" means that the capsule, upon implantation into a recipient host, minimizes the deleterious effects of the host's immune system on the cells in the core of the device. Cells are immunoisolated from the host by enclosing them within implantable polymeric capsules formed by a microporous membrane. This approach prevents the cell-to cell contact between host and implanted tissues, eliminating antigen recognition through direct presentation. The membranes used can also be tailored to control the diffusion of molecules, such as antibody and complement, based on their molecular weight (Lysaght et al., 56 J. Cell Biochem. 196 (1996), Colton, 14 Trends Biotechnol. 158 (1996)). Using encapsulation techniques cells can be transplanted into a host without immune rejection, either with or without use of immunosuppressive drugs. Useful biocompatible polymer capsules usually contain a core that contains cells, either suspended in a liquid medium or immobilized within an immobilizing matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue.

The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors such as METRNL polypeptides, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described in WO 92/19195 or WO 95/05452, incorporated by reference; or U.S. Pat. Nos. 5,639,275; 5,653,975; 4,892,538; 5,156,844; 5,283,187; or U.S. Pat. No. 5,550,050, incorporated by reference. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the genetically altered cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene terephthalate, nylon, polyamides, polyurethanes, polybutester, silk, cotton, chitin, carbon, or biocompatible metals. Also, bonded fiber structures can be used for cell implantation (U.S. Pat. No. 5,512,600, incorporated by reference). Biodegradable polymers include those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (WO 98/05304, incorporated by reference). Woven mesh tubes have been used as vascular grafts (WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. No. 4,976,859 or U.S. Pat. No. 4,968,733, incorporated by reference. An alternate surrounding semipermeable membrane material is poly(acrylonitrile/covinyl chloride).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

When macrocapsules are used, preferably between $10^3$ and $10^8$ cells are encapsulated, most preferably $10^5$ to $10^7$ cells are encapsulated in each device. Dosage may be controlled by implanting a fewer or greater number of capsules, preferably between 1 and 10 capsules per patient.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see, WO 97/34586, incorporated by reference).

Methods and apparatus for implantation of capsules into the CNS are described in U.S. Pat. No. 5,487,739. Methods and apparatus for implantation of capsules into the eye are described in U.S. Pat. Nos. 5,904,144, 6,299,895, 6,439,427, and US 20030031700.

In one aspect the invention relates to a biocompatible capsule comprising: a core comprising living packaging cells that secrete a viral vector for infection of a target cell, wherein the viral vector is a vector according to the invention; and an external jacket surrounding said core, said jacket comprising a permeable biocompatible material, said material having a porosity selected to permit passage of retroviral vectors of approximately 100 nm diameter thereacross, permitting release of said viral vector from said capsule.

Preferably, the core additionally comprises a matrix, the packaging cells being immobilized by the matrix. According to one embodiment, the jacket comprises a hydrogel or thermoplastic material.

Examples of suitable cells for packaging cell lines include HEK293, NIH3T3, PG13, and ARPE-19 cells. Preferred cells include PG13 and 3T3 cells.

Packaging cell lines may be encapsulated and administered using the methods and compositions disclosed in U.S. Pat. No. 6,027,721 and WO 97/01357 hereby incorporated by reference in their entirety.

X. Support Matrix for METRNL Producing Cells

The present invention further comprises culturing METRNL producing cells in vitro on a support matrix prior to implantation into the mammalian nervous system. The preadhesion of cells to microcarriers prior to implantation is designed to enhance the long-term viability of the transplanted cells and provide long term functional benefit.

To increase the long term viability of the transplanted cells, i.e., transplanted METRNL secreting cells, the cells to be transplanted can be attached in vitro to a support matrix prior to transplantation. Materials of which the support matrix can be comprised include those materials to which cells adhere following in vitro incubation, and on which cells can grow, and which can be implanted into the mammalian body without producing a toxic reaction, or an inflammatory reaction which would destroy the implanted cells or otherwise interfere with their biological or therapeutic activity. Such materials may be synthetic or natural chemical substances, or substances having a biological origin.

The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amylases, natural and modified gelatin and natural and codified collagen, natural and modified polysaccharides, including dextrans and celluloses (e.g., nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of RPE cells. Thus, for example, the matrix material may be extracellular matrix or basement membrane material, which is produced and secreted by RPE cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors.

Alternatively, if the solid matrix to which the implanted cells are attached is constructed of porous material, the growth- or survival promoting factor or factors may be incorporated into the matrix material, from which they would be slowly released after implantation in vivo.

When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead.

Bead sizes may range from about 10 µm to 1 mm in diameter, preferably from about 90 µm to about 150 µm. For a description of various microcarrier beads, see, for example, isher Biotech Source 87-88, Fisher Scientific Co., 1987, pp. 72-75; Sigma Cell Culture Catalog, Sigma Chemical Co., St, Louis, 1991, pp. 162-163; Ventrex Product Catalog, Ventrex Laboratories, 1989; these references are hereby incorporated by reference. The upper limit of the bead's size may be dictated by the bead's stimulation of undesired host reactions, which may interfere with the function of the transplanted cells or cause damage to the surrounding tissue. The upper limit of the bead's size may also be dictated by the method of administration. Such limitations are readily determinable by one of skill in the art.

XI. Host Cells

In one aspect the invention relates to isolated host cells genetically modified with the vector according to the invention.

According to one embodiment, the host cells are prokaryotic cells such as *E. coli* which are capable producing recombinant protein in high quantities and which can easily be scaled up to industrial scale. The use of prokaryotic producer cells may require refolding and glycosylation of the METRNL in order to obtain a biologically active protein. In another embodiment, the host cells are eukaryotic producer cells from non-mammals, including but not limited to known producer cells such as yeast (*Saccharomyces cerevisiae*), filamentous fungi such as *aspergillus*, and insect cells, such as Sf9

According to another embodiment, the cells preferably are mammalian host cells because these are capable of secreting and processing the encoded METRNL correctly. Preferred species include the group consisting of human, feline, porcine, simian, canina, murine, rat, rabbit, mouse, and hamster.

Examples of primary cultures and cell lines that are good candidates for transduction or transfection with the vectors of the present invention include the group consisting of CHO, CHO-K1, HEI193T, HEK293, COS, PC12, HiB5, RN33b, neuronal cells, foetal cells, ARPE-19, C2C12, MDX12, HeLa, HepG2, striatal cells, neurons, astrocytes, and interneurons. Preferred cell lines for mammalian recombinant production include CHO, CHO-1, HEI193T, HEK293, COS, PC12, HiB5, RN33b, and BHK cells.

For ex vivo gene therapy, the preferred group of cells include neuronal cells, neuronal precursor cells, neuronal progenitor cells, stem cells and foetal cells.

The invention also relates to cells suitable for biodelivery of METRNL via naked or encapsulated cells, which are genetically modified to overexpress METRNL, and which can be transplanted to the patient to deliver bioactive METRNL polypeptide locally. Such cells may broadly be referred to as therapeutic cells.

In a preferred embodiment of the invention, a therapeutic cell line has not been immortalised with the insertion of a heterologous immortalisation gene. As the invention relates to cells which are particularly suited for cell transplantation, whether as naked cells or—preferably as encapsulated cells, such immortalised cell lines are less preferred as there is an inherent risk that they start proliferating in an uncontrolled manner inside the human body and potentially form tumours.

Preferably, the cell line is a contact inhibited cell line. By a contact inhibited cell line is intended a cell line which when grown in 2-D cultures grow to confluency and then substantially stop dividing. This does not exclude the possibility that a limited number of cells escape the 2D layer. Contact inhibited cells may also be grown in 3D, e.g. inside a capsule. Also inside the capsules, the cells grow to confluency and then significantly slow down proliferation rate or completely stop dividing. A particularly preferred type of cells include epithelial cells which are by their nature contact-inhibited and which form stable monolayers in culture.

Even more preferred are retinal pigment epithelial cells (RPE cells). The source of RPE cells is by primary cell isolation from the mammalian retina. Protocols for harvesting RPE cells are well-defined (Li and Turner, 1988, Exp. Eye Res. 47:911-917; Lopez et al., 1989, Invest. Ophthalmol. Vis. Sci. 30:586-588) and considered a routine methodology. In most of the published reports of RPE cell cotransplantation, cells are derived from the rat (Li and Turner, 1988; Lopez et al., 1989). According to the present invention RPE cells are derived from humans. In addition to isolated primary RPE cells, cultured human RPE cell lines may be used in the practice of the invention.

For encapsulation, the cells need to be able to survive and maintain a functional METRNL secretion at the low oxygen tension levels of the CNS. Preferably the cell line of the invention is capable of surviving at an oxygen tension below 5%, more preferably below 2%, more preferably below 1%. 1% oxygen tension corresponds approximately to the oxygen level in the brain.

To be a platform cell line for an encapsulated cell based delivery system, the cell line should have as many of the following characteristics as possible: (1) The cells should be hardy under stringent conditions (the encapsulated cells should be functional in the vascular and avascular tissue cavities such as in the central nervous system intraparenchymally or within the ventricular or intrathecal fluid spaces or the eye, especially in the intra-ocular environment). (2) The cells should be able to be genetically modified to express METRNL. (3) The cells should have a relatively long life span (the cells should produce sufficient progenies to be banked, characterised, engineered, safety tested and clinical lot manufactured). (4) The cells must be of human origin (which increases compatibility between the encapsulated cells and the host). (5) The cells should exhibit greater than 80% viability for a period of more than one month in vivo in device (which ensures long-term delivery). (6) The encapsulated cells should deliver an efficacious quantity of METRNL (which ensures effectiveness of the treatment). (7) when encapsulated the cells should not cause a significant host immune reaction (which ensures the longevity of the graft). (8) The cells should be non-tumorigenic (to provide added safety to the host, in case of device leakage).

For encapsulation the preferred cells include retinal pigmented epithelial cells, including ARPE-19 cells; human immortalised fibroblasts; and human immortalised astrocytes.

The ARPE-19 cell line is a superior platform cell line for encapsulated cell based delivery technology and is also useful for unencapsulated cell based delivery technology. The ARPE-19 cell line is hardy (i.e., the cell line is viable under stringent conditions, such as implantation in the central nervous system or the intra-ocular environment). ARPE-19 cells can be genetically modified to secrete a substance of therapeutic interest. ARPE-19 cells have a relatively long life span. ARPE-19 cells are of human origin. Furthermore, encapsulated ARPE-19 cells have good in vivo device viability. ARPE-19 cells can deliver an efficacious quantity of growth factor. ARPE-19 cells elicit a negligible host immune reaction. Moreover, ARPE-19 cells are non-tumorigenic. Methods for culture and encapsulation of ARPE-19 cells are described in U.S. Pat. No. 6,361,771.

In another embodiment the therapeutic cell line is selected from the group consisting of: human fibroblast cell lines, human astrocyte cell lines, human mesencephalic cell line, and human endothelial cell line, preferably immortalised with TERT, SV40T or vmyc.

The method for generating an immortalised human astrocyte cell lines has previously been described (Price T N, Burke J F, Mayne L V. A novel human astrocyte cell line (A735) with astrocyte-specific neurotransmitter function. In Vitro Cell Dev Biol Anim. 1999 May; 35(5):279-88.). This protocol may be used to generate astrocyte cell lines.

The following three modifications of that protocol are preferably made to generate additional human astrocyte cell lines.

Human foetal brain tissue dissected from 5-12 weeks old foetuses may be used instead of 12-16 weeks old tissue.

The immortalisation gene v-myc, or TERT (telomerase) may be used instead of the SV40 T antigen.

Retroviral gene transfer may be used instead of transfection with plasmids by the calcium phosphate precipitation technique.

XII. Recombinant Production and Purification of METRNL Polypeptides of the Invention The METRNL polypeptides of the invention may be produced using state of the art prokaryotic or eukaryotic expression systems. A eukaryotic expression system is described in Example 2 resulting in a substantially purified his-tagged MERTNL polypeptide.

Further exemplary methods are described in WO 93/22437 (Innogenetics), which is hereby incorporated by reference. The protocols described in WO 93/22437 describe purification of a protein having a predicted molecular weight of 29 kDa. In the case of expression of METRNL fragments, which may be considerably shorter, the protocols should be modified to take the difference in molecular weight into consideration.

These examples include expression in E. coli (Example 5 of WO 93/22437), expression in COS1 cells (Example 6 of WO 93/22437), expression in a baculovirus expression system (Example 7 of WO 93/22437), expression in a vaccinia virus system (Example 8 of WO 93/22437). Each of the referenced expression systems resulted in the expression of significant amounts of the polypeptides described in WO 93/22437.

Purification of METRNL proteins may be performed using the purification method described in WO 93/22437. Briefly, conditioned medium of COS1 cells transfected with the cDNA of the invention is collected after 48 h and filtered over a 0.22 μm filter to remove cell debris. A typical purification starts from 600 to 1000 ml of COS1 transfection medium. To this MgCl2 and dextrane-sulphate 500.000 (Pharmacia, Uppsala, Sweden) is added to a final concentration of 60 mM and 0.02%, respectively. After 1 h incubation at 4° C. the precipitate is pelleted by centrifugation (12.000 g, 30 min., 4° C.). The supernatant fraction, containing the METRNL is dialysed against 50 mM Hepes pH 7.0, 4 mM EDTA, adjusted to pH 8.0 and loaded at a flowrate of 0.5 ml/minute on a 4 ml Phenylboronate agarose (PBA 30, Amicon, Mass., USA) column equilibrated in 50 mM Hepes pH 8.5. The METRNL is eluted from the matrix by 100 mM Sorbitol.

The Sorbitol eluated peak is then passed at a flowrate of 0.5 ml/minute over a 1 ml FPLC Mono Q anion exchange column (Pharmacia) equilibrated in Hepes pH 8.5 and eluted with a linear salt gradient of 0 to 1 M NaCl at a flowrate of 1 ml/minute.

The eluate is concentrated about 40 fold by Centricon 10.000 (Amicon) and loaded batchwise (3 times 0.25 ml) on a SMART Superdex 75 gelfiltration column (Pharmacia) equilibrated against PBS. This protocol may result in elution of protein of high purity.

Other state of the art protein purification protocols may also be used to provide enough pure protein to perform the in vitro and in vivo assays described in the examples.

XIII. In Vitro Uses of METRNL

METRNL polypeptides and/or METRNL encoding polynucleotides may be used as growth factors or trophic factors in vitro. This use is based on the finding that METRNL is a secreted protein with structural features of a growth factor or hormone and on the finding by the present inventors that METRNL causes neurite outgrowth (axonal extension), neural survival, neurogenesis, and migration of neural precursors in different in vitro assays. The neurotrophic and/or neuromigratory and/or neuroprotective and/or neurogenesis effect has been found in dorsal root ganglions and in subventricular zone explants.

METRNL may be administered to the culture as a protein composition or the cells may be transduced or transfected with cDNA encoding METRNL. Whether METRNL would be effective in the treatment of a particular cell type or tissues can be readily determined by one skilled in the art using any of a variety of assays known in the art. For example, with respect to providing trophic support for cells, trophic factors can produce beneficial biochemical and morphological effects and, under some circumstances, can promote cell survival. With respect to neurons, it is known in the art that depriving a neuron of trophic support may result in a decrease in metabolic activity, i.e., glucose uptake, RNA synthesis and protein synthesis, required for normal function and growth (Deckwerth and Johnson 1993, J. Cell Biol. 123:1207-1222). Removal of trophic support also may result in a reduction in size of the cell body of the neuron. Presumably as a consequence of the loss of the metabolic effects of trophic factors, trophic factor deprivation may result in a decrease or cessation of process outgrowth and may result in retraction of neuronal processes. In addition to the requirement of trophic factor for these aspects of neuronal biology, the neuron may require the neurotrophic factor to maintain survival; thus, survival assays are a frequently used means to detect or quantitate the actions of a neurotrophic factor. However, trophic support can also be manifest as morphological, biochemical, and functional changes; independent of neuronal number or any effect on survival.

METRNL protein or polynucleotides may be used for propagation, differentiation, regeneration, or survival of stem cells and their neural progeny as well as neurons, glial cell, Schwann cells, astrocytes, oligodendocytes. The in vitro culture may be part of stimulation or ex vivo gene therapy of cell isolated from a patient and intended for subsequent administration to the patient after ex vivo stimulation or transfection/transduction.

XIV Anti-METRNL Antibodies

METRNL polypeptides or polypeptide fragments of the invention are used to produce METRNL-specific antibodies. As used herein, a "METRNL-specific antibody" is an antibody, e.g., a polyclonal antibody or a monoclonal antibody, that is immunoreactive to a METRNL polypeptide or polypeptide fragment, or that binds with specificity to an epitopes of a METRNL polypeptide.

The preparation of polyclonal and monoclonal antibodies is well known in the art. Polyclonal antibodies may in particular be obtained as described by, e.g., Green et al.,: "Production of Polyclonal Antisera" in *Immunochemical Protocols* (Manson, Ed.); Humana Press, 1992, pages 1-5; by Coligan et al.,: "Production of Polyclonal Antisera in Rabbits, Rats, Mice and Hamsters" in *Current Protocols in Immunology*, 1992, Section 2.4.1, and by Ed Harlow and David Lane (Eds.) in *"Antibodies; A laboratory manual"* Cold Spring Harbor Lab. Press 1988. Monoclonal antibodies may in particular be obtained as described by, e.g., Kohler & Milstein, *Nature*, 1975, 256:495; Coligan et al., in *Current Protocols in Immunology*, 1992, Sections 2.5.1-2.6.7; and Harlow et al., in *Antibodies: A Laboratory Manual*; Cold Spring Harbor, Pub., 1988, page 726. Briefly, monoclonal antibodies may be obtained by injecting, e.g., mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce the antibodies to the antigen, and isolating the antibodies from the hybridoma cultures. Monoclonal antibodies can be isolated and purified from hybridoma cultures by a variety of well-established techniques, including affinity chromatography with protein A Sepharose, size-exclusion chromatography, and ion-exchange chromatography, see. e.g. Coligan et al. in *Current Protocols in*

*Immunology*, 1992, Sections 2.7.1-2.7.12, and Sections 2.9.1-2.9.3; and Barnes et al.: "Purification of Immunoglobulin G (IgG)" in *Methods in Molecular Biology*; Humana Press, 1992, Vol. 10, Pages 79-104. Polyclonal or monoclonal antibodies may optionally be further purified, e.g. by binding to and elution from a matrix to which the polypeptide, to which the antibodies were raised, is bound.

Antibodies which bind to the METRNL polypeptide of the invention can be prepared using an intact polypeptide or fragments containing small peptides of interest as the immunising antigen. The polypeptide used to immunise an animal may be obtained by recombinant DNA techniques or by chemical synthesis, and may optionally be conjugated to a carrier protein. Commonly used carrier proteins which are chemically coupled to the peptide include keyhole limpet hemocyanin (KLH), thyroglobulin, bovine serum albumin (BSA), and tetanus toxoid. The coupled peptide may then be used to immunise the animal, which may in particular be a mouse, a rat, a hamster or a rabbit.

EXAMPLES

Example 1

METRNL Sequences

Sequence Listing Numbers.
SEQ ID NO 1: Human Meteorin-like cDNA
SEQ ID NO 2: Human Meteorin-like protein (incl. signal peptide)
SEQ ID NO 3: Mouse Meteorin-like cDNA
SEQ ID NO 4: Mouse Meteorin-like protein (incl. signal peptide)
SEQ ID NO 5: Rat Meteorin-like cDNA
SEQ ID NO 6: Rat Meteorin-like protein (incl. signal peptide)
SEQ ID NO 7: Human mature meteorin-like protein
SEQ ID NO 8: Mouse mature meteorin-like protein
SEQ ID NO 9: Rat mature meteorin-like protein
SEQ ID NO 10: Human meteorin-like core fragment
SEQ ID NO 11: Mouse meteorin-like core fragment
SEQ ID NO 12: Rat meteorin-like core fragment
SEQ ID NO 13: hMTRNL open reading frame
SEQ ID NO 14: mMTRNL open reading frame
SEQ ID NO 15: rMTRNL open reading frame
SEQ ID NO 16: Human CDS mature METRNL
SEQ ID NO 17: Mouse CDS mature METRNL
SEQ ID NO 18: Rat CDS mature METRNL
SEQ ID NO 19: Bovine Meteorin-like protein (incl. signal peptide)
SEQ ID NO 20: Chicken meteorin-like protein (incl. signal peptide)
SEQ ID NO 21: Frog Meteorin-like protein (incl. signal peptide)
SEQ ID NO 22: Zebrafish Meteorin-like protein (incl. signal peptide)
SEQ ID NO 23: Human METRN protein (incl. signal peptide)
SEQ ID NO 24: Mouse METRN protein (incl. signal peptide)
SEQ ID NO 25: Rat METRN protein (incl. signal peptide)
SEQ ID NO 26: C-terminal His-tag of METRNL

```
SEQ ID NO 2: Human Meteorin-like protein (NP_001004431.1)
    1   mrgaaraawg ragqpwprpp apgppppplp lllllagll ggagaqyssd 51   rcswkgsglt heahrkeveq vylrcaagav ewmyptgali vnlrpntfsp 101   arhltvcirs ftdssganiy lektgelrll vpdgdgrpgr vqcfgleqgg 151   lfveatpqqd igrrttgfqy elvrrhrasd lhelsapcrp csdtevllav 201   ctsdfavrgs iqqvtheper qdsaihlrvs rlyrqksrvf epvpegdghw 251   qgrvrtllec gvrpghgdfl ftghmhfgea rlgcaprfkd fqrmyrdaqe 301   rglnpcevgt d SEQ ID NO 4: Mouse Meteorin-like protein (NP_659046.1)
    1   mrgavwaarr ragqqwprsp gpgpgppppp pllllllll ggasaqyssd 51   lcswkgsglt rearskeveq vylrcsagsv ewmyptgali vnlrpntfsp 101   aqnltvcikp frdssganiy lektgelrll vrdirgepgq vqcfsleqgg 151   lfveatpqqd isrrttgfqy elmsgqrgld lhvlsapcrp csdtevllai 201   ctsdfvvrgf iedvthvpeq qvsviylrvn rlhrqksrvf qpapedsghw 251   lghvttllqc gvrpghgefl ftghvhfgea qlgcaprfsd fqrmyrkaee 301   mginpceinm e SEQ ID NO 6: Rat Meteorin-like protein (NP_001014126)
    1   mrgvvwaarr ragqqwprsp gpgpgppppp pllllllll ggasaqyssd 51   lcswkgsglt reahskeveq vylrcsagsv ewmyptgali vnlrpntfsp 101   aqnltvcikp frdssganiy lektgelrll vrdvrgepgq vqcfsleqgg 151   lfveatpqqd isrrttgfqy elmsgqrgld lhvlsapcrp csdtevllai 201   ctsdfvvrgf iedvthvpeq qvsvihlrvs rlhrqksrvf qpapedsghw
```

-continued

```
251  lghvttllqc gvrpghgefl ftghvhfgea qlgcaprfsd fqkmyrkaee 301  rginpceinm e
```

SEQ ID NO 7: human mature meteorin-like protein
```
QYSSDRCSWK GSGLTHEAHR KEVEQVYLRC AAGAVEWMYP TGALIVNLRP NTFSPARHLT    60

VCIRSFTDSS GANIYLEKTG ELRLLVPDGD GRPGRVQCFG LEQGGLFVEA TPQQDIGRRT   120

TGFQYELVRR HRASDLHELS APCRPCSDTE VLLAVCTSDF AVRGSIQQVT HEPERQDSAI   180

HLRVSRLYRQ KSRVFEPVPE GDGHWQGRVR TLLECGVRPG HGDFLFTGHM HFGEARLGCA   240

PRFKDFQRMY RDAQERGLNP CEVGTD                                       266
```

SEQ ID NO 8: mouse mature meteorin-like protein
```
QYSSDLCSWK GSGLTREARS KEVEQVYLRC SAGSVEWMYP TGALIVNLRP NTFSPAQNLT    60

VCIKPFRDSS GANIYLEKTG ELRLLVRDIR GEPGQVQCFS LEQGGLFVEA TPQQDISRRT   120

TGFQYELMSG QRGLDLHVLS APCRPCSDTE VLLAICTSDF VVRGFIEDVT HVPEQQVSVI   180

YLRVNRLHRQ KSRVFQPAPE DSGHWLGHVT TLLQCGVRPG HGEFLFTGHV HFGEAQLGCA   240

PRFSDFQRMY RKAEEMGINP CEINME                                       266
```

SEQ ID NO 9: rat mature meteorin-like protein
```
QYSSDLCSWK GSGLTREAHS KEVEQVYLRC SAGSVEWMYP TGALIVNLRP NTFSPAQNLT    60

VCIKPFRDSS GANIYLEKTG ELRLLVRDVR GEPGQVQCFS LEQGGLFVEA TPQQDISRRT   120

TGFQYELMSG QRGLDLHVLS APCRPCSDTE VLLAICTSDF VVRGFIEDVT HVPEQQVSVI   180

HLRVSRLHRQ KSRVFQPAPE DSGHWLGHVT TLLQCGVRPG HGEFLFTGHV HFGEAQLGCA   240

PRFSDFQKMY RKAEERGINP CEINME                                       266
```

SEQ ID NO 10: human meteorin-like core fragment
```
CSWKGSGLTH EAHRKEVEQV YLRCAAGAVE WMYPTGALIV NLRPNTFSPA RHLTVCIRSF    60

TDSSGANIYL EKTGELRLLV PDGDGRPGRV QCFGLEQGGL FVEATPQQDI GRRTTGFQYE   120

LVRRHRASDL HELSAPCRPC SDTEVLLAVC TSDFAVRGSI QQVTHEPERQ DSAIHLRVSR   180

LYRQKSRVFE PVPEGDGHWQ GRVRTLLECG VRPGHGDFLF TGHMHFGEAR LGCAPRFKDF   240

QRMYRDAQER GLNPC                                                   255
```

SEQ ID NO 11: mouse meteorin-like core fragment
```
CSWKGSGLTR EARSKEVEQV YLRCSAGSVE WMYPTGALIV NLRPNTFSPA QNLTVCIKPF    60

RDSSGANIYL EKTGELRLLV RDIRGEPGQV QCFSLEQGGL FVEATPQQDI SRRTTGFQYE   120

LMSGQRGLDL HVLSAPCRPC SDTEVLLAIC TSDFVVRGFI EDVTHVPEQQ VSVIYLRVNR   180

LHRQKSRVFQ PAPEDSGHWL GHVTTLLQCG VRPGHGEFLF TGHVHFGEAQ LGCAPRFSDF   240

QRMYRKAEEM GINPC                                                   255
```

SEQ ID NO 12: rat meteorin-like core fragment
```
CSWKGSGLTR EAHSKEVEQV YLRCSAGSVE WMYPTGALIV NLRPNTFSPA QNLTVCIKPF    60

RDSSGANIYL EKTGELRLLV RDVRGEPGQV QCFSLEQGGL FVEATPQQDI SRRTTGFQYE   120

LMSGQRGLDL HVLSAPCRPC SDTEVLLAIC TSDFVVRGFI EDVTHVPEQQ VSVIHLRVSR   180

LHRQKSRVFQ PAPEDSGHWL GHVTTLLQCG VRPGHGEFLF TGHVHFGEAQ LGCAPRFSDF   240

QKMYRKAEER GINPC                                                   255
```

SEQ ID NO 1: Human Meteorin-like cDNA (NM_001004431.1)
```
    1  gcgggggggcg cgcgacgtga ccacccggac tcgaagcccg ccccgccccc 51  gcccggctcg ccggctccgg ggtctgctcc gggggtcgcg gacgcggggc 101  cgggcggcgg agccggcgcc agagcatgcg gggcgcggcg cgggcggcct 151  ggggcgcgc ggggcagccg tggccgcgac ccccgccccc ggaccgccc 201  ccgccgccgc tcccgctgct gctcctgctc ctggccgggc tgctgggcgg
```

```
 251  cgcgggcgcg cagtactcca gcgaccggtg cagctggaag gggagcgggc
 301  tgacgcacga ggcacacagg aaggaggtgg agcaggtgta tctgcgctgt
 351  gcggcgggtg ccgtggagtg gatgtaccca acaggtgctc tcatcgttaa
 401  cctgcggccc aacaccttct cgcctgcccg gcacctgacc gtgtgcatca
 451  ggtccttcac ggactcctcg ggggccaata tttatttgga aaaaactgga
 501  gaactgagac tgctggtacc ggacggggac ggcaggcccg gccgggtgca
 551  gtgttttggc ctggagcagg gcggcctgtt cgtggaggcc acgccgcagc
 601  aggatatcgg ccggaggacc acaggcttcc agtacgagct ggttaggagg
 651  cacagggcgt cggacctgca cgagctgtct gcgccgtgcc gtccctgcag
 701  tgacaccgag gtgctcctag ccgtctgcac cagcgacttc gccgttcgag
 751  gctccatcca gcaagttacc cacgagcctg agcggcagga ctcagccatc
 801  cacctgcgcg tgagcagact ctatcggcag aaaagcaggg tcttcgagcc
 851  ggtgcccgag ggtgacggcc actggcaggg gcgcgtcagg acgctgctgg
 901  agtgtggcgt gcggccgggg catggcgact cctcttcac tggccacatg
 951  cacttcgggg aggcgcggct cggctgtgcc ccacgcttca aggacttcca
1001  gaggatgtac agggatgccc aggagagggg gctgaaccct tgtgaggttg
1051  gcacggactg actccgtggg ccgctgccct tcctctcctg atgagtcaca
1101  ggctgcggtg ggcgctgcgg tcctggtggg gccgtgcggt gagggccgcg
1151  cgctgggagc cgcatgccct gggcccaggc ctgaccctgg taccgaagct
1201  gtggacgttc tcgccacact caaccccatg agcttccagc caaggatgcc
1251  ctggccgatt ggaaatgctg taaaatgcaa actaagttat tatatttttt
1301  tttggtaaaa aagaaatgtc cataggaaac aaaaaaaaaa aaaaaaa
ORF in bold SEQ ID NO 3: Mouse Meteorin-like cDNA (NM_144797.3)
   1  agaggttcta ggggcagccg gcgcgcttct ctagttgcag cttgggcggc
  51  tcctgtggtg ggcggctagg ggcgagccgg gatgggctat agacgcgcga
 101  cgtgatcagt tcgcacgcgg acccacgcct cccatcgctc tgcctcaaga
 151  gccattctg tgggtgcagg cacgcaccgg acgcagaccc ggccggagca
 201  tgcggggtgc ggtgtgggcg gcccggaggc gcgcggggca gcagtggcct
 251  cggtccccgg gccctgggcc gggtccgccc ccgccgccac cgctgctgtt
 301  gctgctacta ctgctgctgg gcggcgcgag cgctcagtac tccagcgacc
 351  tgtgcagctg gaaggggagt gggctcaccc gagaggcacg cagcaaggag
 401  gtggagcagg tgtacctgcg ctgctccgca ggctctgtgg agtggatgta
 451  cccaactggg gcgctcattg ttaacctacg gcccaacacc ttctcacctg
 501  cccagaactt gactgtgtgc atcaagcctt tcaggactc ctctggagcc
 551  aatatttatt tggaaaaaac tggagaacta agactgttgg tgcgggacat
 601  cagaggtgag cctggccaag tgcagtgctt cagcctggag cagggaggct
 651  tatttgtgga ggcgacaccc aacaggaca tcagcagaag gaccacaggc
 701  ttccagtatg agctgatgag tgggagaggg gactggacc tgcacgtgct
 751  gtctgccccc tgtcggcctt gcagtgacac tgaggtcctc cttgccatct
 801  gtaccagtga ctttgttgtc cgaggcttca ttgaggacgt cacacatgta
 851  ccagaacagc aagtgtcagt catctacctg cgggtgaaca ggcttcacag
```

-continued

```
 901  gcagaagagc agggtcttcc agccagctcc tgaggacagt ggccactggc
 951  tgggccatgt cacaacactg ctgcagtgtg gagtacgacc agggcatggg
1001  gaattcctct tcactggaca tgtgcacttt ggggaggcac aacttggatg
1051  tgccccacgc tttagtgact ttcaaaggat gtacaggaaa gcagaagaaa
1101  tgggcataaa ccctgtgaa atcaatatgg agtgacttgc agggtgacac
1151  agtactgttg tccttcagat gagccatgtt ttgtgggctc agtcgctcta
1201  tcatatcctg atagagattg cagactggtg gcatgggccc agcctggtgc
1251  tagaactggg aaggtacatg ctgctctgac cccttaggtc ccagccaagg
1301  atgccctgac ccattggaac tgctgtaaaa tgcaaactaa gttattatat
1351  ttttttttgta aaagatgcct tggtgtgcca tttaatagtg ttttttacaaa
1401  gttattttca ggcattggat ttggcctggt atattggtgg gagctaggtt
1451  atggtgtgca gtgatggcta tggctcagcc ttgttattcc tgtgatggaa
1501  atgtatggag caaatacttt ctaatttccc cttcatttta ttttctattt
1551  taaaagacca tctttgccgt tgagaacctt tccagactgt atggaggctg
1601  ctcccattcc agggagtaaa gaccaggatc tgagactagt attacatcca
1651  tcttaaccca tcagatgggt acctgcattg aaccttctct gctcagctat
1701  ggcctgctgt cccaaagacc ttttgctctc tggacagttc cagatggtgc
1751  tgcctggctt aagggacttg ttcctccctt gctcctacca ggccactgtt
1801  gctttctgca tctgtcccac tgaaccagtc ttgtcctttg accctgagtt
1851  tccccaaatg cacacatcaa atccctgaat accaagggac taacctactt
1901  aatggcccat ttcttcagag ggtgtgggtt ttccctatag taagaaaatc
1951  tccacaagtt gaagcttaaa cagtaggctt tcgttcatac agtcctggaa
2001  gccagaatgg gtgtgagcag aatcacattt cctccggaga ctccaggagg
2051  gactttatag cttctggtga ctccaggaat ccttggcttg taacaatttc
2101  actctggcat tgctttccct gccatgtgac ttctgccttg tatgtgaggg
2151  cctgtatcaa atctctgtct tgggaggata cagatcattg acttagggcc
2201  cactccggtg acctcacctt cacctgaaat ttactcgatt tccatttagg
2251  tcagaggcaa aggctacaaa aaatatcaaa tccggagaaa gattcaatgg
2301  ttaggcactt gctactctta caaaggacct gtgttcgatt cccatgttgg
2351  gaactcatgt taggtggctt aaaattgcct ataactacaa ttccagggga
2401  tctagcaacc tcttctcgcc acacacaagc acacacacac acacacacac
2451  acacacacaa ttaaaaac
```
ORF in bold SEQ ID NO 5: Rat Meteorin-like cDNA (NM_001014104.1)
```
   1  ggcagccggc gcgcttctct ggttgcagct tgggcggctg gggcggctcc
  51  tatggtgggc ggccaggggc tagacgggat ggcctgtaga cgcgcgacgt
 101  gatcagctcg cacgcggacc cacgcctccc gcagcactgc ctcaacagtc
 151  tattctgtgg gtgcaggcac gcaccggtct cagaccctgc cggagcatgc
 201  ggggtgtggt gtgggcggcc cggaggcgcg cggggcagca gtggcctcgg
 251  tccccgggcc ctgggccggg tccgccccg ccgccaccgc tgctgttgct
 301  gctactgctg ctgctgggcg gcgcgagcgc gcagtactcc agcgacctgt
 351  gcagctggaa ggggagtggg ctcacccggg aggcacacag caaggaggtg
```

```
 401   gagcaggtgt acctgcgctg ctcagcaggc tctgtggaat ggatgtaccc 451   aaccggggcg ctcattgtta acctacggcc aaacccttc tcacctgccc 501   agaacttgac tgtgtgcatc aagcctttca gggactcctc tggggccaat 551   atttatttgg aaaaaactgg agaactaaga ctgttggtgc gggatgtcag 601   aggcgaacct ggccaagtgc agtgcttcag cctagagcag ggaggcttat 651   ttgtggaggc cacacccag caggacatca gcagaaggac cacaggcttc 701   cagtatgagc tgatgagtgg gcagagggga ctggacctgc acgtgctctc 751   tgccccctgt cgaccttgca gcgacactga ggtcctcctt gccatctgca 801   ccagtgactt tgttgtccga ggcttcatcg aggatgtcac ccatgtacca 851   gaacagcaag tgtcagtcat tcacctacgg gtgagcaggc tccacaggca 901   gaagagcagg gtcttccagc cagctcctga ggacagtggc cactggctgg 951   gccatgtcac aacactgttg cagtgtggag tacgaccagg catggagaa 1001   ttcctcttca ctggacatgt gcactttggg gaggcacaac ttggatgtgc 1051   cccacgcttt agtgactttc aaaagatgta caggaaagca gaagaaaggg 1101   gcataaaccc ttgtgaaata aatatggagt gacttgcagg gCgacaccgt 1151   actgctgtcc ttcagatgag ccatggctca gttgctctat caaatcccga 1201   tagagattgc agactggtgg catgagcccc gcctggtgct tgaactggga 1251   agggaggtac atgctgctct gaccccttag gtcccattca aggatgccct 1301   gacccattgg aaatgttgta aaatgcaaac taagttatta tattttttt 1351   gtaaagaaa aaaaaaaaa aaaaaaaaa
```
ORF in bold SEQ ID NO 13, human ORF
```
atgcggggcg cggcgcgggc ggcctggggg cgcgcggggc agccgtggcc gcgacccccc    60
gccccgggcc cgccccgcc gccgctcccg ctgctgctcc tgctcctggc cgggctgctg   120
ggcggcgcgg gcgcgcagta ctccagcgac cggtgcagct ggaaggggag cgggctgacg   180
cacgaggcac acaggaagga ggtggagcag gtgtatctgc gctgtgcggc gggtgccgtg   240
gagtggatgt acccaacagg tgctctcatc gttaacctgc ggcccaacac cttctcgcct   300
gcccggcacc tgaccgtgtg catcaggtcc ttcacggact cctcggggc caatatttat   360
ttggaaaaaa ctggagaact gagactgctg gtaccggacg gggacggcag gcccggccgg   420
gtgcagtgtt ttggcctgga gcagggcggc ctgttcgtgg aggccacgcc gcagcaggat   480
atcggccgga ggaccacagg cttccagtac gagctggtta ggaggcacag ggcgtcggac   540
ctgcacgagc tgtctgcgcc gtgccgtccc tgcagtgaca ccgaggtgct cctagccgtc   600
tgcaccagcg acttcgccgt cgaggctcc atccagcaag ttacccacga gcctgagcgg   660
caggactcag ccatccacct gcgcgtgagc agactctatc ggcagaaaag cagggtcttc   720
gagccggtgc ccgagggtga cggccactgg caggggcgcg tcaggacgct gctggagtgt   780
ggcgtgcggc cggggcatgg cgacttcctc ttcactggcc acatgcactt cggggaggcg   840
cggctcggct gtgccccacg cttcaaggac ttccagagga tgtacaggga tgcccaggag   900
agggggctga acccttgtga ggttggcacg gactga                           936
```
SEQ ID No 14, mouse ORF
```
atgcggggtg cggtgtgggc ggcccggagg cgcgcggggc agcagtggcc tcggtccccg    60
ggccctgggc cggtccgcc cccgccgcca ccgctgctgt tgctgctact actgctgctg   120
ggcggcgcga gcgctcagta ctccagcgac ctgtgcagct ggaagggag tgggctcacc   180
```

-continued

```
cgagaggcac gcagcaagga ggtggagcag gtgtacctgc gctgctccgc aggctctgtg      240
gagtggatgt acccaactgg ggcgctcatt gttaacctac ggcccaacac cttctcacct      300
gcccagaact tgactgtgtg catcaagcct ttcagggact cctctggagc caatatttat      360
ttggaaaaaa ctggagaact aagactgttg gtgcggaca tcagaggtga gcctggccaa       420
gtgcagtgct tcagcctgga gcagggaggc ttatttgtgg aggcgacacc ccaacaggac      480
atcagcagaa ggaccacagg cttccagtat gagctgatga gtgggcagag gggactggac      540
ctgcacgtgc tgtctgcccc ctgtcggcct tgcagtgaca ctgaggtcct ccttgccatc      600
tgtaccagtg actttgttgt ccgaggcttc attgaggacg tcacacatgt accagaacag      660
caagtgtcag tcatctacct gcgggtgaac aggcttcaca ggcagaagag cagggtcttc      720
cagccagctc ctgaggacag tggccactgg ctgggccatg tcacaacact gctgcagtgt      780
ggagtacgac cagggcatgg ggaattcctc ttcactggac atgtgcactt tggggaggca      840
caacttggat gtgccccacg ctttagtgac tttcaaagga tgtacaggaa agcagaagaa      900
atgggcataa accctgtga  aatcaatatg gagtga                                 936
```

SEQ ID NO 15, rat ORF
```
atgcggggtg tggtgtgggc ggcccggagg cgcgcgggc agcagtggcc tcggtccccg        60
ggcggcgcga gcgcgcagta ctccagcgac ctgtgcagct ggaagggggag tgggctcacc    180 cgggaggcac acagcaagga ggtggagcag gtgtacctgc gctgctcagc aggctctgtg     240
gaatggatgt acccaaccgg ggcgctcatt gttaacctac ggcccaacac cttctcacct      300
gcccagaact tgactgtgtg catcaagcct ttcagggact cctctgggc caatatttat       360 ttggaaaaaa ctggagaact aagactgttg gtgcgggatg tcagaggcga acctggccaa     420
gtgcagtgct tcagcctaga gcagggaggc ttatttgtgg aggccacacc ccagcaggac      480
atcagcagaa ggaccacagg cttccagtat gagctgatga gtgggcagag gggactggac      540
ctgcacgtgc tctctgcccc ctgtcgacct tgcagcgaca ctgaggtcct ccttgccatc      600
tgcaccagtg actttgttgt ccgaggcttc atcgaggatg tcacccatgt accagaacag      660
caagtgtcag tcattcacct acgggtgagc aggctccaca ggcagaagag cagggtcttc      720
cagccagctc ctgaggacag tggccactgg ctgggccatg tcacaacact gttgcagtgt      780
ggagtacgac cagggcatgg agaattcctc ttcactggac atgtgcactt tggggaggca      840
caacttggat gtgccccacg ctttagtgac tttcaaaaga tgtacaggaa agcagaagaa      900
aggggcataa acccttgtga aataaatatg gagtga                                 936
```

SEQ ID NO 16, Human CDS mature METRNL
```
cagtactcca gcgaccggtg cagctggaag gggagcgggc tgacgcacga ggcacacagg       60
aaggaggtgg agcaggtgta tctgcgctgt gcggcgggtg ccgtggagtg gatgtaccca     120
acaggtgctc tcatcgttaa cctgcggccc aacaccttct cgcctgcccg gcacctgacc      180
gtgtgcatca ggtccttcac ggactcctcg ggggccaata tttatttgga aaaaactgga     240
gaactgagac tgctggtacc ggacggggac ggcaggcccg gccgggtgca gtgttttggc      300
ctggagcagg gcggcctgtt cgtggaggcc acgccgcagc aggatatcgg ccggaggacc      360
acaggcttcc agtacgagct ggttaggagg cacagggcgt cggacctgca cgagctgtct      420
gcgccgtgcc gtccctgcag tgacaccgag gtgctcctag ccgtctgcac cagcgacttc      480
gccgttcgag gctccatcca gcaagttacc cacgagcctg agcggcagga tcagccatc      540 cacctgcgcg tgagcagact ctatcggcag aaaagcaggg tcttcgagcc ggtgcccgag      600
ggtgacggcc actggcaggg gcgcgtcagg acgctgctgg agtgtggcgt gcggccgggg     660
catggcgact cctcttcac tggccacatg cacttcgggg aggcgcggct cggctgtgcc      720
```

-continued

```
ccacgcttca aggacttcca gaggatgtac agggatgccc aggagagggg gctgaaccct    780
tgtgaggttg gcacggactg a                                              801

SEQ ID NO 17, Mouse CDS mature METRNL
cagtactcca gcgacctgtg cagctggaag gggagtgggc tcacccgaga ggcacgcagc     60
aaggaggtgg agcaggtgta cctgcgctgc tccgcaggct ctgtggagtg gatgtaccca    120
actggggcgc tcattgttaa cctacggccc aacaccttct cacctgccca gaacttgact    180
gtgtgcatca agcctttcag ggactcctct ggagccaata tttatttgga aaaaactgga    240
gaactaagac tgttggtgcg ggacatcaga ggtgagcctg gccaagtgca gtgcttcagc    300
ctggagcagg gaggcttatt tgtggaggcg acacccaac aggacatcag cagaaggacc     360
acaggcttcc agtatgagct gatgagtggg cagagggac tggacctgca cgtgctgtct    420 gcccctgtc ggccttgcag tgacactgag gtcctccttg ccatctgtac cagtgacttt     480
gttgtccgag gcttcattga ggacgtcaca catgtaccag aacagcaagt gtcagtcatc    540
tacctgcggt tgaacaggct tcacaggcag aagagcaggg tcttccagcc agctcctgag    600
gacagtggcc actggctggg ccatgtcaca acactgctgc agtgtggagt acgaccaggg    660
catggggaat tcctcttcac tggacatgtg cactttgggg aggcacaact tggatgtgcc    720
ccacgcttta gtgactttca aaggatgtac aggaaagcag aagaaatggg cataaacccc    780
tgtgaaatca atatggagtg a                                              801

SEQ ID NO 18, Rat CDS mature METRNL
cagtactcca gcgacctgtg cagctggaag gggagtgggc tcacccggga ggcacacagc     60
aaggaggtgg agcaggtgta cctgcgctgc tcagcaggct ctgtggaatg gatgtaccca    120
accggggcgc tcattgttaa cctacggccc aacaccttct cacctgccca gaacttgact    180
gtgtgcatca agcctttcag ggactcctct ggggccaata tttatttgga aaaaactgga    240
gaactaagac tgttggtgcg ggatgtcaga ggcgaacctg gccaagtgca gtgcttcagc    300
ctagagcagg gaggcttatt tgtggaggcc acacccagc aggacatcag cagaaggacc     360
acaggcttcc agtatgagct gatgagtggg cagagggac tggacctgca cgtgctctct    420 gcccctgtc gaccttgcag cgacactgag gtcctccttg ccatctgcac cagtgacttt     480
gttgtccgag gcttcatcga ggatgtcacc catgtaccag aacagcaagt gtcagtcatt    540
cacctacggg tgagcaggct ccacaggcag aagagcaggg tcttccagcc agctcctgag    600
gacagtggcc actggctggg ccatgtcaca acactgttgc agtgtggagt acgaccaggg    660
catggagaat tcctcttcac tggacatgtg cactttgggg aggcacaact tggatgtgcc    720
ccacgcttta gtgactttca aaagatgtac aggacatcag aagaagggg cataaaccct     780 tgtgaaataa atatggagtg a                                              801
```

Example 2

Obtaining METRNL Polypeptide and Functional Testing of METRNL Polypeptide

Methods

Sequence Analysis. Homology searches were performed with BLAST and by browsing the Ensembl Genome Browser. Alignment of amino acid sequences was done using CLUSTAL W (1.7) (Thompson et al (1994) Nucleic Acids Res. 22, 4673-4680) in the Clone Manager 9 Professional Edition package from Sci Ed Software (Cary, N.C.). Prediction of signal peptide cleavage sites was done using SignalP (Bendtsen et al (2004), J. Mol. Biol. 340, 783-795).

Cloning. The coding sequence of Meteorin-like from mouse (NM_144797) and human (NM_001004431) was synthesized with a C-terminal histidine tag (GSGSGSHHH-HHH; SEQ ID NO 26) by GenScript (NJ, USA) and PCR cloned BamHI/XhoI in pNS1n (Jensen et al., 2002). All constructs were verified by DNA sequencing (MWG Biotech AG, Germany).

Cell culture. HEK293 cells were grown as adherent cultures in DMEM (Invitrogen, 41965-039) supplemented with 10% FCS (Seromed, S 0115). Transfection was done using LipofectAMINE 2000 (Life Technologies, 11668-027) according to the manufacturer's instructions. Cells were incubated at 37° C. with a humidified atmosphere of 5% $CO_2$.

SDS-PAGE and Western blotting. Cell lysates and conditioned media were prepared as previously described (Fjord-Larsen et al (2005), Exp. Neurol. 195, 49-60). Samples were loaded on 15% homogenous SDS PAGE gels (Amersham Pharmacia, Sweden), electrophoresed and electroblotted to PVDF membranes. Detection of HIS tagged recombinant Meteorin-like was done using Anti-HIS (C-term) (Invitrogen, R930-25) at 0.2 µg/ml as primary antibody and HRP-linked anti-mouse Ab (Dako, $PO_{260}$, 1:2000) as secondary antibody. Alternatively gels were stained with GelCode Blue Stain Reagent (Pierce, 24590) according to manufacturer's instructions.

Production of recombinant mouse meteorin-like. FreeStyle™ 293-F cells (Invitrogen, K9000) were transfected with pNS1n-mMETRNL-HIS DNA using Lipofectamine 2000 (Life Technologies, 11668-027). The culture was incubated with agitation at 37° C. and 8% $CO_2$ for four days and separated into cell pellet and supernatant by centrifugation. The supernatant was sterile filtered and recombinant protein purified with TALON Metal Affinity Resin (Clonetech, 635502) followed by PD-10 gel filtration (GE Healthcare, 17-0851-01).

RP-HPLC. Reversed phase chromatography was done on a C4 column (1×150 mm, Phenomenex Jupiter, C4, 5 µm, 300 Å). The elution was performed with a linear gradient (0-100% in 60 min) of acetonitrile in 0.1% TFA using a flow rate of 50 µl/min. Detection was at 214 nm.

Mass spectrometry. Matrix-assisted laser desorbtion/ionization time-of-flight (MALDI-TOF) mass spectrometry as described previously (Ylonen et al., 1999). For peptide mass fingerprint analysis, mMETRNL protein was reduced, alkylated with iodoacetamide and digested with trypsin prior to analysis.

DRG culture. Rat P5 dorsal root ganglions were dissociated using Papain Dissociation System (Worthington Biochemical Corp, US) supplemented with 1.2 mg/ml Collagenase D (Roche) and 4.8 mg/ml Dispase (Roche). Cells were subsequently plated in Polyornithine/laminin-coated 24-well plates in DMEM/F12 medium (Invitrogen) with 5% heat-inactivated Horse Serum (Seromed) at a cell density of $1.5 \times 10^4$ cells/cm². After 1 hour when the cells had attached, medium was changed to serum-free DMEM/F12 with 1% Gentamycin (Invitrogen) and the indicated additions of recombinant murine Meteorin-like or rat NGF (R&D Systems, 556-NG). Cells were incubated at 37° C. and 5% $CO_2$ for 1 day and fixed in 4% PFA. Immunocytochemistry was performed on the fixed cultures using β-III-Tubulin antibody (Sigma, T-8660) diluted 1:15.000 in 1% normal horse serum and 0.1% Triton X-100 in PBS followed by biotinylated secondary antibody (horse-anti-mouse) followed by ABC Elite kit (Vector Laboratories), whereafter the color reaction was developed using 3'3'-diaminobenzidine (DAB) as cromogen. Neurite length per cell was quantified using VisioMorph image analysis. At least nine images from triplicate wells were used.

SVZ Explants. Newborn rat pups from P2-P3 were sacrificed by decapitation. Brains were dissected and placed in cold Neurobasal medium (Gibco-Invitrogen, Carlsbad, Calif.) and brain slices with 250 µm thickness were obtained by using a vibratome. The SVZ was dissected from the lateral wall of the anterior horn of the lateral ventricle and cut into pieces of 150-200 µm in diameter. The SVZ explants were mixed with Matrigel (Becton Dickinson) at a ratio of 1:5 and cultured in four-multiwell plates. After polymerization at 37° C. (25 min) 500 µl of Neurobasal medium supplemented with B-27 (Gibco-Invitrogen), N 2-factor (Gibco-Invitrogen) and Penicillin/Streptomycin (Gibco-Invitrogen) was added to control cultures. Other conditions consisted of the same medium but with different concentrations of murine METRNL (20 ng/ml and 200 ng/ml). Cultures were maintained in a humidified, 5% $CO_2$, 37° C. incubator.

Immunofluorescence. After 24 h, SVZ explants were washed with PBS and fixed with 4% PFA in PBS, 0.05% Triton-X 100 for 15 minutes. Explants were incubated for 1 hour with blocking buffer containing PBS, 2% horse serum, 1% BSA, 0.1% gelatin, 0.1% Triton X-100 and 0.05% Tween 20. Explants were incubated for 1 hour at room-temperature with goat anti-DCX (1:100, Santa Cruz). Explants were rinsed with PBS and incubated for 1 hour at room-temperature with Cy3-conjugated anti-goat secondary antibody (1:200, Jackson ImmunoResearch). Sections were rinsed with PBS, mounted in glass slides and cover-slipped.

Quantification of cell migration. After 24 h, explants were monitored with a DIC microscope and the length of migratory chains from each explant was measured by using AxioVision software (Zeiss). Measurements of the distance between the edge of the explant and the distinguishable migration front were performed and then normalized against the values obtained from the control measurements. Experiments were performed in two independent assays.

FITC-Phalloidin Assay with Sub-Ventricular Zone (SVZ) Explants

SVZ tissue was isolated from P2-P5 rat pups and cultured as described. Explants were stimulated for 24 hours with 20 ng/ml METRNL or 10 ng/ml SDF1a and restimulated one hour before fixation in 4% PFA/0.05% Triton-X. After fixation explants were washed with PBS and stained for 20 minutes with FITC-Phalloidin (Invitrogen) diluted 1:50. Stained explants were mounted on glass slides and visualized using fluorescence microscopy.

FITC-Phalloidin Assay with SVZ-Derived Cell Monolayers

SVZ tissue was isolated from P2-P5 rat pups and incubated with accutase for 15 minutes in order to detach cells. After accutase treatment, cells were dissociated with a glass Pasteur pipette, then counted and placed on glass coverslips coated with ornithine/fibronectin. SVZ cells were kept in Neurobasal culture medium supplemented with B-27, N2 supplement, glutamine and pen-strep. After 24 hours cells were stimulated for one hour with 20 ng/ml METRNL or 10 ng/ml SDF1-a before fixation in 4% PFA/0.05% Triton-X. After fixation, cells were washed with PBS and stained for 20 minutes with FITC-Phalloidin (Invitrogen) diluted 1:50. Stained cells were mounted on glass slides and visualized using fluorescence microscopy.

Production of Recombinant Human METRNL

FreeStyle 293F cells were transfected with pNS1n expressing codon optimized HIS tagged human METRNL. Cell culture and purification were done as previously described.

Results

Meteorin-Like and Meteorin Constitute a Novel Family of Secreted Proteins

Human METRNL and METRN proteins are 42% identical and ten out of ten existing cysteine residues in the mature sequence are conserved (FIGS. 1 and 3). Analysis of EST and genome sequences from various organisms suggests orthologues for METRNL in all vertebrates including zebrafish and the frog *Xenopus tropicalis*, whereas no orthologues are found in the invertebrates such as the fruit fly (*Drosophila melanogaster*) and the nematode (*Caenorhabditis elegans*) (FIG. 3).

SignalP predicted the existence of an N-terminal signal peptide with a predicted cleavage site between A45 and Q46 in human, mouse and rat METRNL.

C-terminally HIS-tagged versions of human and mouse METRNL were cloned and transiently transfected in HEK293 cells. From FIG. 4 it is clear that both molecules are produced and secreted. hMETRNL travels at the expected 31.2 kDa but mMETRNL travels at a higher molecular weight.

Production of Recombinant mMETRNL

To be able to study biochemical properties of METRNL, recombinant protein was produced in FreeStyle™ 293-F cells. As evident from FIG. 5A, mMETRNL-HIS protein accumulates continuously in conditioned media up to 96 hours post transfection. Accordingly, in scaled-up cultures conditioned media was harvested 96 hours after transfection and recombinant mMETRNL-HIS purified by TALON resin binding. From SDS-PAGE analysis of the purified protein in FIG. 5B, there is only one Anti-HIS immunoreactive band corresponding in size to the single band detected by GelCode Blue staining. Again, mMETRNL-HIS travels at a higher molecular weight than the expected 31.2 kDa. Purified protein was further analyzed by reverse phase chromatography. From the chromatogram (FIG. 5C), it is evident that mMETRN-HIS eluted as a single dominating peak with few impurities. The shoulder in fractions ≥31 is typical for heterogeneously glycosylated proteins. To investigate glycosylation, purified recombinant protein was incubated with different deglycosylating enzymes and combinations hereof. From FIG. 5D, it is clear that treatment with N-Glycanase causes a decrease in molecular weight and the addition of other deglycosylation enzymes does not decrease the molecular weight further. This means that mMETRNL is a glycoprotein with N-linked oligosaccharides only.

Finally, the trypsin peptide mass fingerprint of the purified protein was compared to the theoretical in silico digest of rat histidine-tagged mMETRNL. This way, the major part of the sequence within the detection range (800-3500 Da) was confirmed but there was no 1272.5 Da tryptic peptide as would be expected if the signal sequence was cleaved between A45 and Q46 as predicted. However, if a glutamine residue is at the N-terminus it may cyclize spontaneously or enzymatically into a pyrrolidone carboxylic acid, which will result in a mass reduction of 17 Da. Consequently, this would lead to a tryptic N-terminal peptide of 1255.5 Da and this mass is indeed found in the generated peptide mass list. Therefore, mature mMETRNL starts at Q46 which is cyclized. From the alignment of METRNL from human, cow, mouse, rat, chicken, xenopus tropicalis and zebrafish (FIG. 3) it is evident that the N-terminal glutamine in the mature protein is conserved throughout development.

METRNL is Neurotrophic

To investigate neurotrophic effects of mMETRNL, purified recombinant protein was added to cultures of rat P5 dissociated dorsal root ganglions (DRGs). Indeed, Meteorin-like stimulates neurite outgrowth (FIG. 6) with a potency comparable to that of NGF. Without trophic support, neurite outgrowth from DRG cells is very limited but in the presence of NGF or mMETRNL, long neurites from β-III-Tubulin positive neurons are formed. The observed effects may include an enhanced survival of neural cells, enhanced regeneration of neural cells, and differention of neural cells.

Effects in this assay indicates therapeutic potential in ALS, root injury, root avulsion, brachial nerve injury, peripheral neuropathies and neuropathic pain.

In general, neurotrophic factors are responsible for growth and survival of neurons during development, and for maintaining adult neurons. Furthermore, these factors also are capable of repairing specific damaged neuronal populations and as such have therapeutic potential for reversing disorders of the central nervous system, including Alzheimer's disease (Schindowski et al (2008). Genes Brain Behav. 7 Suppl 1, 43-56), Parkinson's disease (Evans et al (2008), Expert. Opin. Ther. Targets. 12, 437-447) and amyotrophic lateral sclerosis (Ekestern (2004) Neurodegener. Dis. 1, 88-100).

METRNL Increases Neuronal Migration of Neuroblasts Derived from the Rat SVZ in a Dose-Dependent Mode.

The effect caused by METRNL on neurite outgrowth in dorsal root ganglions (FIG. 6) suggests a function of this protein at the level of cell membrane remodeling. If this is the case, then it is also conceivable that METRNL would affect the behaviour of migratory cells like neuroblasts derived from the SVZ, if they express the machinery to transduce the signal triggered by the presence of METRNL. To address its possible function in neuroblast migration, purified recombinant METRNL was added to rat SVZ explants cultured in the three-dimensional extracellular matrix (Matrigel). The presence of METRNL caused a significant increase of cell migration in a dose-dependent mode, in which a concentration of 200 ng/ml of METRNL gave rise to approximately 50% increment of migratory distance comparing to control conditions (FIG. 7). Since explants derived from the SVZ have a heterogeneous composition, it is important to identify which cells are responding to METRNL. Therefore, immunostainings with a specific antibody against Doublecortin (DCX), a marker expressed by migratory neuroblasts, were performed. The results revealed that the cells that displayed increased migration were neuroblasts and not astrocytes (FIG. 7).

METRNL Increases Neuronal Migration of SVZ Derived Neuroblasts

To confirm the effect of METRNL on neuroblast migration, purified recombinant mouse METRNL was added to rat SVZ explants cultured in the three-dimensional extracellular matrix (Matrigel). The presence of mouse METRNL caused a significant increase of cell migration in a dose-dependent mode. 200 ng/ml of METRNL almost doubled the migratory distance compared to control conditions (FIG. 8A). Increasing the METRNL concentration to 2000 ng/ml did not further increase migration. The migrating cells were identified as neuroblasts as they were Doublecortin (DCX) positive and Glial Fibrillary Acidic Protein (GFAP) negative (FIG. 8B).

Actin polymerization provides the basic machinery for cell migration. This can easily be monitored by incubation with actin binding FITC conjugated phalloidin followed by fluorescence microscopy. From FIG. 9 it is clear that stimulation with METRNL leads to actin polymerization in SVZ neuroblasts both in explants and in monolayer cultures to the same extend as the positive control SDF1a. In the explant cultures, is very evident how the cells are using each other as a substrate forming long chains of cells which is typical for neuroblast migration (chain migration). The increase in actin polymerization and the migration pattern is further evidence for a role of METRNL in promoting neuroblast migration. In addition, the number of DCX positive neuroblasts increased in cultures with both METRL and SDF-1 as compared to control indicating evidence of neurogenesis. The effect of SDF-1 on neurogenesis is well described and as the number and migration pattern of DCX+ neuroblasts cells for METRL stimulated cultures were indistinguishable from SDF-1 cultures, on can conclude that METRL has positive effects on both neurogenesis and neuroblast migration even though there was no attempt made to quantify the number of neuroblast in these experiments.

Mature mouse and human METRNL are 78% identical. To demonstrate that the two molecules have similar biological activity, purified human recombinant METRNL was added to rat SVZ explants. Indeed, as apparent in FIG. 10, human METRNL also promote neuroblast migration.

These results suggest a promising stimulatory action of METRNL in neuroblast migration. The observed results may also include enhanced survival of neural cells, and enhanced neurogenesis.

Delivery of this protein may have a potential application in therapies for neurodegenerative disorders like stroke, PD, HD, ALS, and Alzheimer's disease, which could benefit from the recruitment of new neurons to the injured regions.

Secreted factors seem particularly useful to study for therapeutic purposes because of the influence that they might have in migratory cells with a high potential for tissue repair, once they can influence how cells proliferate, migrate and differentiate. When putative factors are available to test, several experimental sets can be used as an approach to address their function, allowing a fast read-out and validation. In this case we use a method described by Wichterle (Wichterle et al (1997), Neuron 18, 779-791) which comprises the preparation of tissue explants from the murine SVZ, that are embedded in a three-dimensional extracellular matrix gel composed of collagen IV, laminin, heparan sulfate proteoglycans and entactin-nidogen. Once SVZ explants are embedded in the Matrigel, they can be kept in culture in the presence of factors to test, and migration can be monitored at different time points. In standard conditions, migratory neuroblasts exit radially from the explants forming chains, because they use each other as a substrate for migration. Depending on the time point of the measurement, these migratory chains can be one to five cells wide and up to 600 μm long and display an average speed of 122 μm/hour (Wichterle et al., 1997). In cases when factors, inhibitors or transgenic tissue are analyzed, these parameters can be taken in account for measurements to quantify and compare with control conditions (Hack et al (2002) Nat. Neurosci. 5, 939-945; Alberti et al (2005), Proc. Natl. Acad. Sci. U.S.A 102, 6148-6153; Chiaramello et al (2007), Eur. J. Neurosci. 26, 1780-1790). These methods are particularly convenient to screen for factors with a possible application in therapies for neurodegenerative diseases that imply regulated cell migration at the SVZ because the tested cells are derived precisely from this region and not from a region with different cell types that could behave in different modes to the same conditions.

Example 2A

METRNL Protects Deafened Guinea Pigs from Hearing Loss

Materials and Methods

An overview of the experimental design is shown in FIG. 11A. Initially, eighteen guinea pigs (albino) were tested for normal hearing using click-evoked auditory brainstem response (ABR) and divided into the following three experimental groups:
1. Normal hearing animals treated with METRNL
2. Three weeks deafened animals treated with METRNL
3. Three weeks deafened animals treated with artificial perilymph (AP)

Group 1: At time 0, six normal hearing guinea pigs received a cannula connected to a mini-osmotic pump for inner ear infusion of METRNL and a cochlear implant for monitoring the electrical responsiveness of the spiral ganglion neurons (Maruyama et al., Neurobiol Dis. 25, 309-318, 2007). Animals were treated for two days with AP followed by two weeks treatment with a 1 μg/ml METRNL solution in AP delivered at 0.5 μl/h.

Group 2: After initial ABR measurements (time=−21 days) animals received a single injection through the tympanic membrane with 10% neomycin on both ears. After 7 and 14 days, click-ABR was measured to investigate the threshold after deafening. The goal was to obtain >60 dB threshold shift, indicating a very severe hearing loss. One out of six animals did not have a >60 dB threshold and was therefore excluded from the experiment. Three weeks after deafening (time=0) five animals underwent surgery and received a cochlear implant and a cannula connected to a mini-osmotic pump. Animals received AP for two days followed by two weeks treatment with METRNL as described above.

Group 3: Animals were deafened as in group 2 and again one animal was excluded because of ineffective deafening. The remaining five animals received cochlear implants at t=0 and AP treatment throughout the remaining study.

For all groups, electrically-evoked auditory brainstem response (eABR) was measured at 2, 9 and 16 days after surgery.

Results

METRNL has a Positive Effect on Spiral Ganglion Survival and Electrical Responsiveness In Vivo To confirm the effect of METRNL on treatment of damage to the sensory epithelium and associated ganglia of the inner ear, including but not limited to noise induced hearing loss, deafness, tinnitus, otitis, labyrintitis, hereditary and cochleovestibular atrophies, Meniere's Disease, and associated symptoms, METRNL was tested in an animal model of deafness. In brief, guinea pigs were deafened with a single dose of neomycin and three weeks later treated with METRNL by protein infusion (FIG. 11A). Electrically auditory brainstem response (eABR) was recorded 2, 9 and 16 days after surgery in order to monitor threshold changes related to the different treatments (FIG. 11B). Threshold in normal hearing guinea pigs treated with METRNL were stable throughout the experiment (~50 μA) indicating that METRNL has no harmful effects on hearing. In the two deafened groups, the threshold was elevated in the first recording indicating severely reduced hearing. Importantly, where the eABR threshold continued to rise in the control group treated with artificial perilymph, the METRNL treated group showed a statistically significant ($p<0.05$) lower threshold in comparison after 16 days treatment. This implies that METRNL has a positive effect on spiral ganglion neuron survival and their electrical responsiveness in vivo. This is a short time study and longer time treatment would be expected to improve hearing even further (Maruyama et al., Neurobiol Dis. 2008 January; 29(1):14-21). Accordingly, METRNL may be used to treat damage to the sensory epithelium and associated ganglia of the inner ear, including but not limited to noise induced hearing loss, deafness, tinnitus, otitis, labyrintitis, hereditary and cochleovestibular atrophies, Meniere's Disease, and associated symptoms.

Example 3

Protection of Cerebellar Granule Cells from Glutamate Toxicity

Testing for survival effects is carried out by treating cultures of cerebellar granule cells with recombinant METRNL that subsequently is exposed to toxic concentrations of glutamate essentially as described (Daniels and Brown, 2001; J. Biol. Chem. 276: 22446-22452).

Cerebellar granule neurons (CGN) are dissected from 7-8 days old mouse pups. Cells are dissociated from freshly dissected cerebella by enzymatic disruption in the presence of trypsin and DNase and then plated in poly-D-lysine-precoated 24-well plates (Nunc) at a density of $1-2\times10^6$ cells/$cm^2$ in DMEM medium supplemented with 10% heat-inactivated fetal calf serum.

Cells are cultured at 37° C. in a humidified atmosphere and Cytosine arabinoside (10 μM) is added to the culture medium after 24 hr to arrest the growth of non-neuronal cells.

Cultures are treated with a serial dilution of recombinant METRNL on DIV1 and parallel cultures receive PBS as a negative control. Media is replaced on a daily basis. At DIV5, glutamate (0.1-1 mM) is added to the cultures and after two additional days cell survival is assayed using the MTT assay. The extent of MTT reduction to formazane is measured spectrophotometrically at 570 nm. Briefly, culture medium is removed, and cells are washed in sodium saline solution (140 mM NaCl, 5 mM KCl, 1 mM $MgCl_2.6H_2O$, 1 mM $NaH_2PO_4$, 1.5 mM $CaCl_2$, 5.6 mM glucose, 20 mM HEPES, pH 7.4). MTT (final concentration 0.5 mg/ml), prepared just before using and maintained in the dark in sodium saline solution, is then added to the cells. After 3 h incubation at 37° C., an equal volume of acid-isopropanol (0.04 M HCl in isopropanol) is added and mixed thoroughly at room temperature until all formazan crystals were dissolved. Cell viability is expressed as a percentage of the optical density of control cells. Parallel cultures are left untreated.

Example 4

Protection of Cerebellar Granule Cells from Apoptosis Induced by Potassium Deprivation Testing for survival effects is carried out by treating cultures of cerebellar granule cells deprived of potassium with a serial dilution of recombinant METRNL essentially as described (Nomura et al., 2001; Dev. Neurosci. 23: 145-152).

Cerebellar granule neurons (CGN) are dissected from P8 NMRI mice pups. Cells are dissociated from freshly dissected cerebella by enzymatic disruption in the presence of Trypsin and DNase and then plated in poly-L-lysine-coated 48-well plates (Nunc) at a density of $4.4\times10^5$ cells/$cm^2$ in Eagle's basal medium (BME) containing 25 mM KCl and supplemented with 10% heat-inactivated fetal calf serum, 2 mM glutamine and 100 μg/ml Gentamycin. Cells are cultured at 37° C. in a humidified atmosphere and Cytosine arabinoside (10 μM) is added to the culture medium after 24 hr to arrest the growth of non-neuronal cells.

At DIV2, apoptosis is induced in immature cultures by switching the cells to serum-free BME with 5 mM KCl supplemented with 2 mM glutamine, 100 μg/ml Gentamycin and Cytosine arabinoside (low-potassium medium). A serial dilution of recombinant METRNL is added to the wells and parallel cultures receive PBS as a negative control or 100 ng/ml Insulin-like Growth Factor-1 (IGF-1) as a positive control. To determine the cell death induced by the potassium deprivation, cultures incubated in medium with 25 mM KCl are included as a reference. Survival is measured on DIV3, using the MTS assay.

At DIV8, apoptosis is induced in differentiated (neuronal) cultures by switching the cells to the serum-free low-potassium medium containing 5 mM KCl. Different concentrations of MTRNL are added and the same control cultures as described above are included. Survival is determined after 24-72 hr, using the MTS assay.

The MTS assay is carried out using the CellTiter 96® Aqueous Non-Radioactive Cell Proliferation Assay (Promega) following the manufacturer's instructions.

This assay can be considered as a general assay for neuroprotective effects as well as an assay predictive for factors with therapeutic potential in the treatment of cerebellar disorders.

Example 5

Effect on Motoneuron Cultures

Briefly, spinal cords of embryonic day 12.5 (E12.5) mouse embryos are dissected and dissociated. Motoneurons are purified using a protocol based on the immunoaffinity purification of motoneurons with antibodies against the extracellular domain of the neurotrophin receptor, p75, followed by cell sorting using magnetic microbeads (Arce et al. 1999 J Neurosci Res 55: 119-126). Purified motoneurons are seeded on 4-well tissue culture dishes (Nunc) coated with polyornithine/laminin at a density of 1000 cells per well. Culture medium is Neurobasal culture medium (Life Technologies) supplemented with B27 supplement (Life Technologies), horse serum (2% v/v), L-glutamine (0.5 mM), and 2-mercaptoethanol (25 μM).

A serial dilution of recombinant METRNL is added at the time of seeding and parallel cultures receive PBS as a negative control. Motoneuron survival is quantified after 2 days in culture by counting the number of large phase-bright neurons with long axonal processes in a predetermined area of 1.5 $cm^2$ in the center of duplicate dishes.

Protective effects in this assay indicates therapeutic potential in motoneuron diseases including ALS, Spinal Cord injury, SMA (spinal muscular atrophy), DMD (Duchenne muscular dystrophy).

Example 6

Bioassay for Dopaminergic Neurotrophic Activities

Culture Conditions:

Dissociated mesencephalic cell cultures are prepared as previously described (Friedman and Mytilineou 1987 Neurosci. Lett. 79:65-72) with minor modifications. Briefly, rostral mesencephalic tegmentum from brains of Sprague-Dawley rat embryos, at the 13th-16th day of gestation, are dissected under the microscope in sterile conditions, collected in $Ca^{2+}$- and $Mg^{2+}$-free Dulbecco's phosphate buffered saline (Gibco, Gaithersburg, Md.) and dissociated mechanically by mild trituration. The cells are plated in 100 μl per well onto 16-mm diameter tissue culture wells (Falcon, Lincoln Park, N.J., 24-well plate) containing 400 μl medium to give a density of $2.5-3.5\times10^5$ cells per well. The culture wells have been previously exposed to 0.1 mg/ml solution of poly L-ornithine in 10 mM sodium borate, pH 8.4, for 3 hours at 37° C., washed 3 times in milli-Q $H_2O$ and once in Earle's balanced salt solution (Gibco). The feeding medium (10/10) consists of minimal essential medium (MEM, Gibco) supplemented with glucose (33 mM), sodium bicarbonate (24.5 mM), glutamine (2 mM), HEPES (15 mM), penicillin G (5 U/ml), streptomycin (5 μg/ml), 10% heat-inactivated fetal calf serum (Gibco) and 10% heat inactivated horse serum (Gibco). The cultures are kept at 37° C. in a water-saturated atmosphere containing 6.5% $CO_2$. After 3 hours, when most of the cells have adhered to the bottom of the well, the medium is replaced with 500 μl of fresh medium. At this time, a serial dilution of the sample to be assayed for dopaminergic neurotrophic activity (solution of METRNL protein) is added to each well in duplicate and the plates are incubated in the 37° C. incubator. After a week, the cultures are treated for 24 hours with fluorodeoxyuridine (13 µg/ml) and uridine (33 µg/ml) to prevent excessive glial proliferation and subsequently fed with the above medium without fetal calf serum. The feeding medium is changed weekly.

Alternatively, chemically defined serum-free medium is used in which serum is replaced by a mixture of proteins, hormones and salts. The defined medium (DM) consists of a mixture of MEM and F12 nutrient mixture (both Gibco, 1:1; vol/vol) with glucose (33 mM), glutamine (2 mM) $NaHCO_3$ (24.5 mM), HEPES (15 mM), supplemented with transferrin (100 µg/ml), insulin (25 µg/ml), putrescine (60 µM), progesterone (20 nM), sodium selenite (30 nM), penicillin G (5 U/ml) and streptomycin (5 µg/ml). The osmolarity of the DM is adjusted to 325 by the addition of milli-Q $H_2O$. (110-125 ml $H_2O$/l).

The functional status of the dopaminergic neurons may be assayed in these cultures by measuring dopamine uptake through specific "scavenger" transporters in the dopaminergic neurons and by counting the number of neurons positive for the dopamine synthetic enzyme tyrosine hydroxylase using immunohistochemistry as described in Karlsson et al, 2002, Brain Res. 2002 Nov. 15; 955(1-2):268-80.

Sample Preparation:

Prior to being assayed for dopaminergic neurotrophic activity in the mesencephalic cell cultures, all the samples of conditioned medium are desalted as follows. One hundred µl of the medium 10/10 (as a carrier) is added to a Centricon-10 (Amicon) and allowed to sit for 10 minutes. Aliquots of the sample to be assayed are added to the Centricon, followed by 1 ml of Dulbecco's high glucose Modified Eagle medium, without bicarbonate, but containing 10 mM HEPES, pH 7.2 (solution A), and centrifuged at 5,000×g for 70 minutes. The retentate (about 0.1 ml) is brought back to 1.1 ml with fresh solution A and reconcentrated twice. The sample is filtered through a 0.11 µm Ultrafree-MC sterile Durapore unit (Millipore, Bedford Mass.) prior to being added to the culture well.

$^3$H-Dopamine Uptake:

Uptake of tritiated dopamine ($^3$H-DA) is performed in cultures at day 6 or day 7 as described previously (Friedman and Mytilineou (1987) Neurosci. Lett. 79:65-72) with minor modifications, and all the solutions are maintained at 37° C. Briefly, the culture medium is removed, rinsed twice with 0.25 ml of the uptake buffer which consists of Krebs-Ringer's phosphate buffer, pH 7.4, containing 5.6 mM glucose, 1.3 mM EDTA, 0.1 mM ascorbic acid and 0.5 mM pargyline, an inhibitor of monoamine oxidase. The cultures are incubated with 0.25 ml of 50 nM $^3$H-DA (New England Nuclear, Boston, Mass. sp. act 36-37 Ci/mmol) for 15 minutes at 37° C. $^3$H-DA uptake is stopped by removing the incubation mixture and cells are then washed twice with 0.5 ml of the uptake buffer. In order to release $^3$H-DA from the cells, the cultures are incubated with 0.5 ml of 95% ethanol for 30 min at 37° C., and then added to 10 ml of EcoLite (ICN, Irvine, Calif.) and counted on a scintillation counter. Blank values are obtained by adding to the uptake buffer 0.5 mM GBR-12909 (RBI), a specific inhibitor of the high-affinity uptake pump of the dopamine neurons (Heikkila et al. 1984 Euro J. Pharmacol. 103:241-48).

An increase in the number of TH positive neurons and/or an increase in $^3$H-dopamine uptake compared to a control treatment are an indication of a possible function of METRNL in the treatment of Parkinson's disease.

Example 7

Assessment of Neuroprotection of Nigral Dopamine Neurons in the Rat Intrastriatal 6-OHDA Lesion Model VSV-G pseudotyped (rLV) vectors are produced as described previously (Zufferey et al., 1997, J. Virol, 73:2886-2892; Rosenblad et al. 2000 Mol Cell Neurosci. 15(2):199-214). Briefly, the transfer plasmids pHR'CMV-W carrying the cDNA for green fluorescent protein (GFP) or METRNL is co-transfected with the helper plasmids pMD.G and pCM-VDR8.91 into 293T cells. Virion containing supernatants are collected on days 2 and 3 after transfection and concentrated at 116 000 g by ultra centrifugation. The titer of rLV-GFP vector stock is determined by serial dilution of the concentrated supernatant on 293T cells. The viral particle titre is determined for rLV-METRNL and rLV-GFP virus stocks using an RNA slot blot technique as described previously (von Schwedler et al. 1993 Virol. 67(8):4945-55) and from the ratio between TU and viral particle titre obtained for rLV-GFP, the titre of the rLV-METRNL vector is estimated TU/ml All work involving experimental animals are conducted according to the guidelines set by the Ethical Committee for Use of Laboratory Animals. Rats are housed in 12:12 hour light/dark cycle with access to rat chow and water. Female Sprague-Dawley rats (~220 g by the time of surgery) are used. For stereotaxic surgery, animals are anaesthetized using Isofluran (Baxter) and a total of $2\times10^5$ TU/animal of rLV-GFP (n=8) or rLV-METRNL (n=8) of the viral stocks are injected into two tracts in the right striatum (1, 2) and one over the substantia nigra (3) at the following coordinates: (1) AP=+1.4 mm, ML=−2.6 mm, DV=−5.0 and −4.0 mm, Tb=−2.3, (2) AP=0.0 mm, ML=−3.7 mm, DV=−5.0 and −4.0 mm, Tb=−2.3 and (3) AP=−5.2 mm, ML=−2.0 mm, DV=−6.8 mm, Tb=−2.3. After two weeks the animals are again anaesthetized and placed in the stereotaxic frame. An injection of 6-hydroxydopamine (20 µg [calculated as free base] per 3 µl vehicle [saline with 0.2% ascorbic acid]) is made into the right striatum at the following coordinates: AP=+1.0 mm, ML=−3.0 mm, DV=−5.0 mm, Tb=−2.3.

At four weeks post-lesion the animals are deeply anaesthetized with pentobarbital (70 mg/kg, Apoteksbolaget, Sweden), and transcardially perfused with 50 ml saline at room temperature, followed by 200 ml ice-cold phosphate-buffered 4% paraformaldehyde (pH 7.2-7.4). The brains are postfixed for 3-6 hours in the same fixative, transferred to 30% sucrose for 24 hours and cut into 6 series of 40 µm thick sections on a freezing microtome.

Immunohistochemistry for detection of dopaminergic neurons (tyrosine hydroxylase (TH) and vesicular monoamine transporter (VMAT)-immunoreactive) in the substantia nigra is performed as described previously (Rosenblad et al. 2000 Mol Cell Neurosci. 15(2):199-214). The number of TH-IR and VMAT-IR nigral neurons in lesion versus control side for animals in each experimental group is assessed by stereological cell counting.

An increase in the number of surviving TH-IR neurons in the MTRNL-treated group compared to the GFP control is a strong indication of a function in the treatment of Parkinson's disease. An increase in the number of VMAT-IR further strengthens the conclusion.

Example 8

The Effect of hMETRNL on Differentiation of a Human Neural Progenitor Cells

Testing in hNS1 Cells hNS1 (formerly called HNSC.100) is an embryonic forebrain-derived, multipotent, clonal cell line of neural stem cells that has previously been described (VIIIa et al. 2000, Exp Neurol, 161(1):67-84). Villa et al 2004, Exp Cell Res. April 1; 294(2):559-70). Cells are obtained from Alberto Martinez Serrano, Department of Molecular Biology, Centre of Molecular Biology Severo Ochoa, Autonomous University of Madrid-CSIC, Campus Cantoblanco, Madrid, 28049, Spain. hNS1 cultures are expanded in poly-Lysine coated TC flasks at 5% $CO_2$ and 37° C. in serum-free HSC medium supplemented with 20 ng/ml of EGF and bFGF. HSC medium consists of DMEM/F12 (1:1) supplemented with N2 and 1% BSA. For differentiation experiments, hNS1 cells are seeded onto coverslips coated with 50 µg/ml poly-lysine in mitogen-free, 0.5% FBS containing HSC medium at a density of $10^5$ cells/$cm^2$. One day after seeding, the differentiation medium is changed to medium containing METRNL. A control culture receives HSC medium. Two-third of the medium is replaced the next day and then every second or third day. Four days after plating, cultures are fixed for 10 min in 4% paraformaldehyde and stained by immunohistochemistry.

Immunohistochemistry

After blocking in 10% normal horse serum, cultures are incubated with primary antibodies to GFAP (pAb rabbit anti-cow, 1:1000, DAKO) and β-tubulin (mAb clone SCL:3D10, 1:1000, Sigma). After being rinsed, cultures are incubated with secondary antibodies biotinylated horse-anti-mouse (Vector Laboratories, 1:200) followed by detection using Strep-Cy3 (Jackson ImmunoResearch, 1/200) and Alexa Fluor 488-labelled goat anti-rabbit (Molecular Probes, 1:200), respectively. Cell nuclei are counterstained with Hoechst 33258 at 0.2 µg/ml. (Villa et al., 2004). For the analysis, the total number of cells (nuclei) in addition to GFAP and β-tubulin positive cells is counted by confocal microscopy using a 63× objective.

An increased neuronal number in the presence of MTRNL may result from increased differentiation of neuronal progenitor cells present in the cultures and/or a survival effect on the differentiated neurons.

---

The invention claimed is:

1. A method of treatment of neuropathic pain in a human subject in need thereof, comprising administering to the subject a therapeutically effective amount of a neurotrophic polypeptide comprising an amino acid sequence that is at least 90% identical to SEQ ID NO:7.

2. The method of claim 1, wherein the polypeptide comprises an amino acid sequence that is at least 95% identical to SEQ ID NO:7.

3. The method of claim 1, wherein the polypeptide comprises an amino acid sequence that is at least 98% identical to SEQ ID NO:7.

4. The method of claim 1, wherein the polypeptide comprises the amino acid sequence of SEQ ID NO:7.

* * * * *